United States Patent
Taylor et al.

(10) Patent No.: US 10,913,726 B2
(45) Date of Patent: *Feb. 9, 2021

(54) CENTRALLY ACTIVE AND ORALLY BIOAVAILABLE ANTIDOTES FOR ORGANOPHOSPHATE EXPOSURE AND METHODS FOR MAKING AND USING THEM

(71) Applicants: The Regents of the University of California, Oakland, CA (US); The Scripps Research Institute, La Jolla, CA (US)

(72) Inventors: Palmer Taylor, La Jolla, CA (US); Zoran Radic, La Jolla, CA (US); Karl Barry Sharpless, La Jolla, CA (US); Valery Fokin, La Jolla, CA (US); Rakesh Sit, La Jolla, CA (US)

(73) Assignees: THE REGENTS OF THE UNIVERSITY OF CALIFORNIA, Oakland, CA (US); THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/029,267

(22) Filed: Jul. 6, 2018

(65) Prior Publication Data
US 2019/0119237 A1    Apr. 25, 2019

Related U.S. Application Data

(63) Continuation of application No. 14/766,272, filed as application No. PCT/US2014/016639 on Feb. 15, 2014, now abandoned.

(60) Provisional application No. 61/765,596, filed on Feb. 15, 2013.

(51) Int. Cl.
| | | |
|---|---|---|
| C07D 295/13 | (2006.01) |
| C07D 221/22 | (2006.01) |
| C07D 223/04 | (2006.01) |
| C07D 451/02 | (2006.01) |
| C07D 471/08 | (2006.01) |
| C07D 209/56 | (2006.01) |
| A61K 31/55 | (2006.01) |
| C07D 223/06 | (2006.01) |
| C07D 451/14 | (2006.01) |
| C07D 487/08 | (2006.01) |

(52) U.S. Cl.
CPC ............ *C07D 295/13* (2013.01); *A61K 31/55* (2013.01); *C07D 209/56* (2013.01); *C07D 221/22* (2013.01); *C07D 223/04* (2013.01); *C07D 223/06* (2013.01); *C07D 451/02* (2013.01); *C07D 451/14* (2013.01); *C07D 471/08* (2013.01); *C07D 487/08* (2013.01)

(58) Field of Classification Search
CPC .............................. A61K 31/55; C07D 295/13
See application file for complete search history.

(56) References Cited

PUBLICATIONS

English translation of Somin et al., "Zhurnal Organicheskoi Khimii," (1977), v 13, n 5, p. 910-918.
Radic et al., "Refinement of structural leads for centrally acting oxime reactivators of phosphylated cholinesterases" the Journal of Biological Chemistry, 2012, v 287, n 15, p. 11798-11809.
Sit et al., "New structural scaffolds for centrally acting oxime reactivators of phosphylated cholinesterases" The Journal of Biological Chemistry, 2011, v 286, n 22, p. 19422-19430.

*Primary Examiner* — Alicia L Otton
(74) *Attorney, Agent, or Firm* — Greer, Burns & Crain, Ltd.; Gregory P. Einhom

(57) ABSTRACT

In alternative embodiments, the invention provides nucleophilic hydroxyimino-acetamido alkylamine antidotes that cross the blood-brain barrier (BBB) to catalyze the hydrolysis of organophosphate (OP)-inhibited human acetylcholinesterase (hAChE) in the central nerve system (CNS). The hydroxyimino-acetamido alkylamines of the invention are designed to fit within AChE active center gorge dimensions, bind with reasonable affinity, and react with the conjugated phosphate atom in the gorge. The hydroxyimino-acetamido alkylamines of the invention are also designed to possess ionization states that govern affinity and reactivity for the two linked hAChE re-activation steps. In alternative embodiments, the invention provides pumps, devices, subcutaneous infusion devices, continuous subcutaneous infusion devices, infusion pens, needles, reservoirs, ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector, comprising a compound of the invention.

22 Claims, 50 Drawing Sheets

Table 1

| Oxime | Oxime structure | $k_{obs}$ (relative to 2PAM)* | | | | | Oximolysis (d/min) | % Oximate @ pH 7.4 | % Neutral @ pH 7.4 | R Volume (Å³) | R Area (Å²) |
|---|---|---|---|---|---|---|---|---|---|---|---|
| | | Ave | POX | Sarin | CS | VX | | | | | |
| RS2-31B | | 1.1 | 0.24 | 0.85 | 2.4 | 0.95 | 0.099 | 0.25 | 4.4 | 299 | 324 |
| RS189A | | 1.4 | 0.11 | 1.0 | 2.6 | 1.7 | 0.124 | 0.21 | 2.6 | 186 | 180 |
| RS2-57B | | 0.16 | 0.084 | 0.11 | 0.19 | 0.26 | 0.181 | 0.23 | 0.17 | 161 | 173 |
| RS218A | | 0.91 | 0.23 | 1.3 | 1.5 | 0.80 | 0.128 | 0.35 | 1.0 | 196 | 199 |
| RS251B | | 0.82 | 0.34 | 1.0 | 1.2 | 0.74 | 0.074 | 0.13 | 0.31 | 173 | 188 |
| RS251A | | 0.55 | 0.11 | 0.69 | 0.83 | 0.56 | 0.108 | 0.26 | 2.3 | 156 | 170 |
| RS194C | | 0.58 | 0.37 | 0.88 | 0.39 | 0.68 | 0.120 | 0.30 | 0.49 | 157 | 174 |
| RS194B | | 2.5 | 0.53 | 3.1 | 3.6 | 2.7 | 0.128 | 0.25 | 3.5 | 139 | 156 |
| RS191E | | 2.0 | 0.39 | 1.6 | 3.5 | 2.7 | 0.136 | 0.30 | 1.4 | 140 | 161 |
| RS69N | | 0.53 | 0.200 | 0.450 | 0.500 | 1.0 | 0.135 | 0.22 | 9.5 | 123 | 143 |
| RS69L | | 0.55 | 0.16 | 0.80 | 0.24 | 1.0 | 0.119 | 0.30 | 1.0 | 124 | 148 |
| RS41A | | 0.88 | 0.10 | 1.0 | 1.3 | 1.1 | 0.109 | 0.20 | 7.0 | 107 | 130 |
| RS41B | | 0.26 | 0.073 | 0.21 | 0.20 | 0.56 | 0.127 | 0.21 | 7.0 | 83 | 107 |
| RS160C | | 0.091 | 0.052 | 0.030 | 0.18 | 0.10 | 0.117 | 0.27 | 0.40 | 69 | 94 |
| RS157B | | 0.010 | 0.010 | 0.010 | 0.010 | 0.010 | 0.078 | 0.41 | 1.7 | 52 | 76 |
| RS157A | | 0.010 | 0.010 | 0.010 | 0.010 | 0.010 | 0.128 | 0.5 | 99.5 | 19 | 37 |

FIG. 3

Table 2

| Oxime | Oxime structure | Paraoxon $k_2$ | Paraoxon $K_{ox}$ | Paraoxon $k_r$ | Sarin $k_2$ | Sarin $K_{ox}$ | Sarin $k_r$ | Cyclosarin $k_2$ | Cyclosarin $K_{ox}$ | Cyclosarin $k_r$ | VX $k_2$ | VX $K_{ox}$ | VX $k_r$ | Tabun $k_2$ | Tabun $K_{ox}$ | Tabun $k_r$ |
|---|---|---|---|---|---|---|---|---|---|---|---|---|---|---|---|---|
| RS194B | | 0.38 | 7.4 | 51 | 2.5 | 1.9 | 1300 | 0.88 | 3.9 | 230 | 3.1 | 2.1 | 16000 | 0.0018 | 1.8 | 1.9 |
| RS194C | | 0.11 | 2.9 | 38 | 1.5 | 1.1 | 1400 | 0.90 | 4.3 | 210 | 1.9 | 2.4 | 790 | n.d. | n.d. | n.d. |
| RS69N | | >0.7 | >50 | 13 | 2.2 | 2.2 | 1000 | 1.4 | 9.4 | 150 | 2.7 | 3.0 | 900 | n.d. | n.d. | n.d. |
| RS218A | | 0.16 | 2.2 | 73 | 0.84 | 0.83 | 1000 | 0.53 | 5.4 | 98 | 1.3 | 2.2 | 590 | n.d. | n.d. | n.d. |
| RS69L | | 0.08 | 3.0 | 27 | 1.8 | 1.9 | 950 | 1.1 | 10 | 110 | 3.4 | 7.9 | 430 | n.d. | n.d. | n.d. |
| RS41A | | 0.15 | 4.3 | 35 | 3.7 | 11 | 340 | 1.9 | 21 | 90 | 3.1 | 4.6 | 670 | 0.00082 | 3.6 | 0.22 |
| RS191E | | 0.048 | 2.0 | 24 | 1.3 | 2.2 | 590 | 0.72 | 4.4 | 160 | 1.4 | 5.8 | 240 | n.d. | n.d. | n.d. |
| RS186B | | 0.31 | 9.1 | 39 | 0.84 | 7.8 | 110 | 0.72 | 15 | 48 | 0.36 | 2.7 | 130 | n.d. | n.d. | n.d. |
| MINA | | >0.20 | >30 | 8.4 | 1.6 | 14 | 120 | 1.2 | 16 | 75 | >0.7 | >6.0 | 110 | - | - | 0.039 |
| DAM | | 0.027 | 4.6 | 0.58 | 0.13 | 88 | 1.5 | >0.30 | >100 | 2.5 | 0.20 | >100 | 1.7 | - | - | 0.0038 |
| 2PAM | | 0.27 | 1.8 | 150 | 1.1 | 0.34 | 3200 | 0.73 | 6.6 | 110 | 0.63 | 0.25 | 2600 | 0.0058 | 1.5 | 3.8 |

FIG. 4

Table 3

Constants were calculated by nonlinear regression using Equation 1. ND, not determined.

| Oxime | Oxime p$K_a$ | | | | Average p$K_a$ |
|---|---|---|---|---|---|
| | UV spectra | ATCh | VX Flu-MP | | |
| | | Oximolysis | | | |
| RS194B | 8.8 ± 0.2 | 9.1 ± 0.1 (-OH) | 9.0 ± 0.1 | 8.9 ± 0.1 | 8.8 (-OH) |
| | | 9.3 ± 0.1 (NH$^+$)[b] | | | 8.8 (NH$^+$) |
| | | 9.2 ± 0.1 (NH$^+$)[c] | | | |
| RS41A | 8.8 ± 0.1 | ND | 9.0 ± 0.1 | 8.7 ± 0.1 | 8.8 |
| RS186B | 8.3 ± 0.1 | ND | 8.5 ± 0.1 | ND | 8.4 |
| RS150D | ND | ND | 10.1 ± 0.1 | ND | 10.1 |
| RS174C | ND | ND | 6.5 ± 0.1 | ND | 6.5 |
| MINA | 8.3 ± 0.1 | ND | 8.7 ± 0.1 | ND | 8.5 |
| 2PAM | ND | 8.6 ± 0.1 (-OH) | 8.0 ± 0.1 | 8.1 ± 0.2 | 8.1 |

[a] p$K_a$ values determined in D$_2$O, as shown, are typically higher than those determined in H$_2$O by ⁓0.5 (27) and were corrected before calculating the average p$K_a$.
[b] Based on pH induced shift of 3.37 ppm triplet in D$_2$O (Figs. 3B and supplemental S1).
[c] Based on pH induced shift of 3.73 ppm triplet in D$_2$O (Figs. 3C and supplemental S1).

FIG. 12

TABLE 4

Kinetic constants for reactivation of VX-hAChE conjugate by oximes RS194B, RS41A, RS186B, and reference oxime 2PAM determined in 0.1 M phosphate buffers pH 6.4, 7.4, and 8.4

| Oxime | pH | $k_2$ | $K_{ox}$ | $k_r$ |
|---|---|---|---|---|
| | | $min^{-1}$ | mM | $M^{-1}\ min^{-1}$ |
| RS194B | 6.4 | 2.1 ± 0.2 | 3.2 ± 1.0 | 620 ± 130 |
| | 7.4 | 3.1 ± 0.1 | 2.1 ± 0.3 | 1600 ± 130 |
| | 8.4 | 3.3 ± 0.3 | 4.2 ± 1.0 | 790 ± 120 |
| RS41A | 6.4 | 1.4 ± 0.2 | 3.3 ± 1.4 | 410 ± 110 |
| | 7.4 | 3.1 ± 0.3 | 4.6 ± 0.9 | 670 ± 80 |
| | 8.4 | 3.5 ± 0.3 | 2.5 ± 0.6 | 1400 ± 210 |
| 2PAM | 6.4 | 0.25 ± 0.01 | 0.091 ± 0.028 | 2800 ± 780 |
| | 7.4 | 0.65 ± 0.08 | 0.25 ± 0.12 | 2600 ± 910 |
| | 8.4 | 0.80 ± 0.04 | 0.36 ± 0.08 | 2200 ± 390 |
| RS186B | 6.4 | 0.23 ± 0.01 | 3.6 ± 0.7 | 63 ± 10 |
| | 7.4 | 0.36 ± 0.02 | 2.7 ± 0.4 | 130 ± 18 |
| | 8.4 | 0.35 ± 0.02 | 3.5 ± 0.6 | 99 ± 15 |

FIG. 13

TABLE 5
Therapy of OP-exposed mice with lead oximes RS194B and RS41A and standard reference oxime 2PAM. Protective index is the ratio of OP LD$_{50}$ for OP-exposed animals treated with oxime (+atropine) and for animals given OP alone (cf. supplemental Tables S2–S6) 95% confidence limits are given in parentheses. ND, not determined.

| Oxime | LD$_{50}$ mg/kg | Dose mg/kg | Protective index | | | | |
|---|---|---|---|---|---|---|---|
| | | | VX | Sarin | Paraoxon | Soman | Tabun |
| RS41A | 200 (160.9–248.8) | 50 | 4.5 (3.8–5.3) | 1 (ND) | 1 (ND) | 1.3 (1.1–1.5) | 1.2 (1.0–1.4) |
| RS194B | 500$^a$ | 125 | 18 (12.4–25.7) | 10 (6.6–15.3) | 9.4 (7.9–11.3) | 1.8 (1.5–2.1) | 1.5 (1.2–1.7) |
| 2PAM | 106 (94.0–118.4) | 26.4 | 9.3 (7.3–13.0) | 6.7 (5.9–7.5) | 47 (36.7–59.5) | 1.5 (1.3–1.8) | 1.3 (1.1–1.5) |

$^a$ Estimated from 50% lethality at the maximal administered dose due to solubility limitations.

FIG. 14

TABLE 6

Combination of therapy and pretreatment of OP-exposed mice with oxime RS194B at doses equivalent to 25, 10, or 5% its $LD_{50}$ dose of 500 mg/kg (cf. supplemental Tables S2–S6)

Protective index is the ratio of OP $LD_{50}$ for OP-exposed animals treated with oxime and for animals given OP alone. Maximal dose of poison (MDP), a highest multiple of OP $LD_{50}$ fully counteracted by the oxime, is given in parentheses. Oximes in therapy (but not in pretreatment) were administered together with atropine. ND, not determined.

Protective index (MDP) (95% confidence limits)

| RS194B | Pretreatment before VX | | Therapy 1 min after VX | Pretreatment 15 min and therapy 1 min after VX |
|---|---|---|---|---|
| | 5 min | 15 min | | |
| 25 mg/kg | 2.0 (1.6) (1.8–2.3) | 1.6 (ND) (1.2–2.1) | 5.3 (4) (4.8–6.0) | |
| 50 mg/kg | | 1.3 (1.0) (1.1–1.6) | 11 (7.9) (8.5–13.7) | 7.3 (5.0) (5.6–9.6) |
| 125 mg/kg | 3.7 (2.5) (2.9–4.7) | 3.6 (2.5) (3.0–4.2) | 18 (10.0) (12.4–25.7) | 45 (31.8) (37.2–54.3) |

Pretreatment 15 min and therapy 1 min after OP

| | Paraoxon | Soman | Tabun | Sarin |
|---|---|---|---|---|
| 125 mg/kg | 22 (7.9) (17.0–27.5) | 2.8 (2.5) (ND) | 2.0 (ND) (1.3–3.1) | 4.5 (3.2) (3.8–5.3) |

FIG. 15 intravenous

| Dose (mg/kg) | $t_{1/2}$ (hr) | $C_{max}$ Mean (ng/ml) | $C_0$ (ng/ml) | $AUC_{last}$ (hr·ng/ml) Mean | $AUC_{inf}$ (hr·ng/ml) |
|---|---|---|---|---|---|
| 20 | 0.9728 | 3457 | 6212 | 1270 | 1274 | oral

| Dose (mg/kg) | $t_{1/2}$ (hr) | $T_{max}$ (hr) | $C_{max}$ Mean (ng/ml) | $AUC_{last}$ (hr·ng/ml) Mean | $AUC_{inf}$ (hr·ng/ml) Mean | F (%) |
|---|---|---|---|---|---|---|
| 50 | 1.2 | 0.25 | 3693 | 2149 | 2175 | 68.3 |
| 200 | 1.2 | 0.167 | 20540 | 12391 | 12484 | 98.0 |

FIG. 17

| oxime | paraoxon | | | sarin | | | Cyclosarin | | | VX | | |
|---|---|---|---|---|---|---|---|---|---|---|---|---|
| | $k_2$ (min$^{-1}$) | $K_{ox}$ (mM) | $k_r$ (M$^{-1}$ min$^{-1}$) | $k_2$ (min$^{-1}$) | $K_{ox}$ (mM) | $k_r$ (M$^{-1}$ min$^{-1}$) | $k_2$ (min$^{-1}$) | $K_{ox}$ (mM) | $k_r$ (M$^{-1}$ min$^{-1}$) | $k_2$ (min$^{-1}$) | $K_{ox}$ (mM) | $k_r$ (M$^{-1}$ min$^{-1}$) |
| RS 194B | 0.38 | 7.4 | 51 | 2.5 | 1.9 | 1300 | 0.88 | 3.9 | 230 | 2.8 | 1.6 | 1800 |
| RS 21388 | 0.23 | 2.2 | 100 | 2.4 | 1.2 | 2000 | 0.83 | 6.8 | 120 | 2.6 | 1.6 | 1600 |
| MINA | >0.20 | >20 | 8.4 | 1.6 | 14 | 120 | 1.2 | 16 | 75 | >0.7 | >6.0 | 110 |
| DAM | 0.027 | 46 | 0.58 | 0.13 | 88 | 1.5 | >0.30 | >100 | 2.5 | 0.20 | >100 | 1.7 |
| 2PAM | 0.27 | 1.8 | 150 | 1.1 | 0.34 | 3200 | 0.73 | 6.6 | 110 | 0.73 | 0.3 | 2400 |

FIG. 19

RS2 138B
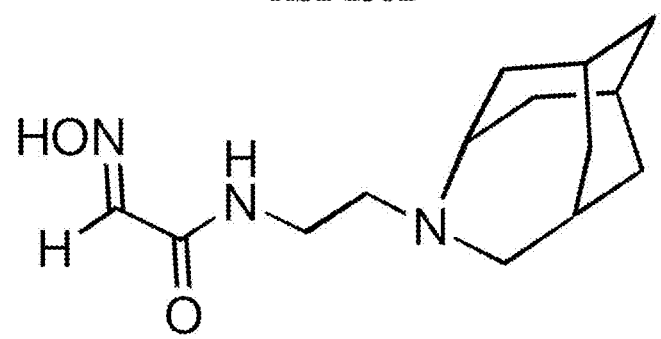
RS 194B
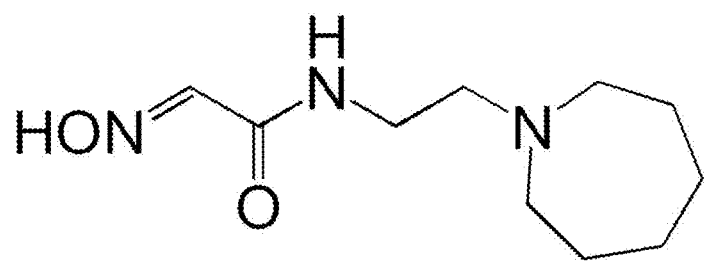
FIG. 21

Summary of rates of ATCh (1.0 mM) oximolysis by oximes (1.0 mM) and average reactivation rates of OP (VX, sarin, cyclosarin and paraoxon) conjugated hAChE measured in 0.1 mM phosphate buffer pH 7.4 at 22°C (oximolysis) or 37°C (reactivation). Given $pK_a$ values were evaluated from pH dependence of ATCh oximolysis shown in the figure.

| oxime | $pK_a$ | ATCh oximolysis at pH 7.4 (dA/min) | average OP-hAChE reactivation (fraction of 2PAM) |
|---|---|---|---|
| RS150D | 10 | 0.023 | 0.5 |
| RS194B | 9.0 | 0.128 | 3.9 |
| RS41A | 9.0 | 0.109 | 0.9 |
| RS186B | 8.5 | 0.201 | 0.7 |
| MINA | 8.7 | 0.126 | 0.2 |
| 2PAM | 8.0 | 0.157 | 1.0 |
| RS174C | 6.5 | 0.440 | 0.0 |

| oxime | i.m. dose (mg/kg) | [oxime]$_{max}$ (μg/ml) | | [oxime]$_{max}$ (μM) | | | time for ([oxime]$_{max}$)/2 (min) | | | log D |
|---|---|---|---|---|---|---|---|---|---|---|
| | | brain | plasma | brain | plasma | brain/plasma | brain | plasma | brain/plasma | |
| RS41A | 30 | 1.2 | 10 | 6.5 | 54 | 0.12 | 30 | 11 | 1.7 | -1.09 |
| RS194B | 80 | 7.9 | 27 | 37 | 125 | 0.30 | 62 | 12 | 4.2 | -0.48 |

FIG. 28

Table S2

| VX | | Therapy 1 min after exposure | | | | Pretreatment 15 min before VX & Therapy 1 min after exposure | |
|---|---|---|---|---|---|---|---|
| | | RS41A | | RS194B | | R194B | |
| $LD_{50}$ | (µg/kg) | Survived/ treated | Symptoms | Survived / | Symptoms | Survived/ treated | Symptoms |
| 3.18 | 90.0 | 4 / 4 | Mice were hypoactive; no symptoms. | 4 / 4 | No visible symptoms. | | |
| 4.0 | 113.2 | 3 / 4 | Strong tremor immediately upon application; respiratory disturbance; three mice recovered fully after 1 h. | 4 / 4 | No visible symptoms. | | |
| 5.0 | 141.5 | 1 / 4 | Strong tremor immediately upon application; respiratory disturbance; light salivation; surviving mouse weak after 24h. | 4 / 4 | No visible symptoms. | | |
| 6.3 | 178.3 | 0 / 4 | Strong tremor and salivation immediately upon application. | - | - | | |
| 7.9 | 223.6 | 1 / 4 | Strong tremor immediately upon application. Surviving mouse weak after 24h. | - | - | | |
| 10.0 | 283.0 | 2 / 4 | Strong tremor immediately upon application. Surviving mouse weak after 24h. | 4 / 4 | Light tremor 10 min upon application. All symptoms disappeared after 1 h. | | |
| 12.6 | 356.6 | 0 / 4 | Strong tremor and respiratory disturbance immediately upon application. | 3 / 4 | Strong tremor 2 min upon application, respiratory disturbance. Surviving mice recovered fully after 24h. | | |
| 15.9 | 450.0 | 0 / 4 | Strong tremor and respiratory disturbance immediately upon application | 3 / 4 | Strong tremor immediately upon application, respiratory disturbance, salivation. Surviving mice recovered fully after 24h. | | |
| 20.0 | 566.0 | | | 1 / 4 | Strong tremor immediately upon application, salivation. Surviving mouse weak but active after 24h. | 4 / 4 | Mice hypoactive 5 min upon application. All symptoms disappeared after 30 min. |
| 25.2 | 713.2 | | | 1 / 4 | Strong tremor immediately upon application, salivation. Surviving mouse weak after 24h. | 1 / 4 | Strong tremor 2min upon application, respiratory disturbance, surviving mouse active after 24h. |
| 31.8 | 899.9 | | | | | 4 / 4 | Strong tremor 2min upon application, respiratory disturbance, surviving mice active after 24h. |
| 40.0 | 1132 | | | | | 2 / 4 | Strong tremor 2min upon application. Surviving mice weak after 24h. |
| 50.4 | 1426.3 | | | | | 2 / 4 | Strong tremor immediately upon application, respiratory disturbance, salivation, surviving mice weak after 24h. |
| 63.0 | 1785.2 | | | | | 0 / 4 | Strong tremor immediately upon application, respiratory disturbance, salivation. |
| $LD_{50}$<br>PI<br>MDP | | 127.3 µg/kg<br>4.5 (3.8 - 5.3)<br>3.18 | | 504.4 µg/kg<br>17.8 (12.7 - 25.7)<br>10 | | 1272.9 µg/kg<br>45 (37.2 – 54.3)<br>31.8 | |

FIG. 29

Table S3

| Sarin | | Therapy 1 min after exposure | | | | Pretreatment 15 min before sarin & Therapy 1 min after exposure | |
|---|---|---|---|---|---|---|---|
| | | RS41A | | RS194B | | RS194B | |
| (μg/kg) | LD₅₀ | Survived/treated | Symptoms | Survived/treated | Symptoms | Survived/treated | Symptoms |
| 757.8 | 3.18 | 0 / 4 | Mild but persistent tremor 10 min upon application. | - | | 4 / 4 | Strong tremor immediately upon application. All mice quickly and fully recovered after 24 h. |
| 953.2 | 4.0 | | | 4 / 4 | No visible symptoms. | 3 / 4 | Strong tremor immediately upon application. Surviving mice completely recovered after 24 h. |
| 1191.5 | 5.0 | | | 2 / 4 | Strong tremor immediately upon application, convulsions, surviving mice recovered after 24 h. | 1 / 4 | Strong tremor immediately upon application, convulsions, surviving mouse weak but active after 24 h. |
| 1501.3 | 6.3 | | | 3 / 4 | Strong tremor 1min upon application, convulsions, surviving mice recovered after 24 h. | 0 / 4 | Strong tremor immediately upon application. |
| 1882.6 | 7.9 | | | 3 / 4 | Strong tremor immediately upon application, convulsions, surviving mice recovered after 24 h. | 2 / 4 | Strong tremor immediately upon application, convulsions, surviving mice weak after 24 h. |
| 2383.0 | 10.0 | | | 2 / 4 | Strong tremor immediately upon application, convulsions, surviving mice recovered after 24 h. | 2 / 4 | Strong tremor immediately upon application, convulsions, surviving mice weak after 24 h. |
| 3002.6 | 12.6 | | | 1 / 4 | Strong tremor immediately upon application, convulsions, surviving mouse recovered after 24 h. | - | |
| LD₅₀ | | - | | 2384 μg/kg | | 1072 μg/kg | |
| PI | | - | | 10 (6.6 – 15.3) | | 4.5 (3.8 – 5.3) | |
| MDP | | - | | 4 | | 3.18 | |

FIG. 30

Table S4

| Tabun | | Therapy 1 min after exposure | | | | Pretreatment 15 min before tabun & Therapy 1 min after exposure | |
|---|---|---|---|---|---|---|---|
| | | RS41A | | RS194B | | RS194B | |
| $LD_{50}$ | (µg/kg) | Survived/ treated | Symptoms | Survived/ treated | Symptoms | Survived/ treated | Symptoms |
| 0.79 | 449.0 | 4 / 4 | No visible symptoms. | - | | | |
| 1.0 | 555.8 | 3 / 4 | Mild but persistent increasing tremor upon application. Surviving mice recovered completely after 1h. | 3 / 4 | Mild increasing tremor upon application. Surviving mice recovered after 24h. | | |
| 1.26 | 712.9 | 2 / 4 | Strong tremor immediately upon application. Surviving mice recovered completely after 24h. | 4 / 4 | Slight tremor only. All mice recovered. | | |
| 1.59 | 899.6 | 0 / 4 | Strong tremor immediately upon application. | 1 / 4 | Tremor immediately upon application, respiratory disturbance, surviving mouse weak after 24h. | 3 / 4 | Mild but persistent increasing tremor upon application. Surviving mice recovered completely after 24h. |
| 2.0 | 1131.6 | | | 0 / 4 | Strong tremor immediately upon application. | 1 / 4 | Strong tremor immediately upon application, convulsions, surviving mouse recovered after 24h. |
| 2.52 | 1425.8 | | | | | 2 / 4 | Strong tremor immediately upon application, convulsions, surviving mice active after 24h. |
| 3.18 | 1799.2 | | | | | 1 / 4 | Strong tremor immediately upon application, convulsions, surviving mouse weak after 24h. |
| $LD_{50}$ | | 672.8 | | 831.8 µg/kg | | 1133.4 µg/kg | |
| PI | | 1.2 (1.0 – 1.4) | | 1.5 (1.2 – 1.7) | | 2.0 (1.3 – 3.1) | |
| MDP | | 0.79 | | 1.26 | | **/** | |

FIG. 31

Table S5 part I

| Table S5 | | | | | |
|---|---|---|---|---|---|
| | | Therapy 1 min after exposure | | Pretreatment 15 min before paraoxon & Therapy 1 min after exposure | |
| Paraoxon | | RS41A | RS194B | RS194B | |
| LD$_{50}$ | (µg/kg) | Surviv | Symptoms | Surviv | Symptoms | Surviv | Symptoms |
| 1.0 | 712.9 | 0 / 4 | Strong motor irritation immediately upon application. | | | | |
| 4.0 | 2851.6 | | | 4 / 4 | Mild symptoms upon application. Mice recovered fully after 10 min. | | |
| 5.0 | 3564.5 | | | 2 / 4 | Mild increasing tremor upon application. Surviving mice recovered after 40 min. | | |
| 6.3 | 4491.3 | | | 4 / 4 | Strong tremor immediately upon application, salivation, all mice recovered after 60 min. | | |
| 7.9 | 5631.9 | | | 3 / 4 | Strong tremor immediately upon application, salvation, respiratory disturbance, surviving mice recovered after 2 h. | 4 / 4 | No visible symptoms. |
| 10.0 | 7129.0 | | | 2 / 4 | Strong tremor immediately upon application, salvation, surviving mice recovered after 24 h. | 3 / 4 | Mild tremor upon application. Surviving mice recovered completely after 24h. |

FIG. 32

Table S5 part II

| | | | |
|---|---|---|---|
| 12.6 | 8982.5 | 0 / 4 | Strong tremor immediately upon application, salvation, respiratory disturbance. |
| | | 2 / 4 | Increasing tremor immediately upon application. Surviving mice recovered after 24 h. |
| 15.9 | 11335 | 1 / 4 | Strong tremor immediately upon application, salivation, surviving mouse weak after 24 h. |
| | | 3 / 4 | Strong tremor immediately upon application, repiratory distrurance, surviving mice weak after 24 h. |
| 20.0 | 14816 | | Strong or increasing tremor immediately upon application, respiratory disturbance, surviving mice weak after 24 h. |
| | | 3 / 4 | |
| 25.2 | 18668 | | Strong tremor immediately upon application, respiratory disturbance, surviving mouse weak after 24 h |
| | | 1 / 4 | |
| 31.8 | 23557 | 0 / 4 | Strong tremor immediately upon application. |
| $LD_{50}$ | - | 6731.3 µg/kg | 16032.5 µg/kg |
| PI | - | 9.4 (7.9 – 11.3) | 21.6 (17.0 – 27.5) |
| MDP | - | 6.3 | 7.9 |

FIG. 33

| Table S6 | | | | | | |
|---|---|---|---|---|---|---|
| Soman | Therapy 1 min after exposure | | | | Pretreatment 15 min before soman & Therapy 1 min after exposure | |
| | RS41A | | RS194B | | RS194B | |
| (µg/kg) | Survived/treated | Symptoms | Survived/treated | Symptoms | Survived/treated | Symptoms |
| LD₅₀ | | | | | | |
| 1.0 / 136.1 | 4/4 | Mice hypoactive upon application. | | | | |
| 1.26 / 171.5 | 1/4 | Increasing tremor and convulsions immediately upon application. Surviving mouse was weak but active after 24 h. | 4/4 | Mice hypoactive upon application. All mice recovered after 24 h. | | |
| 1.59 / 216.4 | 1/4 | Increasing tremor and convulsions immediately upon application. Surviving mouse was weak and hypoactive after 24 h. | 4/4 | Mice hypoactive upon application, diarrhea, all mice recovered after 24 h. | 3/4 | Mice were hypoactive upon application occasionally having light tremor. Surviving mouse weak after 24 h. |
| 2.0 / 272.2 | 0/4 | Strong tremor immediately upon application. | 3/4 | Mice hypoactive with increasing tremor upon application, diarrhea, motor coordination disturbance, surviving mice recovered after 24 h. | 3/4 | Mice hypoactive with increasing tremor upon application. Surviving mice weak but active after 24 h. |
| 2.52 / 342.9 | | | 1/4 | Mice hypoactive with increasing tremor upon application, diarrhea, motor coordination disturbance, surviving mouse weak after 24 h. | 4/4 | Mice weak with occasional tremor upon application. All mice weak after 24 h. |
| 3.18 / 432.8 | | | 0/4 | Increasing tremor immediately upon application, diarrhea. | 4/4 | Mice weak with occasional tremor upon application. All mice weak but active after 24 h. |
| 4.0 / 544.4 | | | | | 0/4 | Strong tremor immediately upon application, convulsions, respiratory disturbance. |
| | | | | | 0/4 | Strong tremor immediately upon application, convulsions. |
| LD₅₀ | 171.5 | | 242.6 µg/kg | | 385 µg/kg | |
| PI | 1.26 (1.1 – 1.5) | | 1.8 (1.5 – 2.1) | | 2.8 (−) | |
| MDP | 1.0 | | 1.26 | | 2.52 | |

FIG. 34

CENTRALLY ACTIVE AND ORALLY BIOAVAILABLE ANTIDOTES FOR ORGANOPHOSPHATE EXPOSURE AND METHODS FOR MAKING AND USING THEM

RELATED APPLICATIONS

This application claims the benefit of priority to U.S. Provisional Patent application Ser. No. 61/765,596, filed Feb. 15, 2013. The aforementioned application is expressly incorporated herein by reference in its entirety and for all purposes.

STATEMENT AS TO RIGHTS TO INVENTIONS MADE UNDER FEDERALLY SPONSORED RESEARCH

This invention was made with government support under grant no. U01NS058046, awarded by the National Institutes of Health (NIH), DHHS. The government has certain rights in the invention.

TECHNICAL FIELD

This invention relates to antidote chemistry for organophosphates and their detoxification. In alternative embodiments, the invention provides nucleophilic hydroxyimino-acetamido alkylamine antidotes that cross the blood-brain barrier (BBB) to catalyze the hydrolysis of organophosphate (OP)-inhibited human acetylcholinesterase (hAChE) in the central nerve system (CNS). The hydroxyimino-acetamido alkylamines of the invention are designed to fit within AChE active center gorge dimensions, bind with reasonable affinity, and react with the conjugated phosphate atom in the gorge. The hydroxyimino-acetamido alkylamines of the invention are also designed to possess ionization states that govern affinity and reactivity for the two linked hAChE re-activation steps.

BACKGROUND

A recent spur of interest in centrally acting reactivators of organophosphate (OP)" inhibited acetylcholinesterase (AChE) reflects a compelling need for antidotal therapy capable of efficient reinstatement of CNS AChE activity in OP-intoxicated individuals. Exposure to uncharged, lipophilic OPs from both pesticide and nerve agents leads to inhibition of peripheral and CNS AChE within minutes of exposure due to rapid OP distribution through the various body compartments of exposed individuals. However, attention has been accorded primarily to the development of re-activator antidotes with an ionizable cationic site since quaternary ammonium ligands have a clear preference for association with predominantly aromatic active center gorge of AChE. When administered in vivo, quaternary oxime reactivators largely remain in blood and peripheral tissues incapable of crossing the blood-brain barrier and reactivating OP-inhibited brain AChE.

The organophosphate antidote 2-PAM, designed by Irwin Wilson in the 1950's, remains as a staple antidote for nerve agent and insecticide poisoning to this day. The compound is limited by three factors: its quaternary ammonium moiety prevents the compound from crossing the blood-brain barrier, so 2-PAM does not reactivate CNS acetylcholinesterase; the quaternary change precludes rapid absorption following oral administration requiring parenteral administration, and the volume occupied by the pyridinium aldoxime moiety precludes it attacking the covalently linked phosphate with an optimal attack angle.

SUMMARY

In alternative embodiments, the invention provides compounds having one of the following structures or compositions having one or more compounds of the following structures, or equivalents thereof, or a stereoisomer thereof, or an analog thereof, or a pharmaceutically acceptable salt thereof, or a bioisostere thereof; or, the invention provides a composition comprising an isolated compound consisting essentially of, or consisting of:

(a) a compound having the formula:

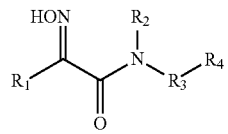

wherein:
$R_1$ is selected from the group consisting of: —H, -alkyl, and -aryl;
$R_2$ is selected from the group consisting of: —H, -alkyl, and -aryl;
$R_3$ is selected from the group consisting of: —$(CH_2)_n$—, and $(CH_2)_n$—$CH(CH_3)$— wherein n is the integer 0, 1, 2, 3, 4 or 5;
$R_4$ is selected from the group consisting of: —H, -alkyl (wherein optionally the alkyl is selected from the group consisting of: -methyl, -ethyl, -propyl, -butyl, -i-propyl, and i-butyl), -cycloalkyl (wherein optionally the cycloalkyl is selected from the group consisting of: -cyclopropyl, -cyclobutyl, -cyclopentyl, -cyclohexyl, -cycloheptyl, and -cyclooctyl), -aryl (wherein optionally the aryl is selected from the group consisting of: -phenyl, -naphthyl, -thienyl, and -indolyl), -saturated and nonsaturated heterocyclics (wherein optionally the saturated or nonsaturated heterocyclic is selected from the group consisting of: -aziridine, -oxirane-thiirane, -azirine, -oxirene, -thiirene, -azetidine, -oxetane -thietane, -mete, -oxete, -thiete, -pyrrolidine, -oxolane -thiolane, -pyrrole, -furan, -thiophene, -piperidine, -oxane, -thiane, -pyridine, -pyran, -thiopyran azepane, -oxepane, -thiepane -azepine -oxepine, -thiepine, -azocane and -azocine), and bridged compounds (wherein optionally the bridged compound is selected from the group consisting of: -adamantanes, -amantadines, -biperidenes, -memantines, -methenamines, -rimantadines, -norbornanes, and -triazoles);

(b) a compound having the formula:

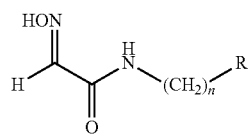

wherein
N is the integer 0, 1, 2, 3, 4 or s;
R is selected from the group consisting of: —H, -alkyl (wherein optionally the alkyl is selected from the group consisting of: -methyl, -ethyl, -propyl, -butyl, -i-propyl, and -i-butyl), -cycloalkyl (wherein optionally the cycloalkyl is selected from the group consisting of: -cyclopropyl, -cyclobutyl, -cyclopentyl, -cyclohexyl, -cycloheptyl, and -cyclooctyl), -aryl (wherein optionally the aryl is selected from the group consisting of: -phenyl, -naphthyl, -thienyl, and -indolyl), -saturated and nonsaturated heterocyclics (wherein optionally the saturated or nonsaturated heterocyclic is selected from the group consisting of: -aziridine, -oxirane-thiirane, -azirine, -oxirene, -thiirene, -azetidine, -oxetane, -thietane, -azete, -oxete, -thiete, -pyrrolidine, oxolane, -thiolane, -pyrrole, -furan, -thiophene, -piperidine, -oxane, -thiane, -pyridine, -pyran, -thiopyran, azepane, -oxepane, -thiepane, -azepine, -oxepine, -thiepine, -azocane, and -azocine), and bridged compounds (wherein optionally the bridged compound is selected from the group consisting of: -adamantanes, -amantadines, -biperidenes, -memantines, -methenamines, -rimantadines, -norbornanes, and -triazoles);

(d) a compound having the formula:

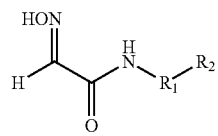

wherein $R_1$ is selected from the group consisting of: —$(CH_2)_n$—, and $(CH_2)_n$—$CH(CH_3)$— wherein N is the integer 0, 1, 2, 3, 4 or 5;

$R_2$ is selected from the group consisting of:

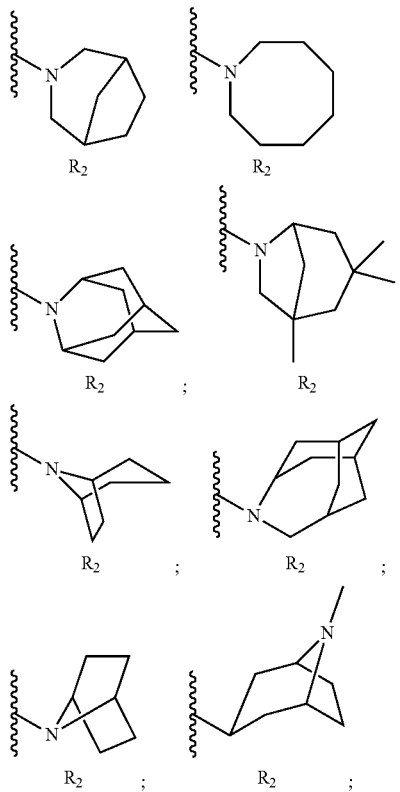

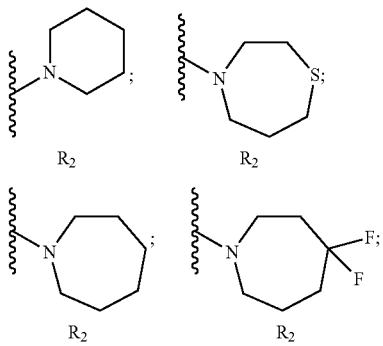

and any combination thereof);

(e) a compound having the formula:

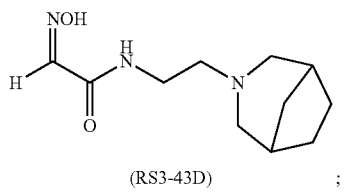

(RS3-43D) ;

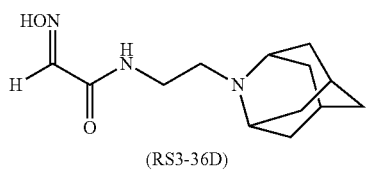

(RS3-36D) ;

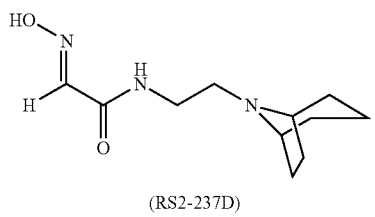

(RS2-237D) ;

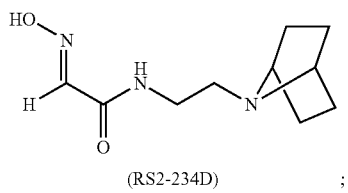

(RS2-234D) ;

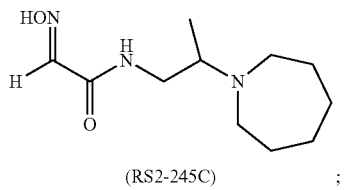

(RS2-245C) ;

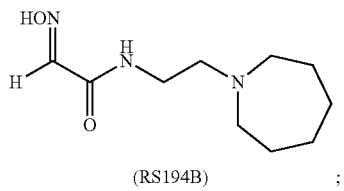

(RS194B) ;

5

-continued (RS191E);

(RS251A);

(RS251B);

(RS218A);

(RS2-138B);

(RS2-57B);

(RS2-148B);

(RS2-140B)

6

-continued (RS292A); and a combination thereof.

In alternative embodiments, the invention provides compounds having one of the following structures or compositions having one or more of the following structures, or equivalents thereof, or a stereoisomer thereof, or an analog thereof, or a pharmaceutically acceptable salt thereof; or, the invention provides a composition comprising an isolated compound consisting of, or consisting essentially of:

having a structure as set forth in Table 1 (FIG. 3) to Table 2 (FIG. 4), or equivalents thereof, or pharmaceutically acceptable salt thereof, wherein optionally the compound is RS2 138B, RS194B or RS191EE;

wherein optionally the compound is RS251A, RS251B, RS218A, or RS2-578; or wherein optionally the compound is RS2-148B, RS2-1408, RS3-43D, RS3-36D, RS2-237D, RS2-234D and RS2-245C (FIG. 4A).

In alternative embodiments, the invention provides formulations comprising a compound or composition (e.g., pharmaceutical composition) of the invention, wherein optionally the formulation is a liquid, aerosol, powder or emulsion formulation, in alternative embodiments the compositions and compounds of the invention are formulated as a pharmaceutical composition, or formulated for enteral or parenteral administration, wherein optionally the compound or formulation is administered orally, parenterally, by inhalation spray, nasally, topically, intrathecally, intrathecally, intracerebrally, epidurally, intracranially or rectally.

In alternative embodiments, the invention provides a pump, a device, a subcutaneous infusion device, a continuous subcutaneous infusion device, an infusion pen, a needle, a reservoir, an ampoule, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector, comprising a compound of the invention, or a formulation of the invention.

In alternative embodiments, the invention provides methods for treating, ameliorating or protecting (preventing) an organophosphate toxicity or poisoning or toxic exposure, or for treating, ameliorating or protecting (preventing) organophosphate inhibition of an acetylcholinesterase (AChE), comprising:

administering to a patient or an individual in need thereof, a compound of the invention, or a formulation of the invention, or administering the compound of the invention, or the formulation of the invention, using a pump, a device, a subcutaneous infusion device, a continuous subcutaneous infusion device, an infusion pen, a needles, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector of the invention.

In alternative embodiments of the methods, the organophosphate toxicity, poisoning or toxic exposure is caused by exposure of the patient or individual to an alkyl methylphosphonate or related nerve agent, or an alkylphosphorate insecticide,
and optionally the organophosphate (OP) is or is a component of a toxin, an herbicide, an insecticide, or a nerve gas or nerve agent,
and optionally the organophosphate (OP) is or comprises a parathion, a malathion, a methyl parathion, a chlorpyrifos, a diazinon, a dichlorvos, a phosmet, a fenitrothion, a tetrachlorvinphos, an azamethiphos or an azinphos methyl, or the nerve agent is a soman (O-Pinacolyl methylphosphonofluoridate), a tabun (Ethyl N,NDimethyl-phosphorarnido-cyanidate) or a sarin ((R5)-propan-2-yl methylphosphonofluoridate), In alternative embodiments of the methods, the acetylcholinesterase (AChE) is in the central nerve system (CNS), or the acetylcholinesterase (AChE) is a human acetylcholinesterase (hAChE).

In alternative embodiments, the invention provides for treating, preventing or ameliorating excessive acetylcholine stimulation in the CNS, including the brain, or in the periphery, including the peripheral nervous system (PNS), comprising:
administering to a patient or an individual in need thereof, a compound of the invention, or a formulation of the invention, or
administering a compound of the invention, or a formulation of the invention, using a pump, a device, a subcutaneous infusion device, a continuous subcutaneous infusion device, an infusion pen, a needles, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector of the invention.

In alternative embodiments of the methods, the excessive acetylcholine stimulation in the CNS, PNS or brain is caused by a drug, a drug overdose, or a poisoning or a toxic exposure to a drug, and optionally the drug overdose causing the excessive acetylcholine stimulation is caused at least in part by physostigmine, pyridostigmine, neostigmine, diisopropyl phosphorofluoridate (DFP), and/or echothiophate.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of embodiments of the invention and are not meant to limit the scope of the invention as encompassed by the claims.

FIG. 3 illustrates Table 1, which also schematically illustrates the structures of exemplary compounds of this invention, and their activity, as discussed in detail in Example 1, below.

FIG. 4 illustrates Table 2, which also schematically illustrates the structures of exemplary compounds of this invention, and exemplary activities, as discussed in detail in Example 1, below.

FIG. 12 illustrates Table 3, which describes a summary of $pK_a$ values for the exemplary compound, the lead oxime, RS194B and other selected oximes determined by four different techniques from pH-dependent changes in oxime UV spectra (cf. FIG. 7), oxime-induced ATCh oximolysis (cf. supplemental FIG. S3), and oxime-induced VX Flu-MP oximolysis (cf.

FIG. 13 illustrates Table 4, which describes the Kinetic constants for reactivation of VX-hAChE conjugate by the exemplary compounds of the invention, the oximes RS 194B, RS41A, RS186B, and reference oxime 2PAM determined in 0.1 M phosphate buffers pH 6.4, 7.4, and 8.4, as discussed in detail in Example 1, below.

FIG. 14 illustrates Table 5, which describes data from the therapy of OP-exposed mice with the exemplary compounds, the lead oximes, RS194B and RS41A and standard reference oxime 2PAM; protective index is the ratio of OP $LD_{50}$ for OP-exposed animals treated with oxime (+atropine) and for animals given OP alone (cf. supplemental Tables S2-S6), as discussed in detail in Example 1, below.

FIG. 15 illustrates Table 6, which describes the combination of therapy and pretreatment of OP-exposed mice with the exemplary compound oxime RS194B at i.m. administered doses equivalent to 25, 10, or 5% its $LD_{50}$ dose of 500 mg/kg (cf supplemental Tables S2-S6), as discussed in detail in Example 1, below.

FIG. 17 illustrates data showing the bio-availability parameters of the exemplary RS194B; where bio-availability (F) is estimated from pharmacokinetic (PK) parameters determined upon intravenous and oral administration to the mouse, and toxicity of RS194B determined upon intramuscular administration to the mouse: $LD_{50} \geq 550$ mg/kg, as discussed in detail in Example 1, below.

FIG. 19 illustrates data showing in vitro reactivation data for an antidote congener of the exemplary compounds RS 194B and RS138B; showing kinetic constants for reactivation of paraoxon-, sarin-, cyclosarin- and VX-hAChE conjugates by the exemplary RS2 138B, the principal uncharged lead oxime, the exemplary compound RS 194B, and reference oximes 2PAM, MTNA and DAM; reactivation rate constants k2, $K_{ox}$ and $k_r$ were determined from the time dependence of OP-hAChE reactivation, as discussed in detail in Example 1, below.

FIG. 21 schematically illustrates the structures of the exemplary RS2 138B and RS194B compounds; the In vitro reactivation potency of RS2 138B makes it the most promising structural analog of the lead reactivator RS194B, as discussed in detail in Example 1, below.

FIG. 22A illustrates the integration-based peak assignment, an peak integrals are indicated; FIG. 22B illustrates confirmation of peak assignment by DQF-COSY spectrum (at a 1.5 to 4.0 ppm expansion) of the same solution; spectra were taken in 20 mM $D_2O$ phosphate-pyrophosphate buffer pH 6.0 containing 100 mM NaCl, as discussed in detail in Example 1, below.

FIG. 23 A)$^1$H NMR spectrum of 2.0 mM 2PAM at pH 5 along with peak assignment; FIG. 23B) expanded view of the spectrum in the chemical shift region 7.8-8.9; FIG. 23C) pH dependent change in chemical shifts for the 8.7 ppm singlet; and, FIG. 23D) 8.77 ppm doublet; the corresponding $pK_a$ values were calculated from the observed pH induced difference in chemical shifts (FIG. 23E and FIG. 23F) by nonlinear regression using equation (1), as discussed in detail in Example 1, below.

FIGS. 24A-B graphically illustrates pH dependence of rates of 1.0 mM ATCh hydrolysis by 0.1 mM oximes (oximolysis) for the exemplary compounds RS194B (red); RS41A (blue symbols and curve); RS186B (green symbols); RS150D (magenta); and, RS174C (teal), and also: MTNA (black inverted triangles and curve) and 2PAM (white circles and black curve); grey and white/grey circles stand for spontaneous ATCh hydrolysis in the absence of oxime and DTNB hydrolysis in the absence of oxime or ATCh, respectively, as discussed in detail in Example 1, below.

FIG. 25 graphically illustrates pH dependence of rates of 0.1 mM VX Flu-MP hydrolysis by 0.5 mM oximes (OP oximolysis) for RS194B (red symbols and curve) RS41A (blue symbols and curve) and 2PAM (black and white symbols and curve); grey circles stand for spontaneous VX Flu-MP hydrolysis in the absence of oxime, as discussed in detail in Example 1, below.

Figures 26A, 26B:
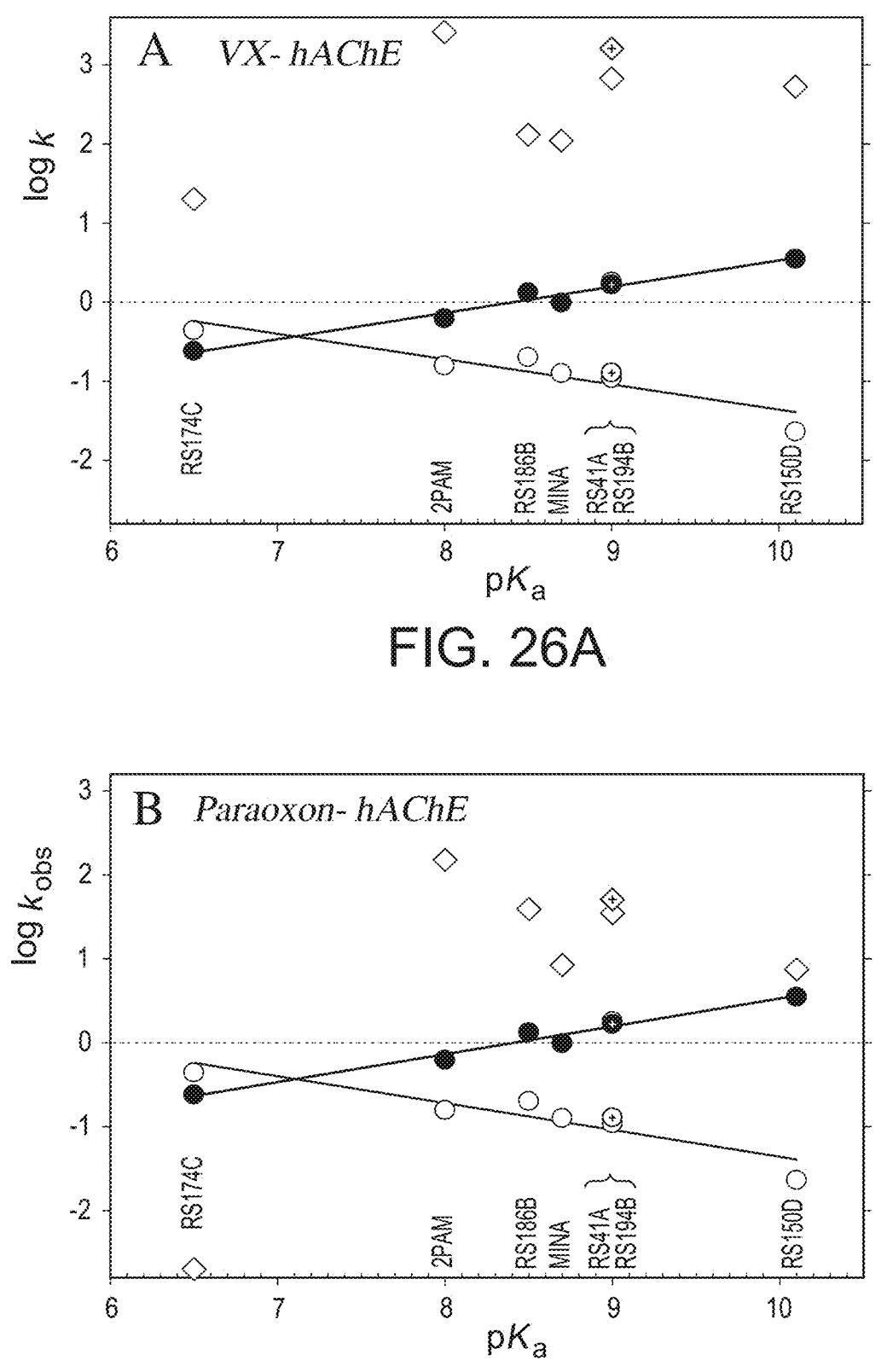

FIGS. 26A-D graphically illustrates free energy relationships between nucleophilic reactivities and oxime group ionization states of selected oxime reactivators; rate constants (k) of maximal pH dependent ATCh oximolysis (black line and circles), oximolysis at pH 7.4 (grey line and circles) and oxime reactivation $k_r$ ($M^{-1}$ $min^{-1}$) of: FIG. 26A) VX. FIG. 26B) Paraoxon, FIG. 26C) cyclosarin and FIG. 26D) sarin inhibited hAChE (yellow diamonds) in relation to $pK_a$ values determined for reactivator oxime groups; the exemplary reactivator compound RS194B is indicated by crosshaired symbols: $k_r$ for RS174C and RS150OD were extrapolated from reactivation rates determined at single (0.67 mM) oxime concentration, as discussed in detail in Example 1, below.

Figures 27C, 27D:
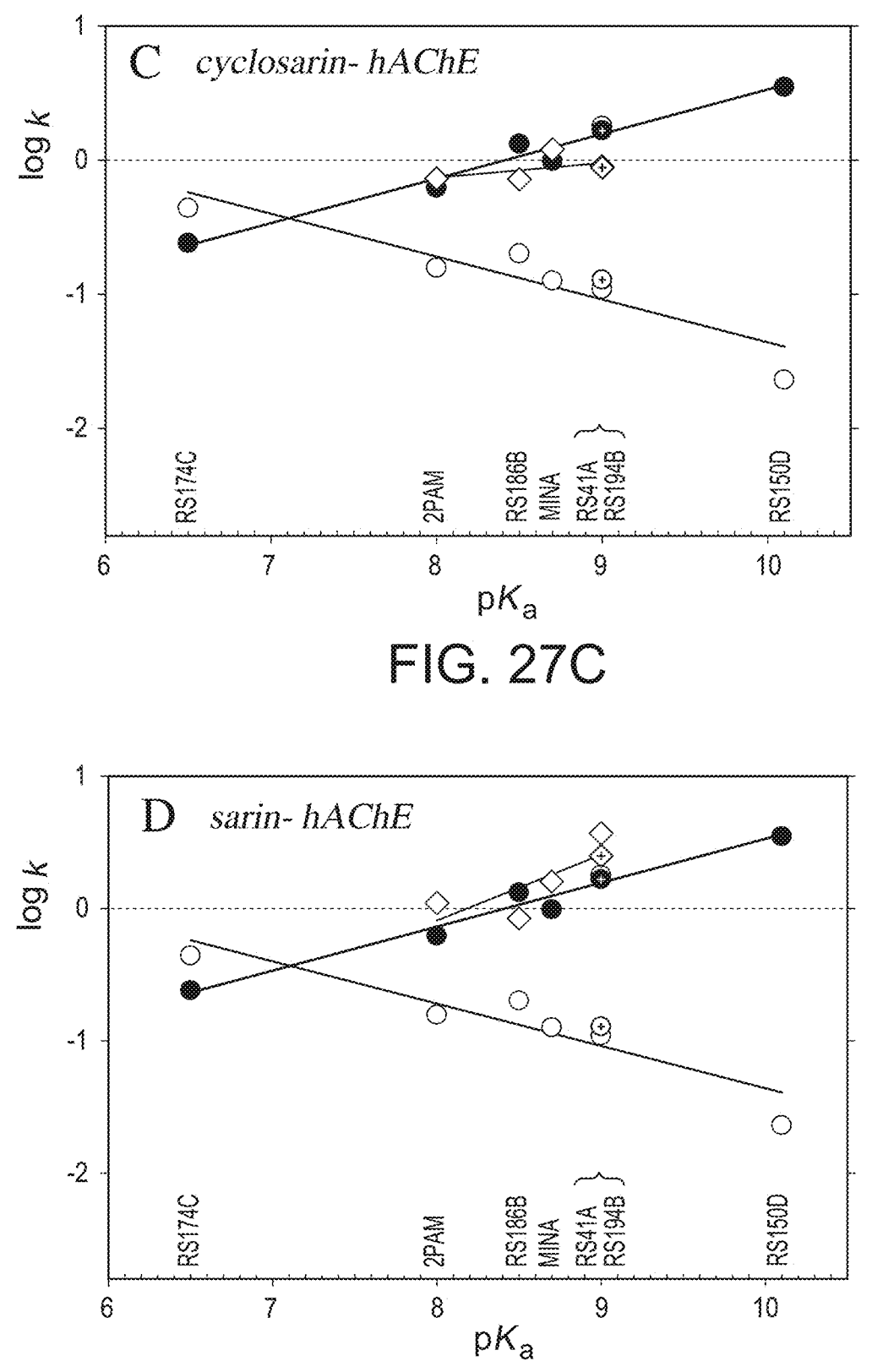

FIGS. 27A-E graphically illustrates free energy relationships between nucleophilic reactivities and oxime group ionization states of selected oxime reactivators; rate constants (k) of maximal pH dependent ATCh oximolysis (black line and circles), oximolysis at pH 7.4 (grey line and circles) and maximal oxime reactivation rate k2 ($min^{-1}$) (yellow diamonds and red line) of: FIG. 27A) VX, FIG. 27B) Paraoxon, FIG. 27C) cyclosarin. FIG. 27D) sarin inhibited hAChE and FIG. 27E) average k2 ($min^1$) in relation to $pK_a$ values determined for reactivator oxime groups. The lead reactivator RS 194B is indicated by cross-haired symbols. $k_1$ for RS 174C and RS150D were extrapolated from reactivation rates determined at single (0.67 mM) oxime concentration, as discussed in detail in Example 1, below.

FIG. 28 illustrates Table S 1, showing maximal oxime concentrations in brains and plasma of mice and halving time of those concentrations determined upon i.m. administration of a single oxime dose (cf. FIG. 5); distribution coefficients (log D) were calculated from oxime structures using ChemAxon software package, as discussed in detail in Example 1, below.

FIG. 29 illustrates Table S2, showing antidotal efficacy of oximes RS41A and RS194B given i.m. to mice after (therapy) and before and after (pretreatment+therapy) s.c. VX exposure; the oximes were administered at doses equal to 25% of their $LD_{50}$ dose. $LD_{50}$ (s.c) of VX=28.3 µg/kg, $LD_{50}$ (i.m.) of RS41A=200 mg/kg, $LD_{50}$ (i.m.) of RS194B=500 mg/kg, CD-I strain male mice; oximes in therapy were diluted in atropine (10 mg/kg), as discussed in detail in Example 1, below.

FIG. 30 illustrates Table S3, showing antidotal efficacy of oximes RS41A and RS194B given i.m. to mice after (therapy) and before and after (pretreatment+therapy) s.c. sarin exposure; the oximes were administered at doses equal to 25% of their $LD_{50}$ dose. $LD_{50}$ (s.c) of sarin=238.3 µg/kg, $LD_{50}$ (i.m.) of RS41A=200 mg/kg, $LD_{50}$ (i.m.) of RS194B=500 mg/kg, CD-I strain male mice; oximes in therapy were diluted in atropine (10 mg/kg), as discussed in detail in Example 1, below.

FIG. 31 illustrates Table S4, showing antidotal efficacy of oximes RS41A and RS194B given i.m. to mice after (therapy) and before and after (pretreatment+therapy) s.c. tabun exposure; the oximes were administered at doses equal to 25% of their $LD_{50}$ dose. $LD_{50}$ (s.c) of tabun=565.8 µg/kg, $LD_{50}$ (i.m.) of RS41A=200 mg/kg, $LD_{50}$ (i.m.) of RS194B=500 mg/kg, CD-1 strain male mice; oximes in therapy were diluted in atropine (10 mg/kg), as discussed in detail in Example 1, below.

FIG. 32 and FIG. 33 illustrate Table S5, showing antidotal efficacy of oximes RS41A and RS194B given i.m. to mice after (therapy) and before and after (pretreatment+therapy) s.c. paraoxon exposure; the oximes were administered at doses equal to 25% of their $LD_{50}$ dose. $LD_{50}$ (s.c) of paraoxon=712.9 µg/kg, $LD_{50}$ (i.m.) of RS41A=200 mg/kg, $LD_{50}$ (i.m.) of RS194B=500 mg/kg, CD-I strain male mice. Oximes in therapy were diluted in atropine (10 mg/kg), as discussed in detail in Example 1, below.

FIG. 34 illustrates Table S, showing antidotal efficacy of oximes RS41A and RS194B given i.m. to mice after (therapy) and before and after (pretreatment+therapy) s.c. soman exposure; the oximes were administered at doses equal to 25% of their $LD_{50}$ dose. $LD_{50}$ (s.c) of soman=136.1 µg/kg, $LD_{50}$ (i.m.) of RS41A=200 mg/kg, $LD_{50}$ (i.m.) of RS194B=500 mg/kg, CD-1 strain male mice; oximes in therapy were diluted in atropine (10 mg/kg), as discussed in detail in Example 1, below.

Like reference symbols in the various drawings indicate like elements.

Figure 1:
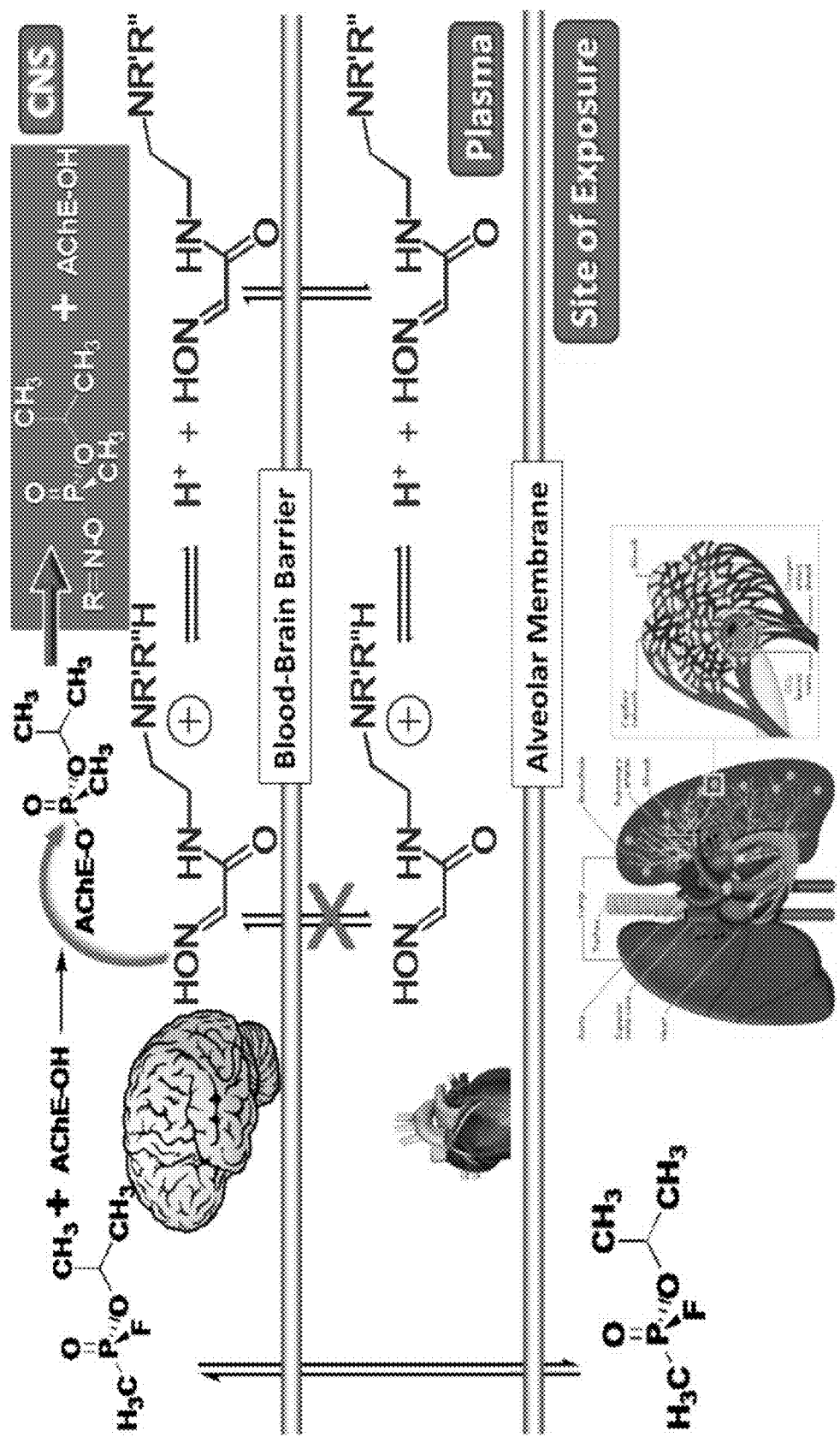
FIG. 1 schematically illustrates that the uncharged and protonated forms of acetamido oximes (highlighted with darker background) of the invention will equilibrate in blood upon intramuscular injection to OP exposed individual; the uncharged form will cross the blood-brain barrier and enter brain tissue where it will re-equilibrate; the protonated form will bind AChE-OP adduct and recover AChE catalytic activity (shown in the rectangle), as discussed in detail, below.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

The invention provides nucleophilic hydroxyimino-acetamido alkylamine antidotes that cross the blood-brain barrier (BBB) to catalyze the hydrolysis of organophosphate (OP)-inhibited human acetylcholinesterase (hAChE) in the central nerve system (CNS). In alternative embodiments, the hydroxyimino-acetamido alkylamines of the invention are designed to fit within AChE gorge dimensions and interact with the conjugated phosphate atom in the gorge. In alternative embodiments, the hydroxyimino-acetamido alkylamines of the invention are designed for optimized fit within the gorge and ionization equilibria that govern affinity and reactivity for the two linked hAChE reactivation steps. In alternative embodiments, compositions of the invention comprise uncharged but ionizable N-substituted 2-hydroxyimino-acetamido alkylamine reactivators of phosphorylated human acetylcholinesterase (hAChE) intended to catalyze the hydrolysis of organophosphate (OP)-inhibited hAChE in the CNS. In alternative embodiments, compositions of the invention comprise the so-called RS194B, an azepine analog, and RS2-138B structures and compounds.

In alternative embodiments, compositions of the invention are rapidly absorbed from the site of administration (e.g., oral, inhalation, or intramuscular, or i.m.), cross the blood-brain barrier as a neutral species, show enhanced nucleophicity from the oximate ionization species, selectively form a reversible complex with the active center gorge of an AChE, displace the covalently attached OPs, e.g., from a organophosphate toxicant such as a pesticide or a nerve agent, and restore AChE activity in the brain and periphery. In alternative embodiments, compositions and methods of the invention provide immediate protection from exposure, as well as prevention, of OP exposure, e.g., protection or prevention of immediate and recurring seizures that result from excessive acetylcholine stimulation in the brain.

In alternative embodiments, compositions of the invention have two ionization equilibria: a neutral oxime going to an anionic oximate, and a neutral amine going to a protonated amine. Hence, in these embodiments of compositions of the invention, there are four ionization states: (1) a cationic state with a positive charge on the amine (this may be the ionization state that binds best in the active center gorge); (2) an anionic state with a negative charge on the oximated (this is the active species in solution that can promote the hydrolysis of organophosphate esters; however, we cannot be so sure for the enzyme since the neutral species may bind but the enzyme may facilitate a proton transfer to form the oximated, hence the attacking species could be the zwitterion, having a positive change on the amine and a negative charge on the oximate); (3) the zwitterion, as described above, that possesses a cationic (positive) and a anionic (negative) ion or moiety; and (4) a neutral species (this is the one that crosses the blood-brain barrier and is responsible for oral absorption). The ratio of species will always adjust according to the overall pH and pKa of the residues.

In alternative embodiments, compositions of the invention whose cationic species can bind within the active center gorge, so positioned that the oximate (the reactive warhead) can attack the conjugated phosphorus. In alternative embodiments, the oximate can access the phosphorus in the narrow and impacted region of the gorge. In alternative embodiments, compositions of the invention can have a small fraction of neutral species, perhaps 10% to 20%, so that the compound will cross the blood-brain barrier and can be absorbed after oral administration.

With these exemplary properties, compositions of the invention can access the CNS and peripheral nervous system and reactivate cholinesterases inhibited by pesticides and nerve agents. In alternative embodiments, compositions of the invention can be an antidote for poisoning by organophosphate (e.g., diisopropylfluorophosphates and echothiophate) and carbamylating drugs (e.g., physostigmine, neostigmine and pyridostigmine). In alternative embodiments, compositions of the invention can assist in the catalysis of the organophosphate itself before it gets to the enzyme; hence, compositions of the invention can have a scavenging capacity for the parent organophosphate; catalysis is carried out by acetylcholinesterase or butyrylcholinesterase and the oxime facilitates this.

In alternative embodiments, compounds of the invention can not only cross the blood-brain barrier to reactivate acetylcholinesterase in the CNS and peripheral nervous system, but compounds of the invention also are effective as antidotes and protective (prophylactic) agents when given orally. In alternative embodiments, for example, as a prophylactic agent, the oral dosage route does not have the most rapid onset, but is an ideal route for achieving prolonged antidote activity; this can be the most practical route for prophylactic use against massive releases of volatile gases, for example, prophylactic or therapeutic use in accidents or in poison gas (e.g., nerve agent) warfare, e.g., paraoxon, sarin, cyclosarin and VX attacks.

In alternative embodiments, compositions of the invention have improved antidote efficacy for various organophosphates, e.g., methylphosphonate nerve agents and phosphorate insecticides, and have a lower toxicity than 2-PAM, and an increased half-life in the brain when compared with other compounds. In alternative embodiments, compositions of the invention, e.g., the compound RS194b, are designed to have an optimized fit within an AChE gorge, and ionization equilibria dictating affinity and reactivity for the two linked reactivation steps.

For example, FIG. 1 schematically illustrates that the uncharged and protonated forms of acetamido oximes (shown in blue) of the invention will equilibrate in blood upon intramuscular injection to OP exposed individual. The uncharged form will cross the blood-brain barrier and enter brain tissue where it will re-equilibrate. The protonated form will bind AChE-OP adduct and recover AChE catalytic activity (shown in the red rectangle). Thus, in alternative embodiments, compositions of the invention are antidotes to various organophosphates, including methylphosphonates and other nerve agents as well as the phosphorate insecticides, and methods of the invention are used to treat, ameliorate or prevent organophosphate nerve agent poisoning or toxic effects subsequent to organophosphate insecticide exposure. Furthermore, in alternative embodiments, compositions of the invention act as a universal antidote to non-aging nerve agents, e.g., compositions of the invention can be used as countermeasures to organophosphate nerve agents, e.g., as those that could be used chemical terrorism. In alternative embodiments, compositions of the invention limit the toxicity and threat potential of organophosphate nerve agents by assisting the catalytic breakdown of the organophosphates by e.g., butyrylcholinesterase in plasma and tissues. In alternative embodiments, compositions of the invention limit the toxicity and threat potential of organophosphate nerve agents by assisting the butyrylcholinesterase catalysis of the organophosphate.

Bioisosteres of Compounds of the Invention

In alternative embodiments, the invention also provides bioisosteres of compounds of the invention. In alternative embodiments, bioisosteres of the invention are compounds of the invention comprising one or more substituent and/or group replacements with a substituent and/or group having substantially similar physical or chemical properties which produce substantially similar biological properties to a compound of the invention, or stereoisomer, racemate or isomer thereof. In one embodiment, the purpose of exchanging one bioisostere for another is to enhance the desired biological or physical properties of a compound without making significant changes in chemical structures.

For example, in one embodiment, bioisosteres of compounds of the invention are made by replacing one or more hydrogen atom(s) with one or more fluorine atom(s), e.g., at a site of metabolic oxidation; this may prevent metabolism (catabolism) from taking place. Because the fluorine atom is only slightly larger than the hydrogen atom the overall topology of the molecule is not significantly affected, leaving the desired biological activity unaffected. However, with a blocked pathway for metabolism, the molecule may have a longer half-life or be less toxic, and the like.

Products of Manufacture. Kits

The invention also provides products of manufacture and kits for practicing the methods of this invention. In alternative embodiments, the invention provides products of manufacture and kits comprising all the components needed to practice a method of the invention.

The invention provides kits comprising compositions and/or instructions for practicing methods of the invention. In alternative embodiments, the invention provides kits comprising: a composition used to practice a method of any of the invention, optionally comprising instructions for use thereof.

In alternative embodiments, the invention provides pumps, devices, subcutaneous infusion devices, continuous subcutaneous infusion device, infusion pens, needles, reservoirs, ampoules, vials, syringes, cartridges, disposable pen or jet injectors, prefilled pens or syringes or cartridges, cartridge or disposable pen or jet injectors, two chambered or multi-chambered pumps, syringes, cartridges or pens or jet injectors comprising a composition or a formulation of the invention. In alternative embodiments, the injector is an autoinjector, e.g., a SMARTJECT® autoinjector (Janssen Research and Development LLC); or a MOLLY®, or DAI®, or DAI-RNS® autoinjector (SHL Group, Deerfield Beach, Fla.). In alternative embodiments, the injector is a hypodermic or a piston syringe.

Formulations and Pharmaceutical Compositions

In alternative embodiments, the invention provides compounds and compositions, including formulations and pharmaceutical compositions, for use in in vivo, in vitro or ex vivo methods for catalyzing the hydrolysis of organophosphate (OP)-inhibited human acetylcholinesterase (hAChE) in the central nerve system (CNS); or, for treating, ameliorating or protecting (preventing) an organophosphate toxicity or poisoning or toxic exposure, or for treating, ameliorating or protecting (preventing) organophosphate inhibition of an acetylcholinesterase (AChE); or, for treating, preventing or ameliorating excessive acetylcholine stimulation in the CNS, or the brain.

In alternative embodiments, the pharmaceutical compositions of the invention can be administered parenterally, topically, orally or by local administration, such as by aerosol or transdermally. In alternative embodiments, pharmaceutical compositions can be prepared in various forms, such as granules, tablets, pills, capsules, suspensions, taken orally, suppositories and salves, lotions and the like. Pharmaceutical formulations of this invention may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, geltabs, on patches, in implants, etc. In practicing this invention, the pharmaceutical compounds can be delivered by transdermally, by a topical route, formulated as applicator sticks, solutions, suspensions, emulsions, gels, creams, ointments, pastes, jellies, paints, powders, and aerosols. Oral carriers can be elixirs, syrups, capsules, tablets, pills, geltabs and the like.

In alternative embodiment, compositions of the invention are delivered orally, e.g., as pharmaceutical formulations for oral administration, and can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methyl-cellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

In alternative embodiments, liquid carriers are used to manufacture or formulate compounds of this invention, or a composition used to practice the methods of this invention, including carriers for preparing solutions, suspensions, emulsions, syrups, elixirs and pressurized compounds. The active ingredient (e.g., a composition of this invention) can be dissolved or suspended in a pharmaceutically acceptable liquid carrier such as water, an organic solvent, a mixture of both or pharmaceutically acceptable oils or fats. The liquid carrier can comprise other suitable pharmaceutical additives such as solubilizers, emulsifiers, buffers, preservatives, sweeteners, flavoring agents, suspending agents, thickening agents, colors, viscosity regulators, stabilizers or osmo-regulators.

In alternative embodiments, solid carriers are used to manufacture or formulate compounds of this invention, or a composition used to practice the methods of this invention, including solid carriers comprising substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

In alternative embodiments, concentrations of therapeutically active compound in a formulation can be from between about 0.1% to about 100% by weight.

In alternative embodiments, therapeutic formulations are prepared by any method well known in the art, e.g., as described by Brunton et al., eds., Goodman and Gilman's: The Pharmacological Bases of Therapeutics, 12th ed., McGraw-Hill, 2011; Remington: The Science and Practice of Pharmacy, Mack Publishing Co., 20th ed., 2000; Avis et al., eds., Pharmaceutical Dosage Forms: Parenteral Medications, published by Marcel Dekker, Inc., N.Y., 1993; Lieberman et al., eds., Pharmaceutical Dosage Forms: Tablets, published by Marcel Dekker, Inc., N.Y., 1990; and Lieberman et al., eds., Pharmaceutical Dosage Forms: Disperse Systems, published by Marcel Dekker, Inc., N.Y., 1990.

In alternative embodiments, therapeutic formulations are delivered by any effective means appropriated for a particular treatment. For example, depending on the specific antitumor agent to be administered, the suitable means include oral, rectal, vaginal, nasal, pulmonary administration, or parenteral (including subcutaneous, intramuscular, intravenous and intradermal) infusion into the bloodstream. For parenteral administration, antitumor agents of the present invention may be formulated in a variety of ways. Aqueous solutions of the modulators can be encapsulated in polymeric beads, liposomes, nanoparticles or other injectable depot formulations known to those of skill in the art. In alternative embodiments, compounds of the invention are administered encapsulated in liposomes (see below). In alternative embodiments, depending upon solubility, compositions are present both in an aqueous layer and in a lipidic layer, e.g., a liposomic suspension. In alternative embodiments, a hydrophobic layer comprises phospholipids such as lecithin and sphingomyelin, steroids such as cholesterol, more or less ionic surfactants such a diacetylphosphate, stearylamine, or phosphatidic acid, and/or other materials of a hydrophobic nature.

The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co., Easton Pa. ("Remington's"). For example, in alternative embodiments, these compositions of the invention are formulated in a buffer, in a saline solution, in a powder, an emulsion, in a vesicle, in a liposome, in a nanoparticle, in a nanolipoparticle and the like. In alternative embodiments, the compositions can be formulated in any way and can be applied in a variety of concentrations and forms depending on the desired in vivo, in vitro or ex vivo conditions, a desired in vivo, in vitro or ex vive method of administration and the like. Details on techniques for in vivo, in vitro or ex vivo formulations and administrations are well described in the scientific and patent literature. Formulations and/or carriers used to practice this invention can be in forms such as tablets, pills, powders, capsules, liquids, gels, syrups, slurries, suspensions, etc., suitable for in vivo, in vitro or ex vivo applications.

In practicing this invention, the compounds (e.g., formulations) of the invention can comprise a solution of compositions disposed in or dissolved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations used to practice the invention are sterile and can be manufactured to be generally free of undesirable matter. In one embodiment, these solutions and formulations are sterilized by conventional, well known sterilization techniques.

The solutions and formulations used to practice the invention can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and can be selected primarily based on fluid volumes, viscosities and the like, in accordance with the particular mode of in vivo, in vitro or ex vivo administration selected and the desired results.

The compositions and formulations of the invention can be delivered by the use of liposomes. In alternative embodiments, by using liposomes, particularly where the liposome surface carries ligands specific for target cells or organs, or are otherwise preferentially directed to a specific tissue or organ type, one can focus the delivery of the active agent into a target cells in an in vivo, in vitro or ex vivo application.

The compositions and formulations of the invention can be directly administered, e.g., under sterile conditions, to an individual (e.g., a patient) to be treated. The modulators can be administered alone or as the active ingredient of a pharmaceutical composition. Compositions and formulations of this invention can be combined with or used in association with other therapeutic agents. For example, an individual may be treated concurrently with conventional therapeutic agents.

Nanoparticles. Nanolipoparticles and Liposomes

The invention also provides nanoparticles, nanolipoparticles, vesicles and liposomal membranes comprising compounds and compositions used to practice the methods of this invention, e.g., methods for catalyzing the hydrolysis of organophosphate (OP)-inhibited human acetylcholinesterase (hAChE) in the central nerve system (CNS); or, for treating, ameliorating or protecting (preventing) an organophosphate toxicity or poisoning or toxic exposure, or for treating, ameliorating or protecting (preventing) organophosphate inhibition of an acetylcholinesterase (AChE); or, for treating, preventing or ameliorating excessive acetylcholine stimulation in the CNS, or the brain The invention provides multilayered liposomes comprising compounds used to practice this invention, e.g., as described in Park, et al., U.S. Pat. Pub. No. 20070082042.

The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice this invention.

Liposomes can be made using any method, e.g., as described in Park, et al, U.S. Pat. Pub. No. 20070042031, including method of producing a liposome by encapsulating an active agent (e.g., a compound of the invention), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice this invention comprise a substituted ammonium and/or polyanions, e.g., for targeting delivery of a compound (e.g., e.g., a compound of the invention) used to practice this invention to a desired cell type or organ, e.g., brain, as described e.g., in U.S. Pat. Pub. No. 200701 10798.

The invention also provides nanoparticles comprising compounds (e.g., a compound of the invention) used to practice this invention in the form of active agent-containing nanoparticles (e.g., a secondary nanoparticle), as described, e.g., in U.S. Pat. Pub. No. 20070077286. In one embodiment, the invention provides nanoparticles comprising a fat-soluble active agent of this invention or a fat-solubilized water-soluble active agent to act with a bivalent or trivalent metal salt.

In one embodiment, solid lipid suspensions can be used to formulate and to deliver compositions used to practice this invention to mammalian cells in vivo, in vitro or ex vivo, as described, e.g., in U.S. Pat. Pub. No. 20050136121.

Delivery Vehicles

In alternative embodiments, any delivery vehicle can be used to practice the methods or used to practice this invention, e.g., to deliver compositions of the invention (e.g., a compound of the invention) to mammalian cells in vivo, in vitro or ex vivo. For example, delivery vehicles comprising polycations, cationic polymers and/or cationic peptides, such as polyethyleneimine derivatives, can be used e.g. as described, e.g., in U.S. Pat. Pub. No. 20060083737.

In one embodiment, a dried polypeptide-surfactant complex is used to formulate a composition used to practice this invention, e.g. as described, e.g., in U.S. Pat. Pub. No. 20040151766.

In one embodiment, a composition used to practice this invention can be applied to cells using vehicles with cell membrane-permeant peptide conjugates, e.g., as described in U.S. Pat. Nos. 7,306,783; 6,589,503. In one aspect, the composition to be delivered is conjugated to a cell membrane-permeant peptide. In one embodiment, the composition to be delivered and/or the delivery vehicle are conjugated to a transport-mediating peptide, e.g., as described in U.S. Pat. No. 5,846,743, describing transport-mediating peptides that are highly basic and bind to poly-phosphoinositides.

In one embodiment, electro-permeabilization is used as a primary or adjunctive means to deliver the composition to a cell, e.g., using any electroporation system as described e.g. in U.S. Pat. No. 7,109,034; 6,261,815; 5,874,268.

Dosaging

The pharmaceutical compositions and formulations of the invention can be administered for prophylactic and/or therapeutic treatments. In therapeutic applications, compositions are administered to a subject already exposed to a toxin, or exposed to any agent or chemical causing or resulting in excessive acetylcholine stimulation in the brain, e.g., exposure to a drug, a drug overdose, or a poisoning or a toxic exposure to a drug, and optionally the drug overdose causing the excessive acetylcholine stimulation is caused at least in part by: physostigmine, neostigmine, pyridostigmine, diisopropylfluorophosphate, or echothiophate an amount sufficient to cure, alleviate or partially arrest the clinical manifestations of the agent and/or its complications (a "therapeutically effective amount").

The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:61 1-617; Groning (1996) Pharmazie 51:337-341; Fotherby (1996) Contraception 54:59-69; Johnson (1995) J. Pharm. Sci. 84: 1144-1146; Rohatagi (1995) Pharmazie 50:610-613; Brophy (1983) Eur. J. Clin. Pharmacol. 24: 103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

The invention will be further described with reference to the following examples; however, it is to be understood that the invention is not limited to such examples.

EXAMPLES

Example 1

This example demonstrates the effectiveness of compositions of the invention as a antidotes to organophosphates and organophosphate poisoning and toxicity.

We present a systematic structural optimization of uncharged but ionizable N-substituted 2-hydroxyiminoacetamido alkylamine reactivators of phosphylated human acetylcholinesterase (hAChE) intended to catalyze the hydrolysis of organophosphate (OP)-inhibited hAChE in the CNS. Starting with the initial lead oxime RS41A identified in our earlier study and extending to the azepine analog RS 194B, reactivation rates for OP-hAChE conjugates formed by sarin, cyclosarin, VX, paraoxon, and tabun are enhanced several-fold in vitro. To analyze the mechanism of intrinsic reactivation of the OP-AChE conjugate and penetration of the blood-brain barrier, the pH dependence of the oxime and amine ionizing groups of the compounds and their nucleophilic potential were examined by UV-visible spectroscopy, $^1$H NMR, and oximolysis rates for acetylthiocholine and phosphoester hydrolysis. Oximolysis rates were compared in solution and on AChE conjugates and analyzed in terms of the ionization states for reactivation of the OP-conjugated AChE. In addition, toxicity and pharmacokinetic studies in mice show significantly improved CNS penetration and retention for RS 194B when compared with RS41A. The enhanced intrinsic reactivity against the OP-AChE target combined with favorable pharmacokinetic properties resulted in great improvement of antidotal properties of RS 194B compared with RS41A and the standard peripherally active oxime, 2-pyridinealdoxime methiodide. Improvement was particularly noticeable when pretreatment of mice with RS 194B before OP exposure was combined with RS 194B reactivation therapy after the OP insult.

The invention provides an ideal centrally acting reactivator that combines the properties of efficient reactivation and blood-brain barrier penetration. Our initial approach was to develop a library of uncharged oxime reactivators amenable to protonation (1) and identify a lead structure. A reactivator, the so-called RS41A (Table 1), is comparable in its in vitro reactivating potency to standard pyridinium oxime reactivator 2PAM, was selected from a large synthetic library.

In this study we describe systematic variations of RS41A structure and a detailed evaluation of associated reactivating properties leading to several enhanced reactivators culminating in the several-fold improved azepine analog RS194B. By virtue of enhanced association with OP-hAChE conjugates, RS194B showed substantially improved in vitro reactivation kinetics compared with the initial lead RS41A. Moreover, the low toxicity of RS194B in the mouse animal model in combination with its enhanced intrinsic reactivity results in substantial improvement of its therapeutic properties compared with RS41A and the standard oxime, 2PAM. The improvement was particularly noticeable when pretreatment of mice with RS 194B before OP exposure was combined with RS 194B reactivation therapy after the OP insult. We describe here the mechanistic basis for this enhancement in terms of the intrinsic reaction constants and pharmacokinetic profiles.

Since RS194B crosses the blood-brain barrier and has a reasonable fraction of neutral, non-ionized species at physiological pH, it can also be expected to be cross gastrointestinal membranes and hence will be efficacious after oral administration.

Materials and Methods

Enzyme: Highly purified monomeric hAChE was prepared as described e.g. in Sit et al. (2011) J. Biol. Chem. 286, 19422-19430; Cochran et al. (2011)) J. Biol. Chem. 286, 29718-29724.

Organophosphates: Low toxicity, nonvolatile fluorescent methylphosphonates (Flu-MPs) (see e.g., Amitai (2007) Toxicology 233, 187-198) were used in in vitro experiments as analogues of nerve agents sarin, cyclosarin, and VX. The Flu-MPs differ from actual nerve agent OPs only by the structure of their respective leaving groups. Inhibition of hAChE by Flu-MPs results in OP-hAChE covalent conjugates identical to the ones formed upon inhibition with the corresponding volatile OPs. Paraoxon was purchased from Sigma. Nerve agent OPs tabun. VX, sarin, and soman used in in vivo experiments were purchased from NC Laboratory (Spiez, Switzerland).

Oximes: 2-Pyridinealdoxime methiodide (2PAM), monoisonitrosoacetone (MINA), and 2,3-butanedione monoxime (DAM) were purchased from Sigma.

Figure 2:
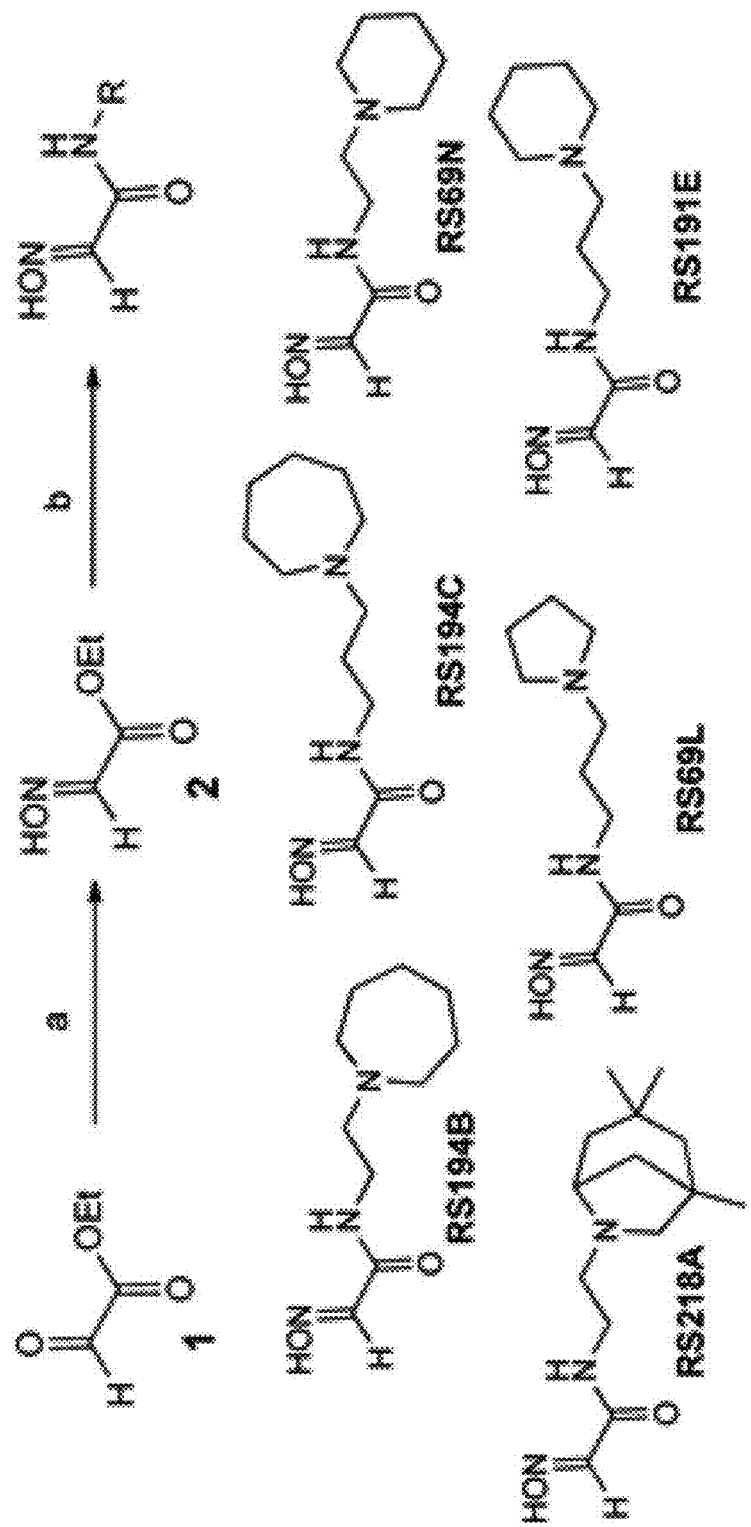
FIG. 2 schematically illustrates Scheme 1, the preparation of exemplary oximes of the invention, including: N-Substituted 2-hydroxyiminoacetamides RS 194B, RS 194C, RS69N, RS218A, RS69L, and RS191E, which were prepared from ethyl glyoxylate (7) in two steps, as discussed in detail in Example 1, below.
Figure 5A:
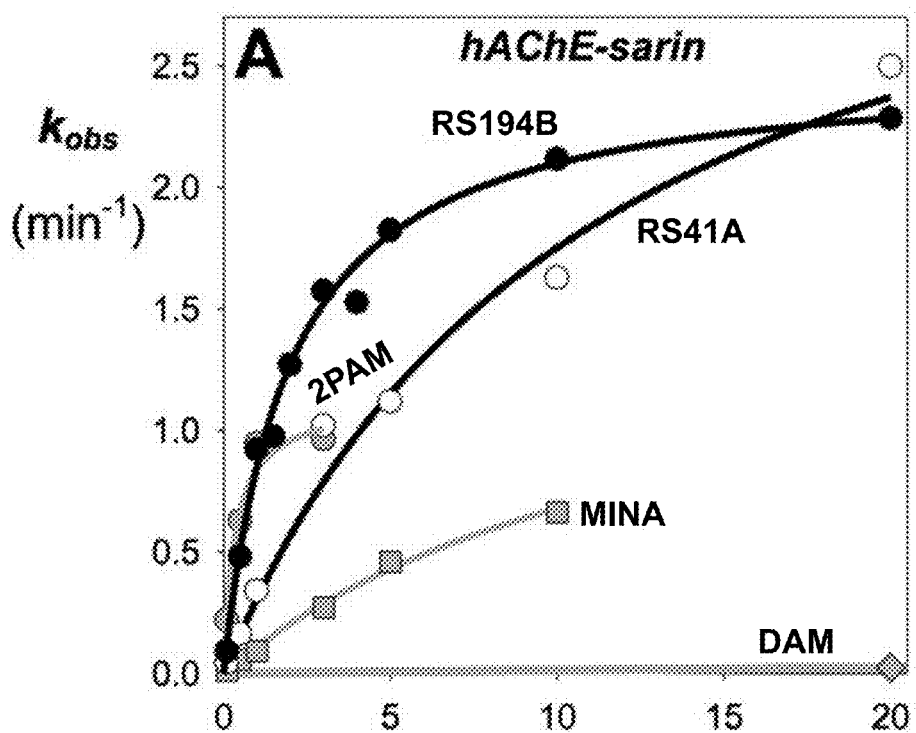
FIGS. 5A-E graphically illustrates the concentration dependence of oxime reactivation of sarin (A)-, VX (B)-, cyclosarin (Q-, paraoxon (D)-, and tabun (E)-inhibited (conjugated) hAChE; dependence for the exemplary compound, the lead oxime, RS194B (black circle) and the exemplary compound, the initial lead, RS41A (open circle) compared with reference uncharged (DAM (gray diamond) and MI'NA (gray square)) and cationic (2PAM (gray square) oximes, as discussed in detail in Example 1, below, FIGS. 6A-C graphically illustrates the pH dependence of UV spectra of 50 µM of the exemplary compound RS41A and pH dependence of $A_{270\ nm}$ of 50 µM (A) of the exemplary compound RS41A (B), and RS194B along with corresponding $pK_a$ values calculated by nonlinear regression using Equation 1 (C), as discussed in detail in Example 1, below.
Figure 5B:
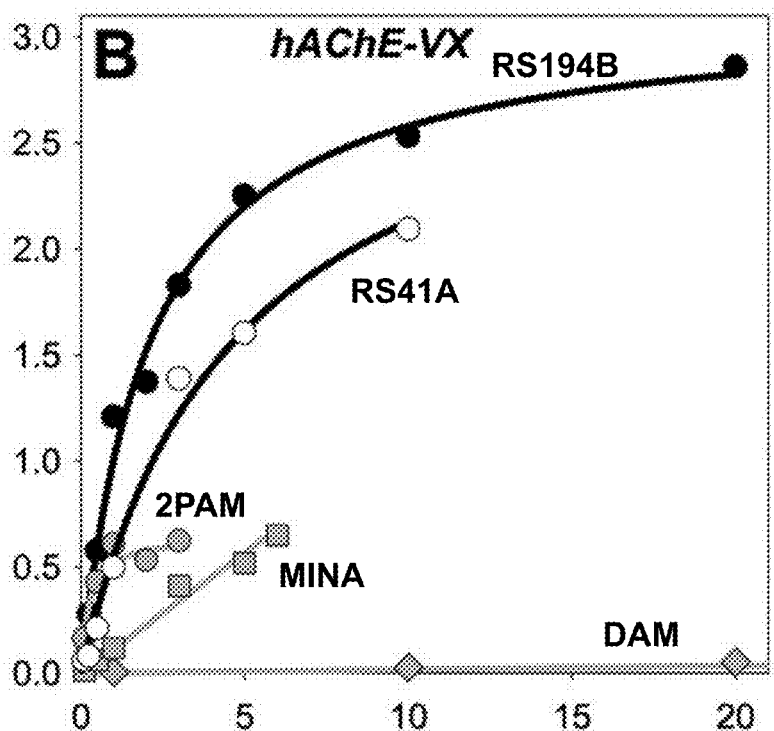
Figure 5C:
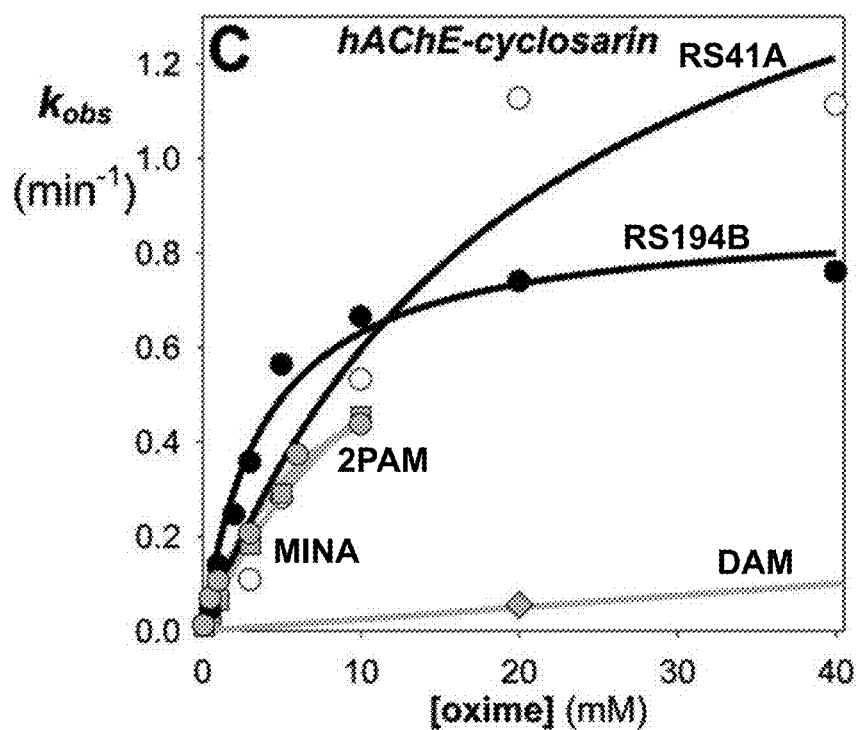
Figure 5D:
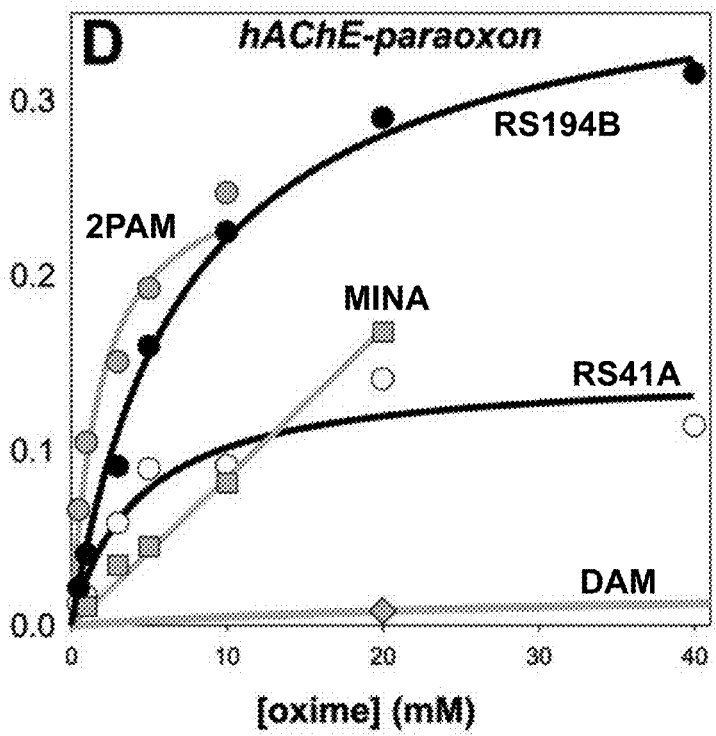
Figure 5E:
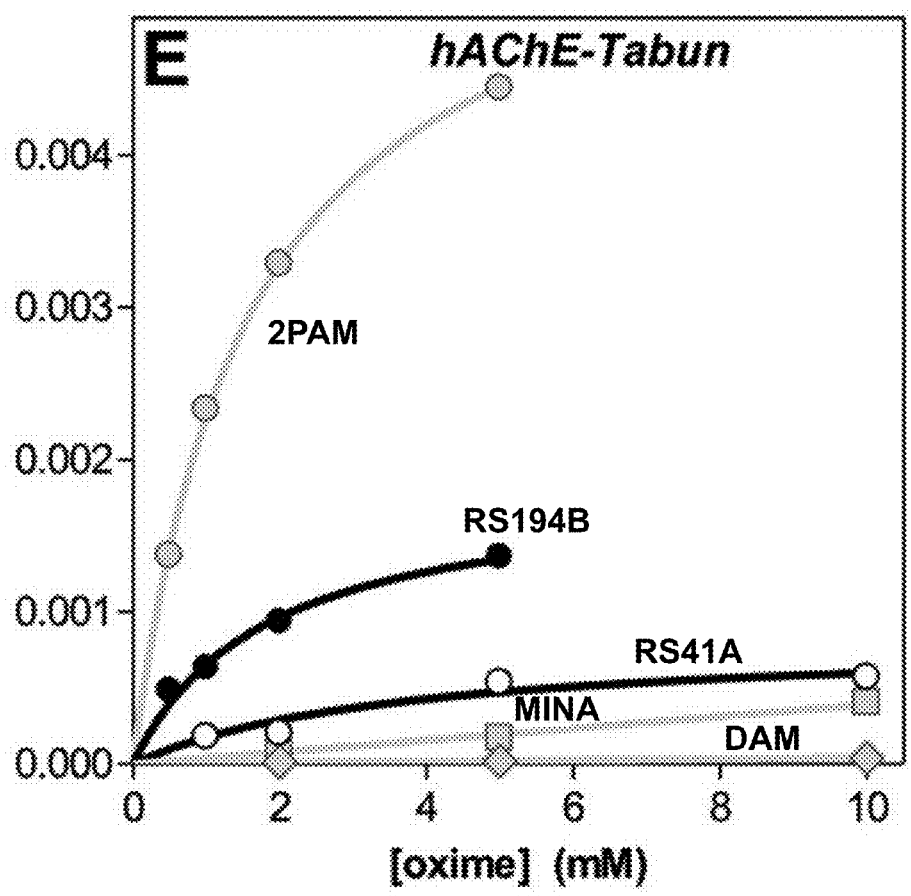

Preparation of exemplary Oximes of the invention: N-Substituted 2-hydroxyiminoacetamides RS194B, RS 194C, RS69N, RS218A, RS69L, and RS191E were prepared from ethyl glyoxylate (7) in two steps, see Scheme 1, illustrated as FIG. 2. Condensation with hydroxylamine provided ethyl glyoxylate oxime (2) followed by subsequent amidation with the corresponding primary amine.

Scheme 1

In Vitro Oxime Reactivation Assays hAChE activities were measured using a spectrophotometric assay (see reference 18, below) at 25° C. in 0.1 m sodium phosphate buffer, pH 7.4, containing 0.01% BSA and 1.0 mm substrate acetylthiocholine (ATCh). OP-hAChE conjugates were prepared, and oxime reactivation was performed (at 37° C. in 0.1 m sodium phosphate buffer, pH 7.4, containing 0.01% BSA) as described in references 1, 16, below). The first order reactivation rate constant ($k_{obs}$) for each oxime+OP conjugate combination was calculated by nonlinear regression, as described in reference 19. The dependence of reactivation rates on oxime concentrations and determination of maximal reactivation rate constant $k_2$, Michaelis-Menten type constant $K_{ox}$, and the overall second order reactivation rate constant $k_r$ were conducted as previously described in reference 19. The pH dependence of oxime reactivation of AChE was performed in 0.1 m phosphate buffers pH 6.4, 7.4, or 8.4 containing 0.01% BSA.

Oxime $pK_a$ Determinations

Protonation of ionizable groups in oximes was monitored either using UV-visible spectrophotometry or by NMR spectrometry. A series of 20 mM phosphate-pyrophosphate buffers pH 5.0, 6.0, 7.0, 8.0, 8.5, 9.0, 9.5, 10, 10.5, and 11 (containing 0.1 m NaCl) were prepared in either $H_2O$ or D2O. For D2O buffers, pD values were determined by correcting the pH reading by +0.4 pH units (cf. Ref. 20, see below). UV spectra of oximes between 220- and 320-nm wavelengths were recorded on Cary IE (Varian) UV-visible spectrophotometer at the above pH values, and absorbance at 270 nm (A270 nm) was plotted as a function of pH yielding $pK_a$ values by nonlinear regression of Equation 1:

$$A270\ nm = A^{max}_{270\ nm}/(1+[H^+]1\ KB)$$

$^1$H NMR spectra recorded on Bruker DRX-500™ (Bruker, USA) spectrometer in 20 mm phosphate-pyrophosphate D2O buffers pH 5.0, 6.0, 7.0, 8.0. 8.5, 9.0, 9.5, and 10 (containing 0.1 m NaCl) were overlaid and aligned using benzene as an external standard placed in a separate capillary tube within the NMR sample probe. Two-dimensional $^1$H,$^1$H double-quantum filtered COSY spectra were recorded on a Bruker DRX-600™ spectrometer.

Computational Molecular Modeling

Interactions of oximes RS41A and RS 194B within the active center gorge of VX-inhibited hAChE were studied for the reversible complex and for the trigonal bipyramidal intermediate for the reactivation step using a simulated annealing molecular dynamics approach (see reference 21). Covalent conjugates of hAChE ethylmethylphosphonylated at the active Ser-203 were generated by pasting ethylmethylphosphonylated Ser-203 of mouse AChE structure (PDB 2JGH) into the native WT hAChE structure (PDB 3LII) and subsequent semiempirical quantum mechanical adjustment of partial charges by InsightII™ suite (Accelrys, San Diego, Calif.). All water molecules were removed from the PDB structures, and a dielectric constant of four was used in calculation to mimic the interior of the hAChE active center gorge. In calculations for formation of the reversible complex, distances between oximate oxygen and the P atom of the VX conjugate were flexibly constrained to a distance between 0 and 3.00 A. In trigonal bipyramidal intermediate calculations, the oximate oxygen was covalently linked to the P atom rehybridized to pentacoordinate geometry (see reference 21). Ten calculations were made for each oxime at both the reversible complex and trigonal bipyramidal intermediate steps allowing the oxime molecule and hAChE residues 72, 124, 286, 297, 341, and VX-conjugated Ser-203 to rotate freely, whereas all other enzyme side chains were fixed.

Acute Oxime Toxicity and Oxime Treatment of OP-Exposed Mice

Male CD-1 mice (25-30 g body weight) were purchased from Rudjer Boskovic Institute. Zagreb, Croatia. Mice were fed on a standard diet, had free access to water, and were kept in Macrolone cages at 21° C. exchanging light and dark cycles every 12 h. For the experimental sequence, mice were divided into groups of four. The mice were treated in accord with the approval of the Ethical Committee of the Institute for Medical Research and Occupational Health in Zagreb, Croatia.

Acute intramuscular (i.m.) toxicity ($LD_{50}$) was based upon 24-h mortality rates calculated according to Thompson (see reference 22) and Weil (see reference 23). Each $LD_{50}$ was evaluated from the results obtained with four to six doses of a given oxime (dissolved in water plus a minute amount of HCl to form the corresponding hydrochloride salt).

Antidotal activity against OP poisoning was tested by giving male CD-1 mice the studied oximes i.m. (at the specified dose) together with atropine sulfate (10 mg/kg) 1 min after subcutaneous OP administration (see references 24, 25) or p.o. (by oral administration) 15 min before OP followed by i.m. (intramuscular) atropine injection 1 min after OP. Stock solutions of nerve agents were prepared in isopropyl alcohol or in propylene glycol. Further dilutions were made in saline immediately before use.

Alternatively, mice were pretreated i.m. with oximes (at specified dose but without atropine) 5 or 15 min before subcutaneous OP administration. The combination of pretreatment and antidotal therapy was performed by i.m. pretreatment with oxime 15 min before subcutaneous OP administration followed by i.m. administration of oxime (dissolved in 5 mg/ml atropine sulfate) 1 min after the OP exposure.

The antidotal efficacy of oximes was expressed as protective index (PI) with 95% confidence limits and the maximal dose of OP. The PI was the ratio of $LD_{50}$ between OP with antidote and OP given alone. The maximal dose of organophosphate was the highest multiple of the OP $LD_{50}$, which was fully counteracted by the oximes.

Oxime Pharmacokinetics in Mice

Female CD-1 mice 4-8 weeks old (22-34 g of body weight) were purchased from Harlan (Livermore, Calif.). Mice were fed Purina Certified Rodent Chow #5002. Food and purified water were provided ad libitum. Mice were kept in hanging polycarbonate cages at 21-23° C., exchanging light and dark cycles every 12 h. General procedures for animal care and housing were in accordance with the National Research Council Guide for the Care and Use of Laboratory Animals (1996) and the Animal Welfare Standards incorporated in 9 CFR Part 3, 1991.

For experiments mice were divided into groups of three. In the pharmacokinetic studies, 80 mg/kg RS194B or 30 mg/kg RS41A oxime was administered i.m. as a single dose in the absence of OP. Three animals were injected for every time point analyzed. Alternatively oxime was administered orally in a single dose, or repetitively every two hours after the initial p.o. administration. Brain and plasma were collected at each time point following the oxime administration. Blood (approximately 300 μl) was collected from the retro-orbital sinus of mice under isoflurane anesthesia into tubes containing EDTA, processed to plasma within 30 min of collection, and then stored frozen at ≤−80° C. (+10° C.).

Brains were collected and analyzed individually at each time point. Brain weight was documented for each animal before storage on dry ice. Brains were stored at ≤−80° C. (+10° C.) until analysis. Concentration of the oxime in body compartments was determined by LC-MS using multiple reaction monitoring electrospray ionization detection in positive ion mode.

Results

Systematic Variations of RS41A Structure

Our recent characterization (see reference 1) of a library of 135 uncharged, structurally diverse oximes revealed hydroxyimino acetamido amines as efficient reactivators of OP-hAChE conjugates. In particular, the selected lead structure RS41A appeared similar in reactivation potency to the standard reference oxime 2PAM.

With the aim of better understanding structure/activity relationships of the hydroxyimino acetamido alkylamine reactivators and specifically improving RS41A reactivation properties, we synthesized new reactivators by systematically modifying structure, see Table 1, which describes the structures and initial screen of relative rate constants ($K_{obs}$) for OP-hAChE reactivation of selected uncharged reactivators (0.67 mm) in comparison to cationic pyridinium aldoxime 2PAM; Nonenzymic oximolysis rates of ATCh (1 mm) by 1.0 mm oximes and calculated percentages of oximate anion and neutral species at pH 7.4 are also given as well as volume and surface area of R in the general oxime formula HO=NCHC(O)NH—R. Experiments were performed in duplicate at 37° C. in 0.10 m phosphate buffer, pH 7.4.

In Table 1: Nonenzymic oximolysis rates of ATCh (1 mM) by 1.0 mM oximes and calculated percentages of oximate anion and neutral species at pH 7.4 are al so given as well as volume and surface area of R in the general oxime formula HOONCHC(O)NH—R. Experiments were performed in duplicate at 37° C. in 0.10 M phosphate buffer, pH 7.4, * The approximate fobs values determined for 0.67 mM 2PAM were: 0.087 min (for paraxon (POX)), 0.16 min 1 (for sarin), 0.025 min 1 (for cyclosarin (CS)), 0.15 min 1 (for VX). The experimental uncertainty of individual constant determination in the screen was about 50%. Structures and initial screen of relative rate constants (/fobs) $f^{or}$ OP-hAChE reactivation of selected uncharged reactivators (0.67 mM) in comparison to cationic pyridinium aldoxime 2PAM.

In analyzing the alkylamine substituent attached to the 2-hydroxyimino acetamide, we distinguished two elements: the heterocycle "handle" and an intervening methylene "linker." Starting with the 2-hydroxyimino acetamido amine RS 157A (no linker), ethyl, M-propyl, and w-butyl linkers were introduced along with primary amine, dimethylamine, pyrrolidine, piperidine, azepane, azocane, and bridged, polycyclic handles. Small amine and dimethylamine handles did not prove helpful, resulting in largely inactive reactivators (the last four compounds in Table 1, illustrated in FIG. 3) irrespective of the associated linker length. Both ethyl and propyl linkers proved effective.

Of four pairs of compounds containing an identical handle, the ethyl linker proved more efficient in two pairs (RS 194B versus RS194C and RS41A versus RS69L) and the propyl linker in the other two pairs (RS251B versus RS251A and RS191E versus RS69N). Overall, the most effective reactivators were RS194B and RSI 9 IE where RS41A structure was extended either through linker or handle size, but combining both longer linker and larger handle (as in compound RS194C) was not productive. The further increase in handle size to either an eight-membered azocane ring (RS251A and RS251B), bridged azepane (RS218A), or seven membered rings (RS2-57B) or by making it bicyclic yielded a respectable but not superior reactivator.

Analysis of molecular volumes and solvent-accessible surface areas for the N substituents (Table 1, or FIG. 3) suggests that the most efficient reactivators fall in the group of those having volume/surface area ratio between 0.87 and 0.92, suggesting that for this series of relatively similar compounds, a more spheroid rather than planar shape appears more productive. Intrinsic reactivities of all 16 compounds from Table 1 reflected in their measured rates of ATCh oximo lysis as well as the calculated percents of respective oximate anions were similar, emphasizing the importance of the shape and charge distribution for the productive interaction with OP-AChE conjugates leading to recovery of enzyme activity.

Reactivation Kinetics of Selected Oximes in Vitro

To distinguish whether molecular recognition or intrinsic chemical reactivity of RS41A was dominant in influencing overall reactivation potency, we analyzed reactivation kinetics of seven leading congeners of RS41A and three reference oximes, 2PAM, MINA, and DAM, and determined their individual reactivation constants $£¾$ and $K_{ox}$; see Table 2, or FIG. 4; and FIG. 5).

Table 2 describes: Kinetic constants for reactivation of paraoxon-, sarin-, cyclosarin-, VX- and tabun-hAChE conjugates by principal uncharged lead oxime RS194B initial lead RS41A, several oximes leading from RS41A to RS 194B, and reference oximes 2PAM, MINA, and DAM; and Maximal reactivation rate constant ($k_2$, min$^{-1}$), apparent dissociation constant of (oxime•OP-hAChE conjugate) reversible complex ($K_{ox}$, mm), and overall second order reactivation rate constant ($k_r$, M$^{-1}$ min$^{-1}$) were determined from reactivation curves as presented in FIG. 6. All constants were determined from triplicate experiments. S.E. of determined kinetic constants were typically less than 30% that of the mean.

Figure 36:
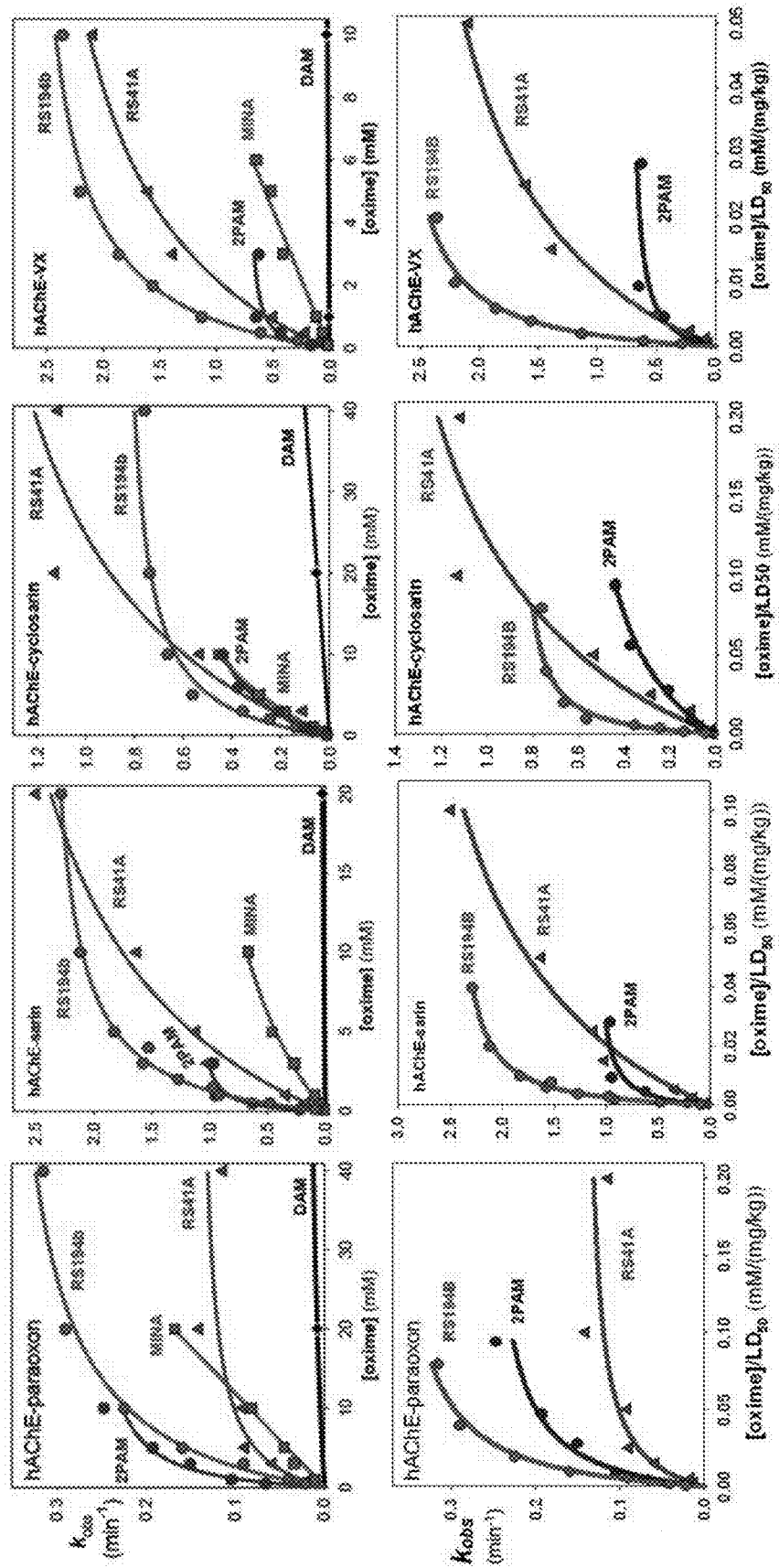
FIG. 36 graphically illustrates: Top panels, In vitro efficacy of the exemplary blood-brain-barrier penetrant oxime RS 194B for reactivation of OP-hAChE conjugates obtained by paraoxon, sarin, cyclosarin and VX (O-ethyl S-[2-(diisopropylamino)ethyl] methylphosphonothioate) inhibition; dependences of rates of reactivation on concentrations of RS194B, our initial lead RS41A and uncharged (MINA, DAM) or charged (2PAM) reference oximes; Lower panels: In vitro oxime efficacy corrected for in vivo toxicity of the each oxime; $LD_{50}$ values for i.m. administration to mice are 106 mg/kg, 200 mg/kg and 500 mg/kg for 2PAM, RS41A and RS194B, respectively, as discussed in detail in Example 1, below.
Figure 37:
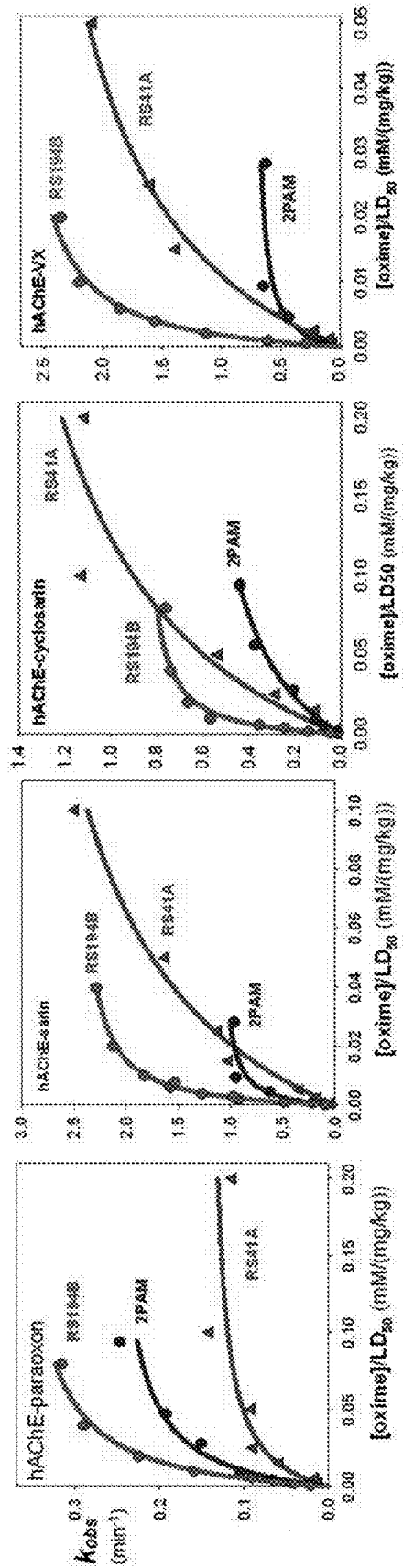
FIG. 37 graphically illustrates antidote indices for oxime re-activating agents; the Antidote Index is defined here by ([oxime]/$LD_{50}$); reactivation rates are found in FIG. 36.

FIG. 5 graphically illustrates the concentration dependence of oxime reactivation of sarin (A)-, VX (B)-, cyclosarin (Q-, paraoxon (D)-, and tabun (E)-inhibited (conjugated) hAChE. Dependence for the lead oxime RS194B (black circle) and the initial lead RS41A (open circle) compared with reference uncharged (DAM (gray diamond) and MINA (gray square)) and cationic (2PAM (gray square) oximes
(measured at 37° C. in 0.10 m phosphate buffer pH 7.4). See also FIG. 36.

In the analysis we assume that $K_{ox}$ mainly reflects initial reversible interaction of oxime reactivator with an OP-hAChE conjugate, whereas $k_2$ reflects the interaction of the reactivating oxime or oximate nucleophile with the phosphate moiety of the OP-conjugated hAChE in leading to the trigonal bipyramidal intermediate for reactivation. A pairwise comparison of six reactivators containing the identical handle and different methylene linkers reveals that trigonal bipyramidal intermediate for the oximate reaction prefers a shorter linker, whereas the initial reversible binding within the gorge appears frequently better for the propyl derivatives. Indeed, $k_2$ constants for the pairs RS194B versus RS194C, RS69N versus RS 191E, and RS41A versus RS69L were frequently larger in respective ethyl derivatives, whereas $K_{ox}$ constants appeared smaller in respective propyl derivatives, indicating stronger initial reversible interaction between an oxime and OP-hAChE. On the other hand, increases in the handle size from pyrrolidine to piperidine and azepane rings resulted primarily in smaller $K_{ox}$ values, whereas $k_2$ constants remained largely unchanged. One could thus conclude that enhancement of reactivation rates observed for RS194B versus initial lead RS41A results primarily from improved molecular recognition while preserving ability to form productive trigonal bipyramidal intermediate adducts. In further increasing size of handle from azepane to substituted tropane (RS 194B to RS218A), a similar trend of lowering $K_{ox}$ can be observed for paraoxon and sarin conjugates. However, due to simultaneous loss of reaction efficiency (reflected in reduced $k_2$ constants), the overall reactivation efficiency of RS218A was not greater than that of RS194B. Hence, RS194B oxime, an azepane analog of the initial lead RS41A, appears as a several fold better reactivator and significantly superior to the reference α-ketoximes, DAM and MINA, primarily due to enhanced molecular recognition of OP-hAChE conjugates.

pKg Determinations for Lead Oximes

The initial lead RS41A and the best uncharged reactivator RS 194B include at least two groups ionizable in the physiologically relevant pH range, affecting their reactivation potencies. Deprotonation of the oxime group is assumed to be essential for the oxime nucleophilic reactivity, whereas protonation of the handle ring nitrogen (azepane or pyrrolidine) should improve molecular recognition of a largely aromatic and partly anionic active center gorge of OP-hAChE adducts. Our goal was, therefore, to determine $pK_a$ values of both ionizable groups for both RS41A and RS194B oximes. Initially UV-visible spectroscopy was used to record change in UV spectra of both oximes in the pH range 1-13, see FIG. 6. The increase in absorbance of both compounds at 270 nm results from deprotonation of the oxime hydroxy 1, enabling us to determine a common $pK_a$ value of 8.8 for both compounds, see FIG. 12, Table 3).

Figure 6A:
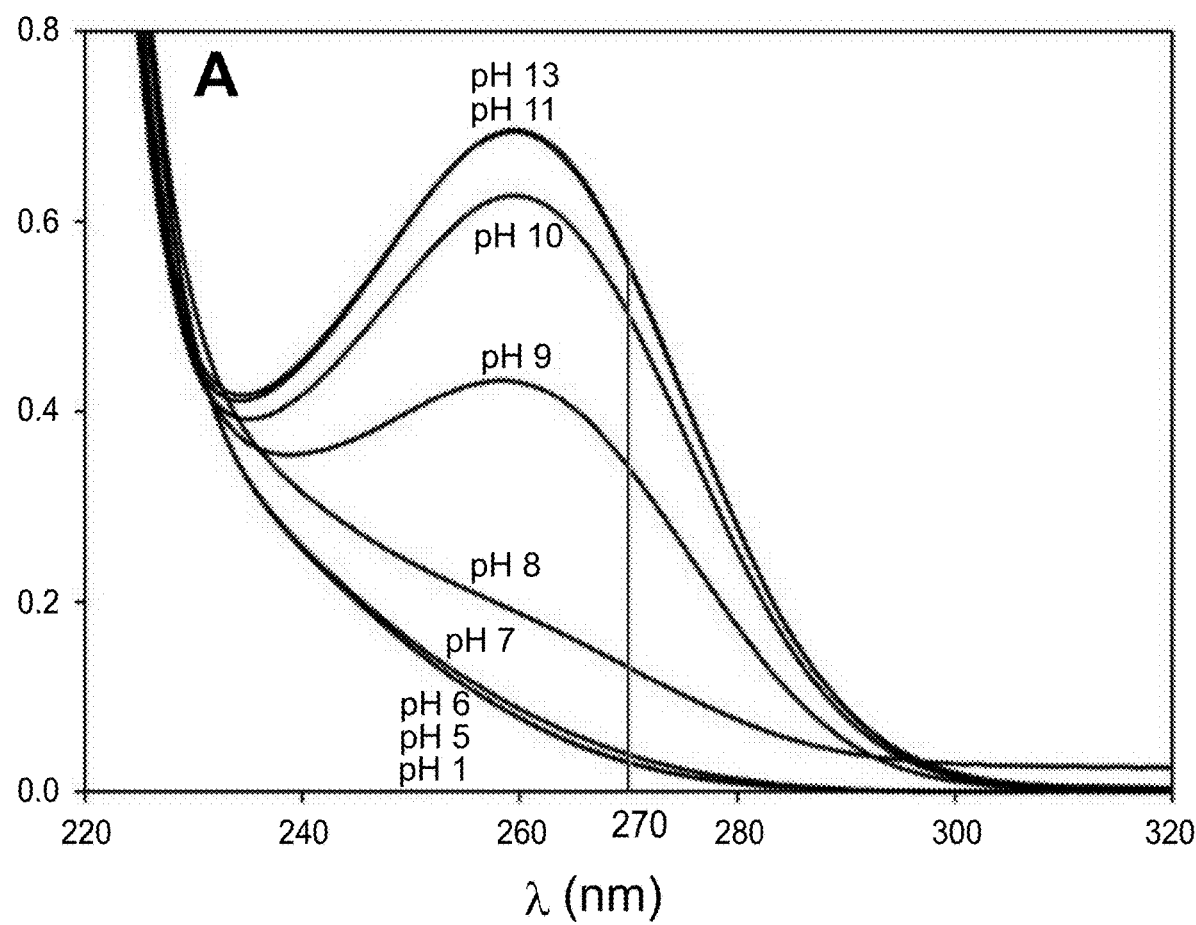
FIG. 6), oxime $^1$H NMR spectra in $D_2O$ (cf.
Figure 6B:
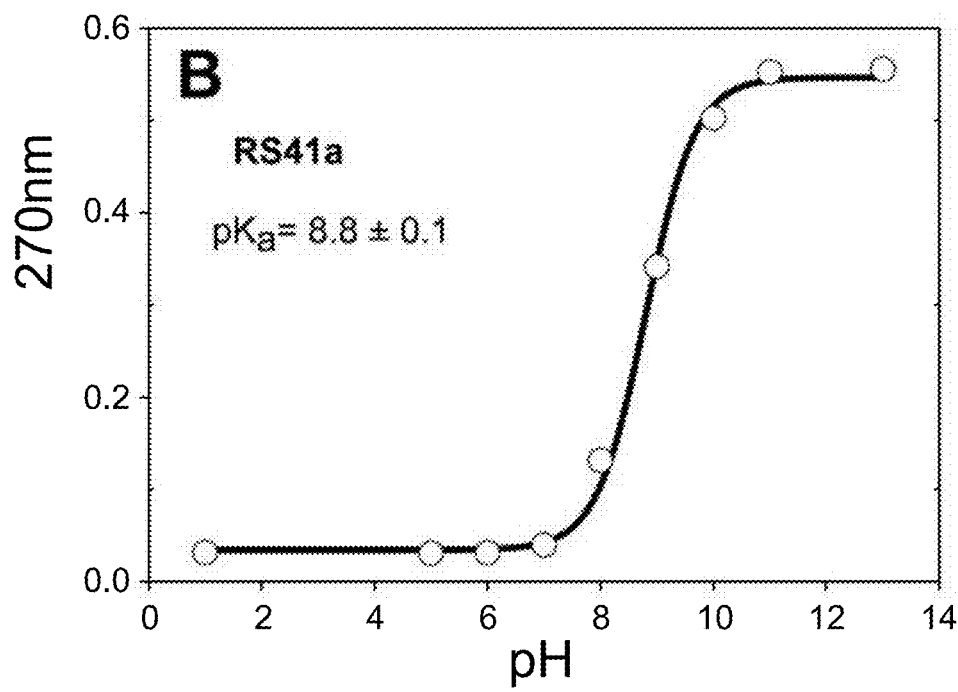
Figure 6C:
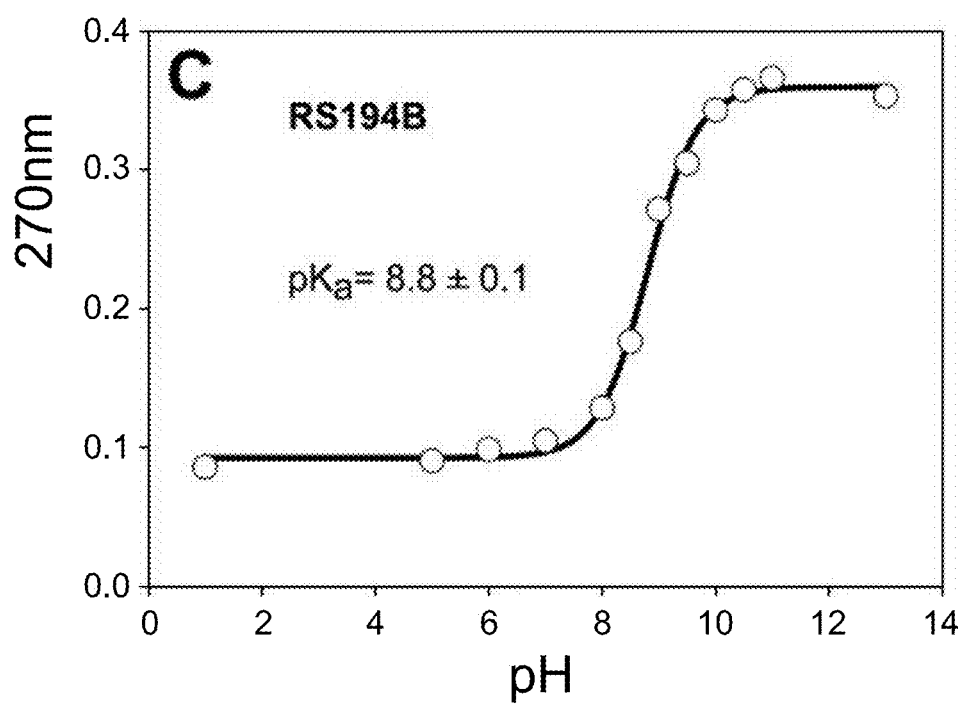

FIG. 6 graphically illustrates the pH dependence of UV spectra of 50μη RS41A and pH dependence of $A_{270}$ nm of 50 μM) RS41A (B), and RS194B along with corresponding $pK_a$ values calculated by nonlinear regression using Equation 1 (C).

Table 3 (illustrated as FIG. 12) describes a summary of $pK_a$ values for lead oxime RS194B and other selected oximes determined by four different techniques from pH-dependent changes in oxime UV spectra (cf. FIG. 6), oxime $^1$H NMR spectra in D2O (cf. FIG. 7), oxime-induced ATCh oximolysis and oxime-induced VX Flu-MP oximolysis.

FIG. 7 illustrates the pH dependence of $^1$H NMR spectra of 2.0 mm RS 194B in D$_2$O buffers (A, B, and C) along with corresponding $pK_a$ values calculated from the observed pH-induced difference in chemical shifts (D, E, and F) by nonlinear regression using Equation 1. NMR signals in panels A, B, and C were normalized relative to the maximal peak height in the given chemical shift region. Spectra were aligned using a benzene external standard singlet at 7.16 ppm.

Figure 22A:
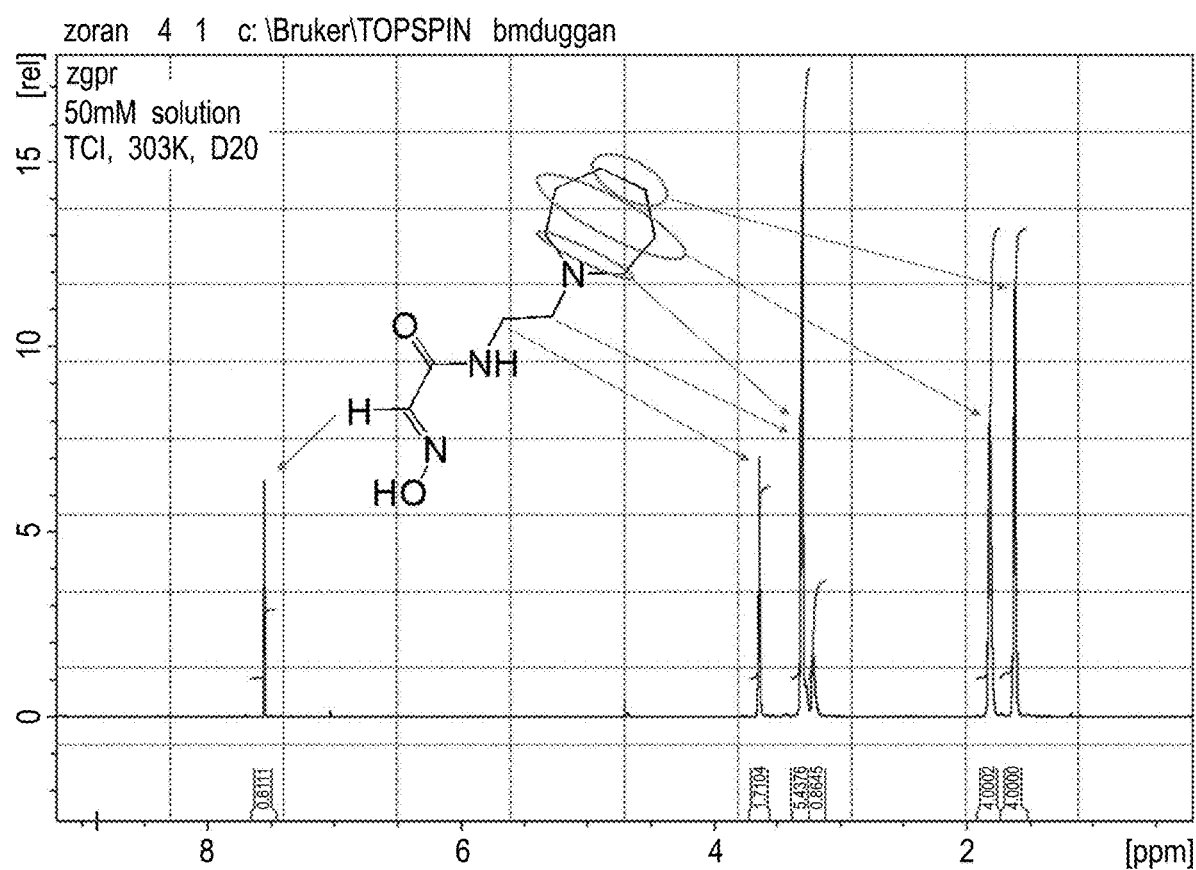
FIG. 22A-B illustrates the $^1$H NMR spectra of 50.0 mm RS194B in D2O buffer at pH 6.0.
Figure 22B:
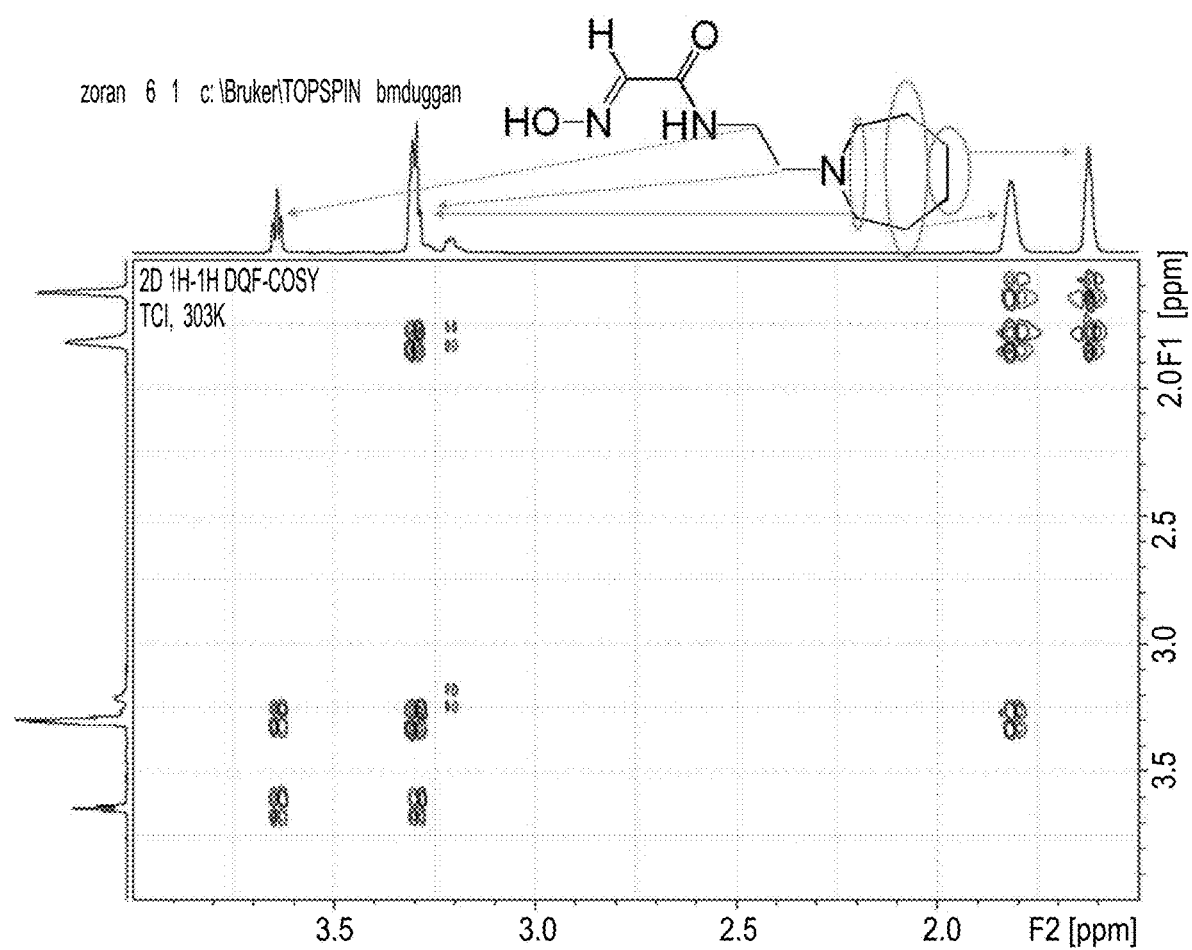
Figure 23A:
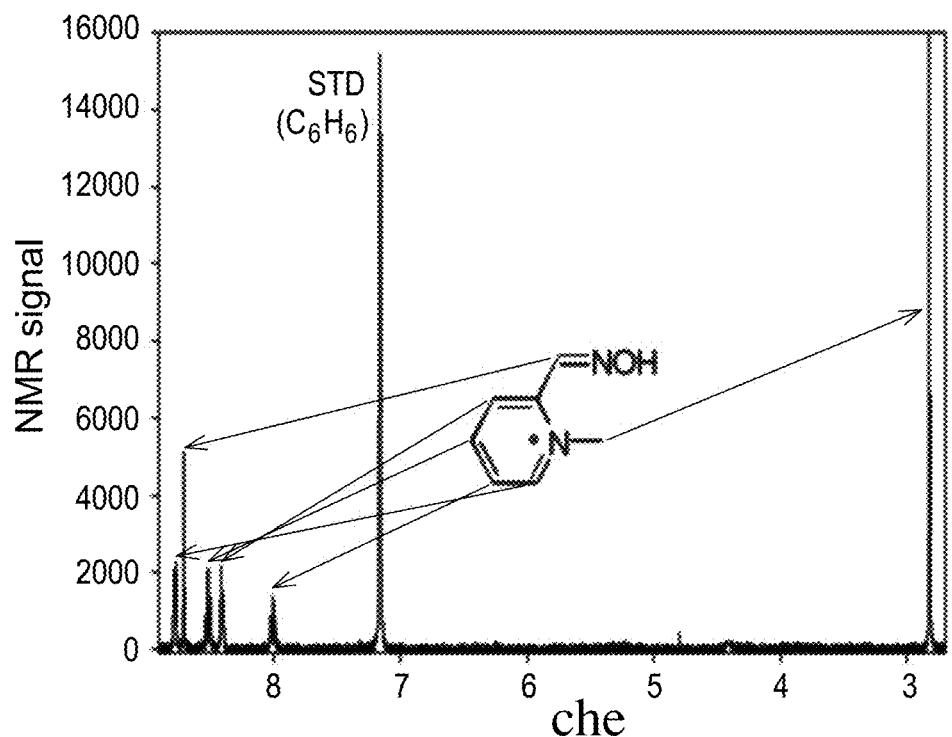
FIGS. 23A-F graphically illustrates pH dependence of $^1$H NMR spectra of 2.0 mM 2PAM in $D_2O$ buffers pH 5-10.
Figure 23B:
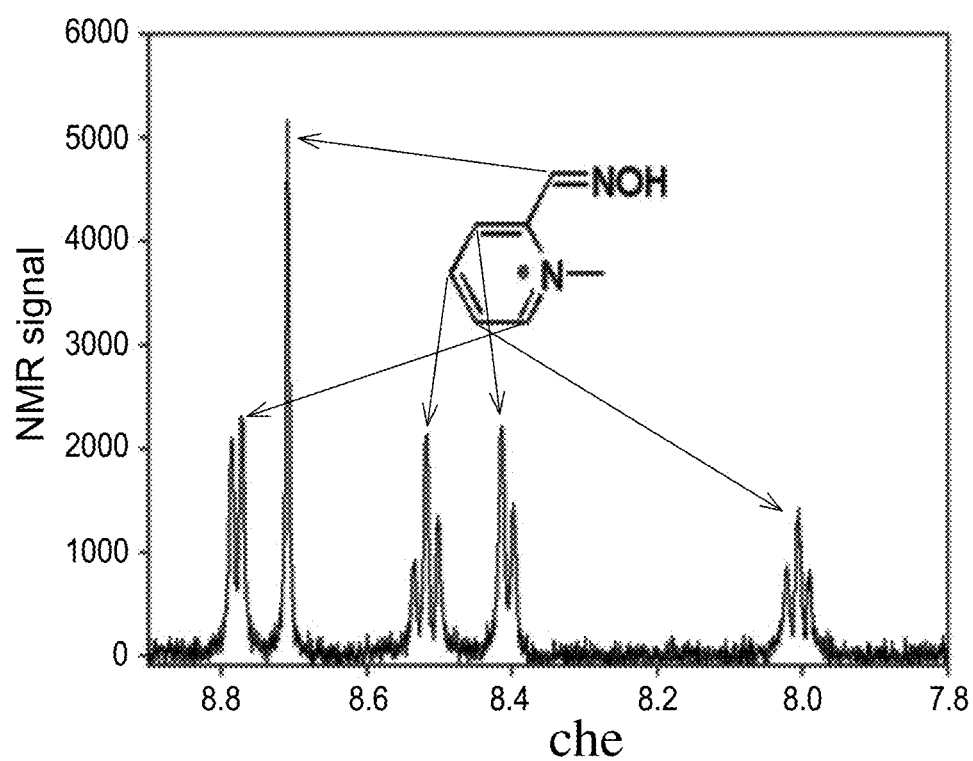
Figure 23C:
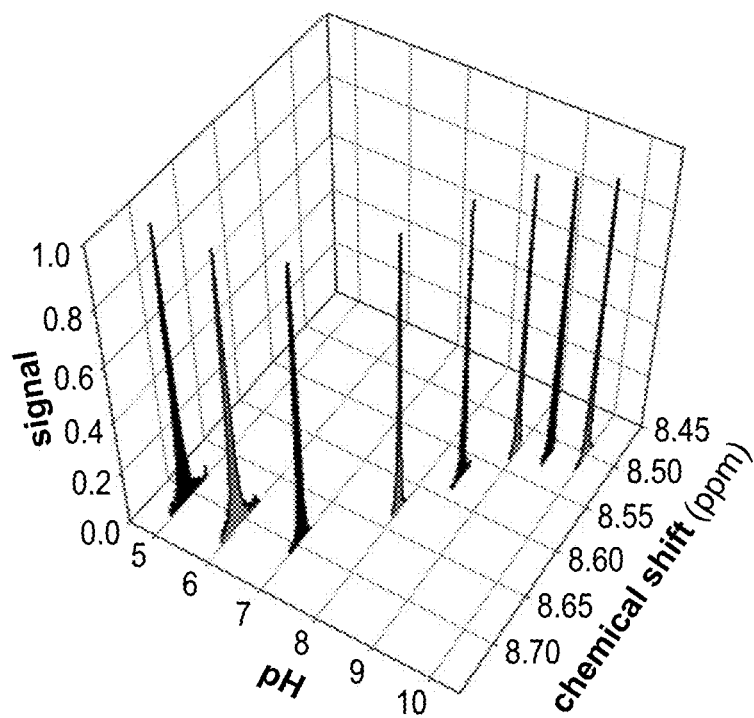
Figure 23D:
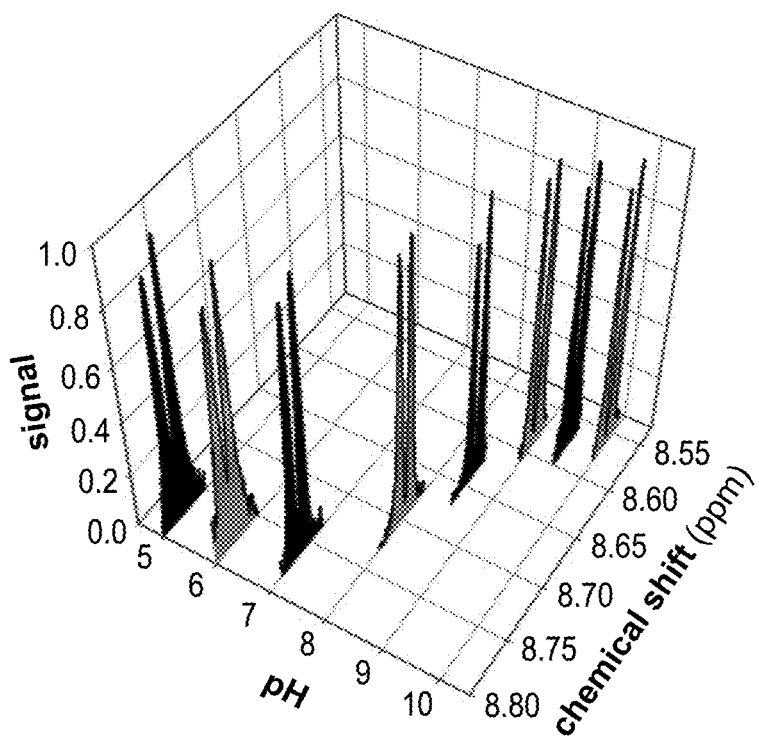
Figure 23E:
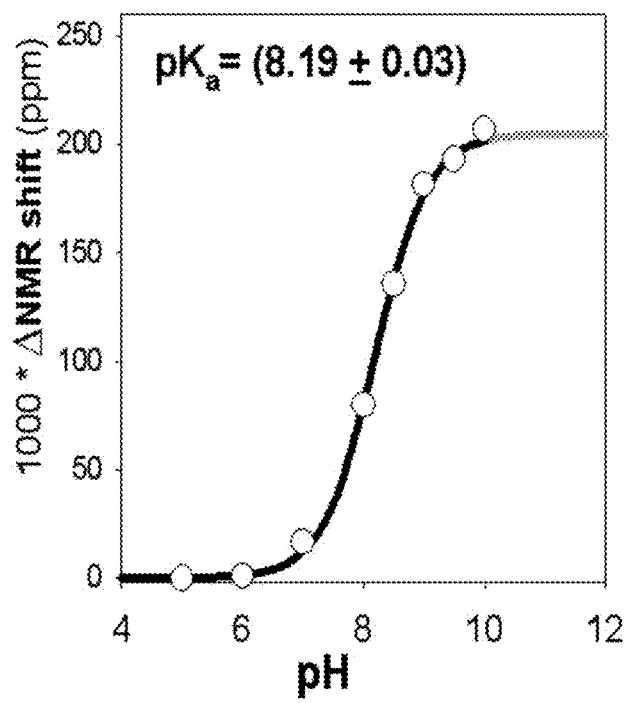
Figure 23F:
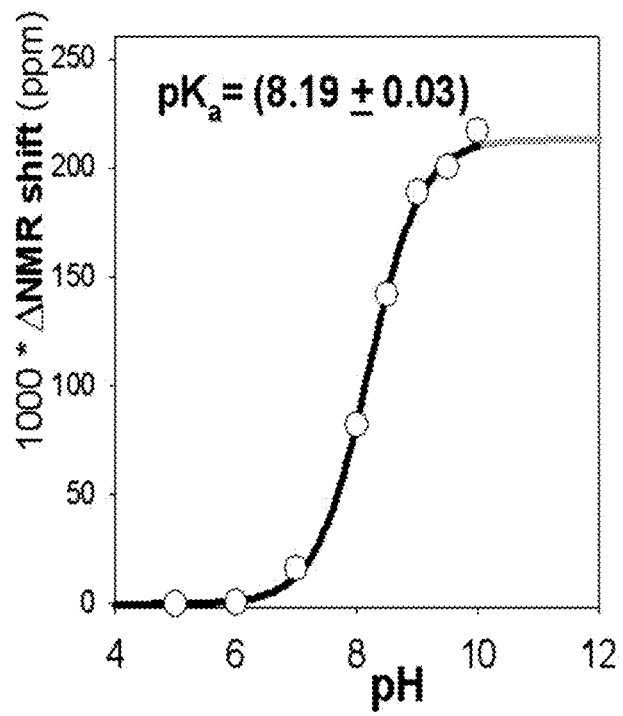

Ionization states of the lead reactivator RS194B and the reference oxime 2PAM were studied in more detail using $^1$H NMR spectrometry in D2O medium (FIG. 22 and FIG. 23) and FIG. 7). FIG. 22 illustrates the $^1$H NMR spectra of 50.0 mm RS 194B in D2O buffer at pH 6.0; FIG. 22A illustrates the integration-based peak assignment, an peak integrals are indicated; FIG. 22B illustrates confirmation of peak assignment by DQF-COSY spectrum (at a 1.5 to 4.0 ppm expansion) of the same solution; spectra were taken in 20 mM D2O phosphate-pyrophosphate buffer pH 6.0 containing 100 mM NaCl.

Figure 7A:
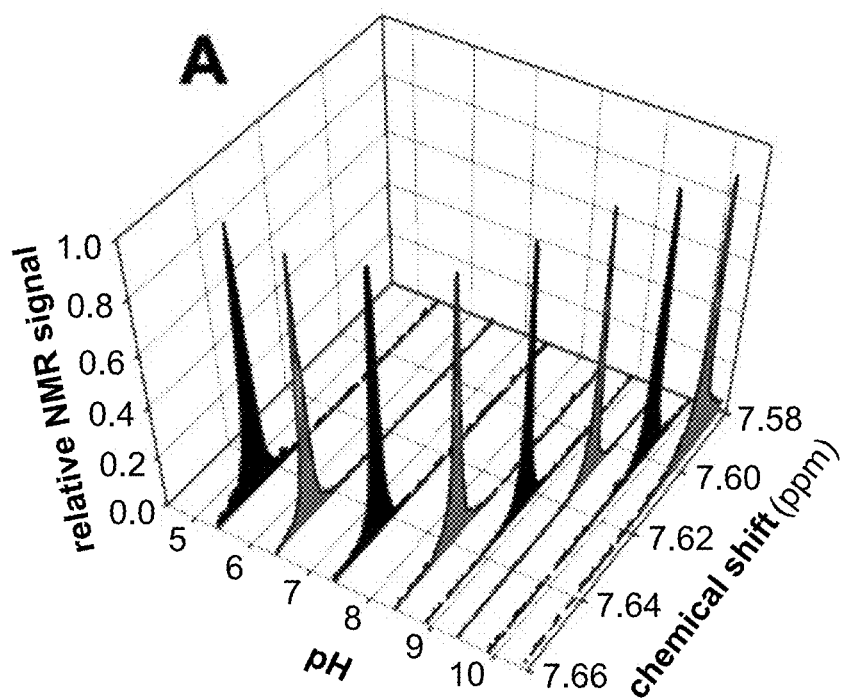
FIGS. 7A-F illustrates the pH dependence of $^x$H NMR spectra of 2.0 mM of the exemplary compound RS194B in $D_2O$ buffers (A, B, and C) along with corresponding $pK_a$ values calculated from the observed pH-induced difference in chemical shifts (D, E, and F) by nonlinear regression using Equation 1; NMR signals in panels A, B, and C were normalized relative to the maximal peak height in the given chemical shift region; spectra were aligned using a benzene external standard singlet at 7.16 ppm, as discussed in detail in Example 1, below.
Figure 7B:
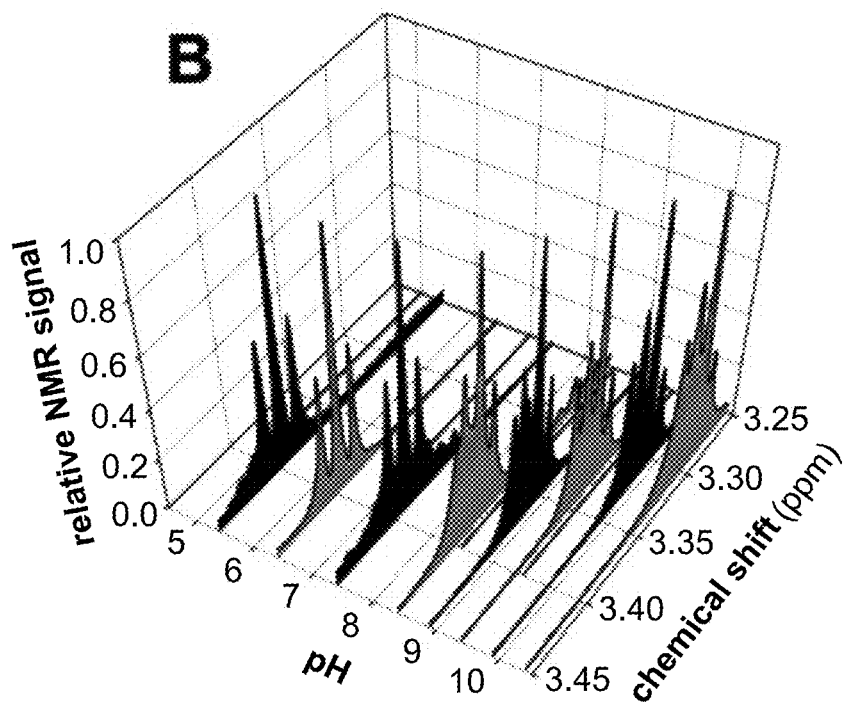
Figure 7C:
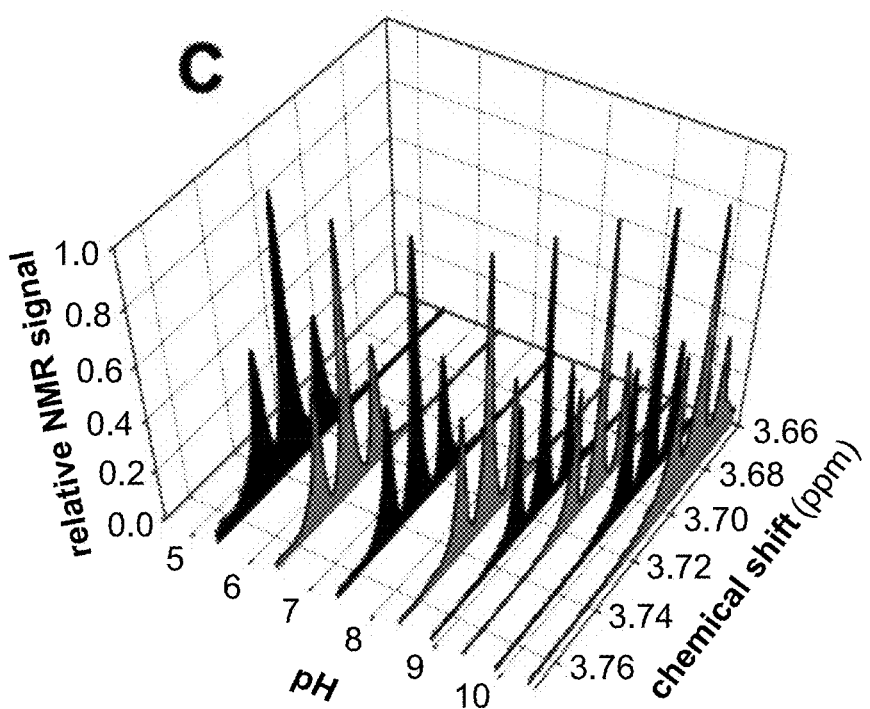
Figure 7D:
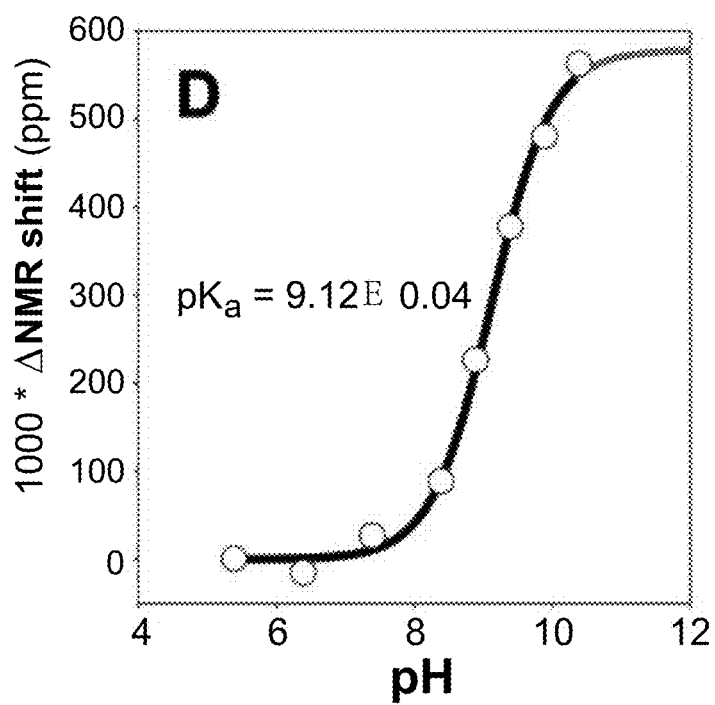
Figure 7E:
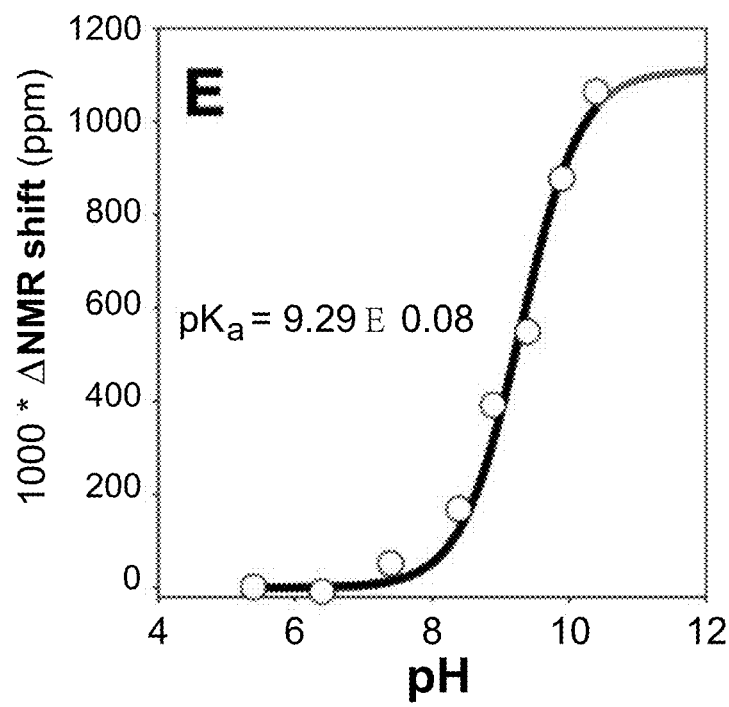
Figure 7F:
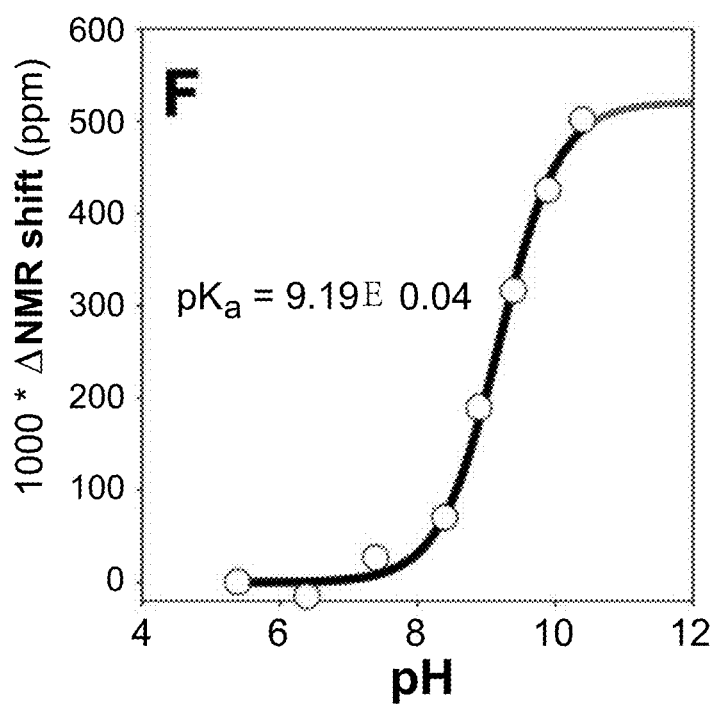
Figure 8A:
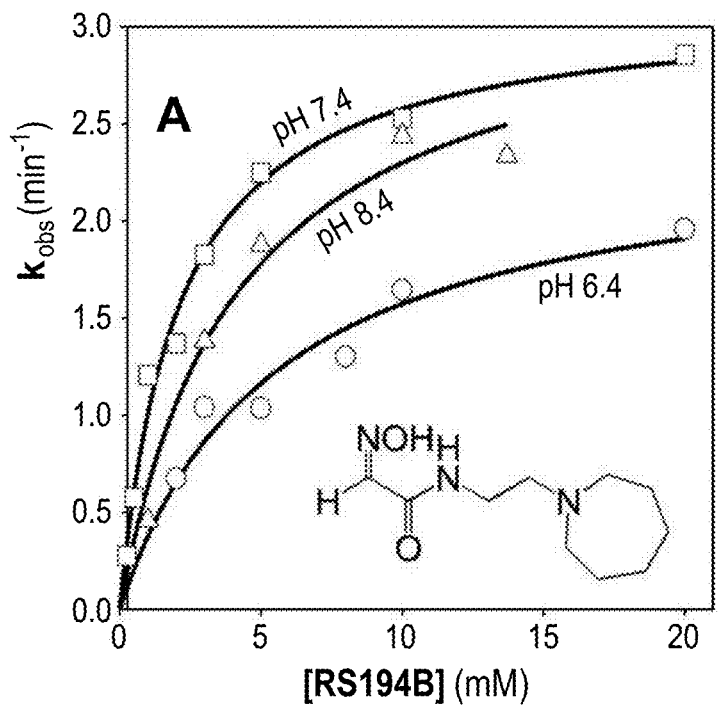
FIGS. 8A-D graphically illustrates concentration dependence of oxime reactivation of VX-inhibited hAChE by the exemplary compound, the lead oxime, RS 194B (A), initial lead oxime RS41A (B), and reference oxirane 2PAM (C) and the exemplary compound oxime RS186B (D) measured at pH 6.4 (o), pH 7.4 (□), and pH 8.4 (A) at 37° C. in 0.10 M phosphate buffers, as discussed in detail in Example 1, below.
Figure 8B:
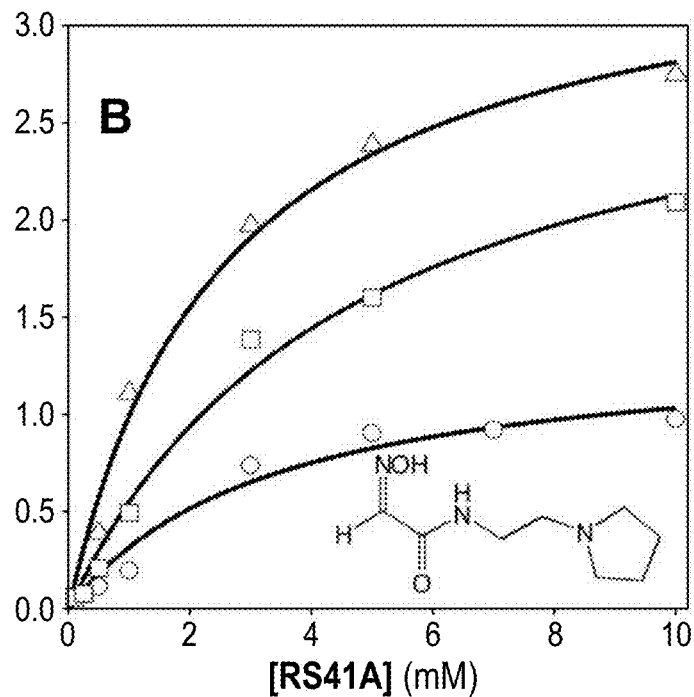
Figure 8C:
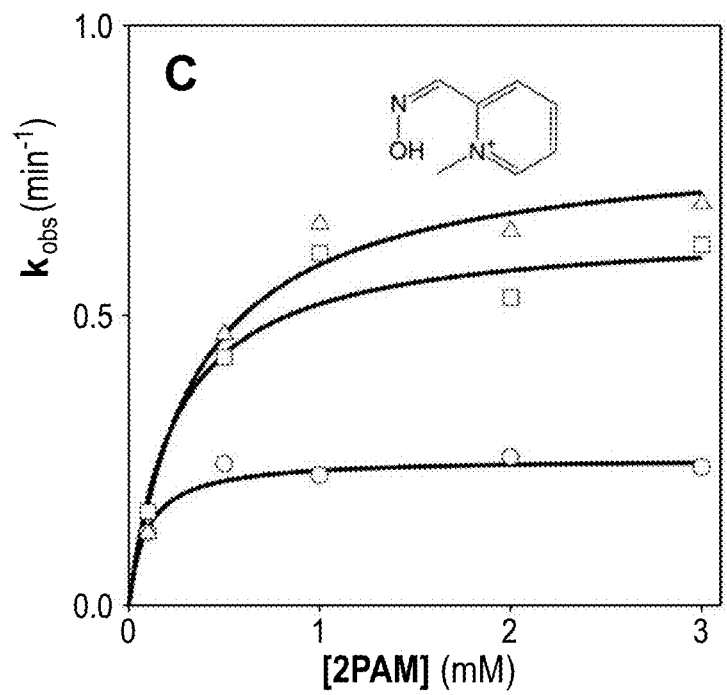
Figure 8D:
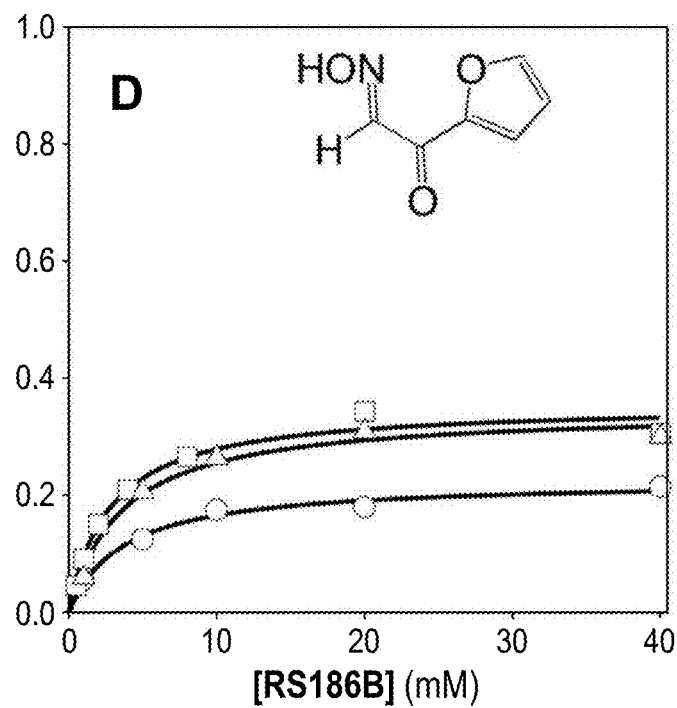

We focused on position and appearance of three peaks in the RS194B spectrum (FIG. 22), the amido H peak present at approximately 7.65 ppm at pH 7.0, and two triplets coming from protons surrounding the azepane nitrogen and appearing at approximately 3.37 ppm and approximately 3.73 ppm at pH 7.0. Peak assignments were confirmed using the double-quantum filtered COSY spectra
(FIG. 22B). Due to dissociation of the proton or deuteron, all three peaks shift to higher field at higher pH. The singlet at approximately 7.65 ppm shifts slightly to approximately 7.59 ppm at pH 10 (FIG. 7A). The triplet at
approximately 3.38 ppm shifts slightly to approximately 3.28 ppm at pH 10 and becomes a complex multiplet (FIG. 1B), whereas the triplet at 3.73 ppm shifts to 3.68 ppm (FIG. 1C). Plotting the change of chemical shift in D$_2$O as a function of pH yields three $pK_a$ values: 9.1 (equivalent to 9.1−0.5=8.6 in H$_2$O (see reference 27)) for loss of the imino hydrogen and $pK_a$ values 9.3 (8.8 in H$_2$O) and 9.2 (8.7 in H$_2$O) for the azepane and pyrrolidine protons on the nitrogens (FIGS. 7, D, E, and F; Table 3, FIG. 12). Both ionizable groups should be largely protonated at the physiological pH of 7.4, thus rendering a cation dominant over the neutral, zwitterion, and anionic species.

In the $^1$H NMR spectrum of 2PAM in D2O, both the aldoxime CH peak and peaks of all aromatic protons shift simultaneously as a function of pH (FIG. 23). As expected, only the N-methyl peak at 2.8 ppm did not shift (data not shown). This indicates that the ionization state of the oxime group affects derealization of aromatic system of 2PAM. This may influence the w-orbital interactions between the pyridinium ring and aromatic residues in the AChE gorge and consequently binding orientation of the reactivator. Analysis of pH-induced shifts of both the amido H peak (8.70 ppm at pH 7.0); and the doublet of aromatic proton at position 6 (8.75 ppm at pH 7.0); reveal a $D_2O$ $pK_a$ value of 8.6 (8.1 in $H_2O$) for the oxime group ionization (supplemental Table 3).

pH Dependence of Oxime Nucleophilicity

Figure 24B:
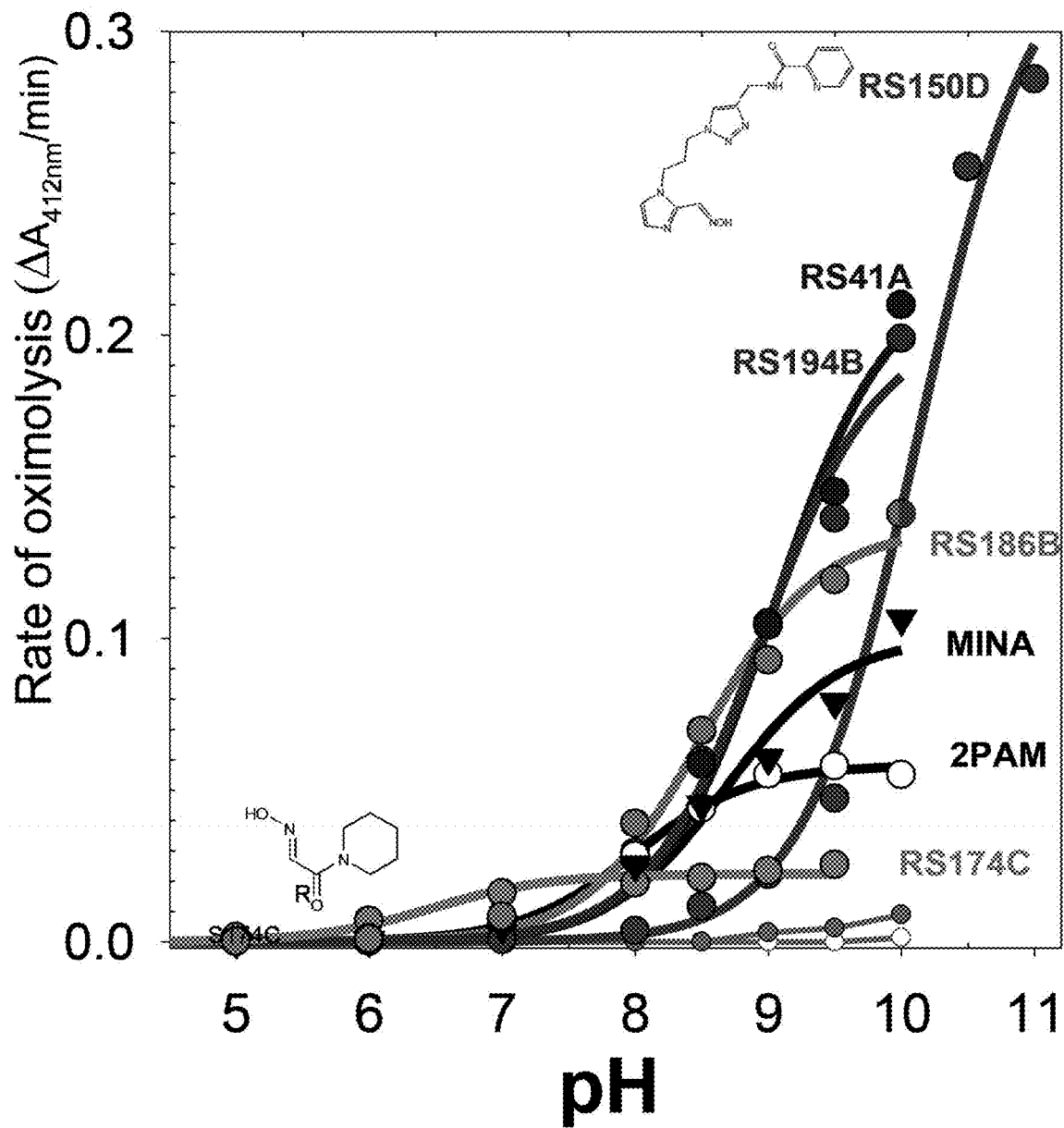
Figure 25:
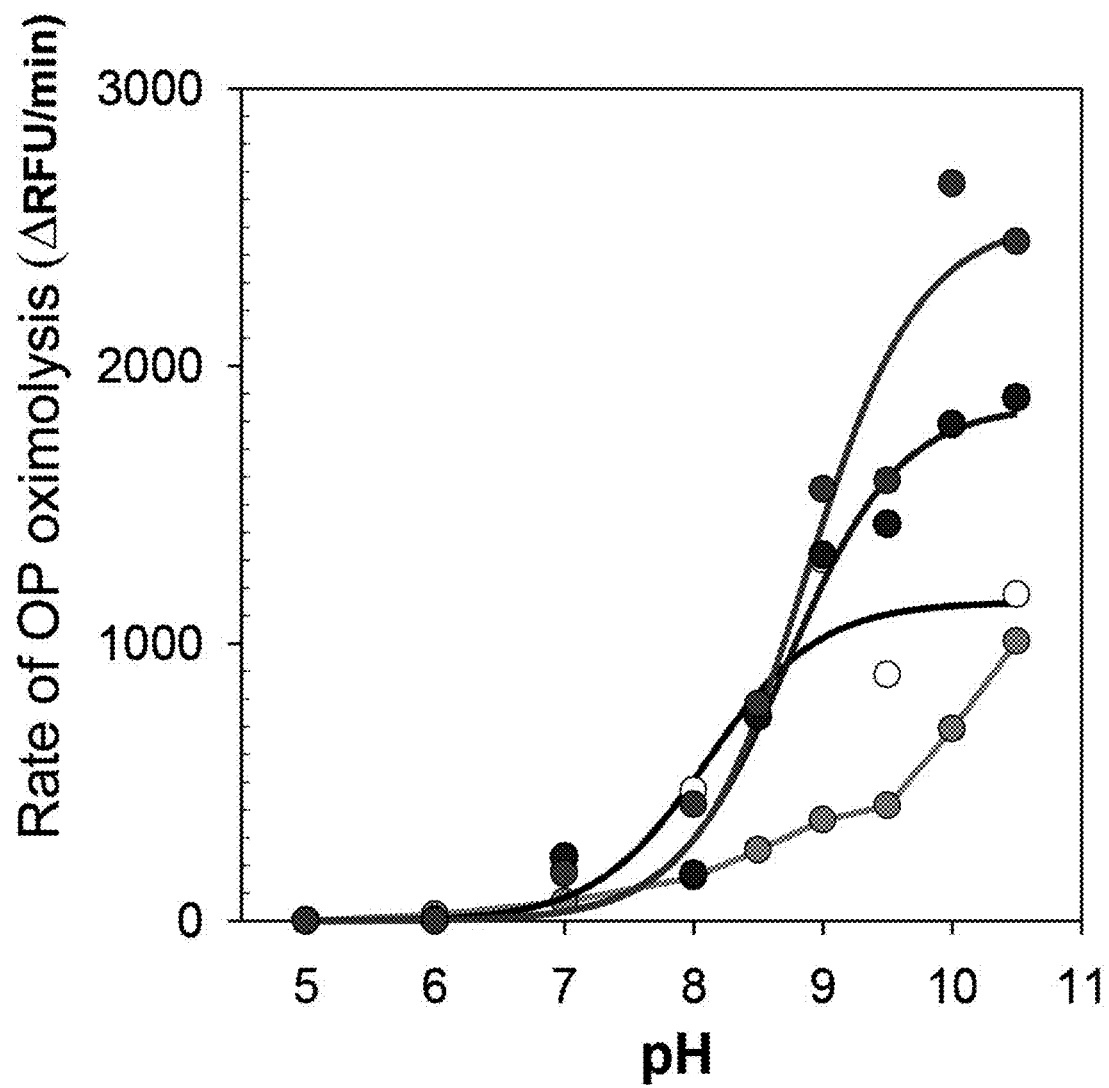
FIG. 25), as discussed in detail in Example 1, below.
Figure 26C:
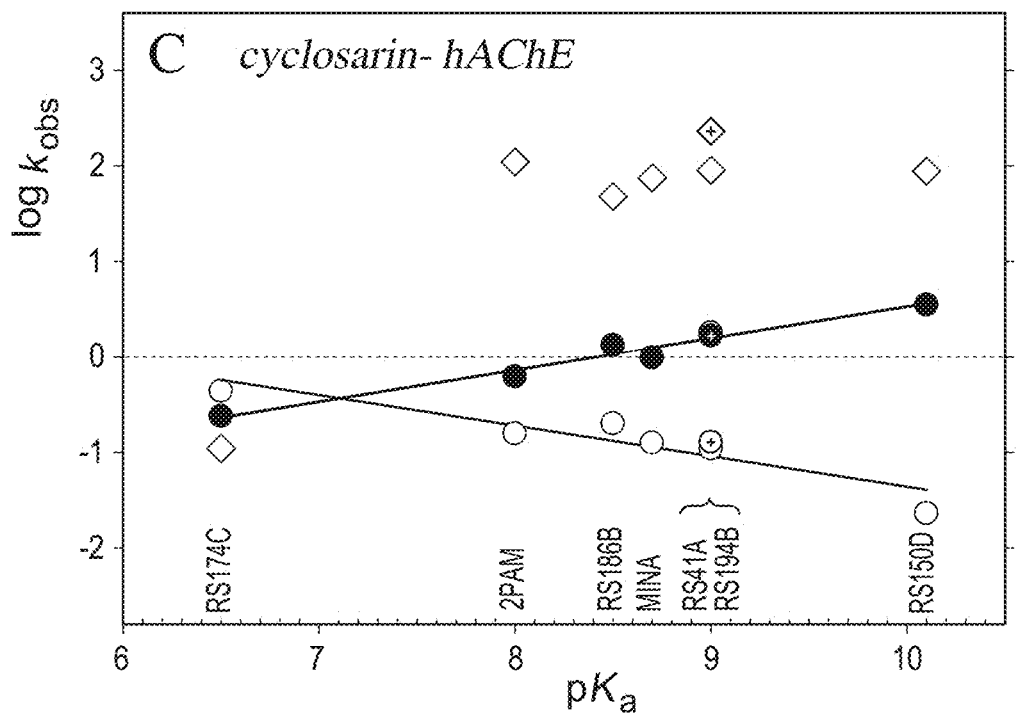
Figure 26D:
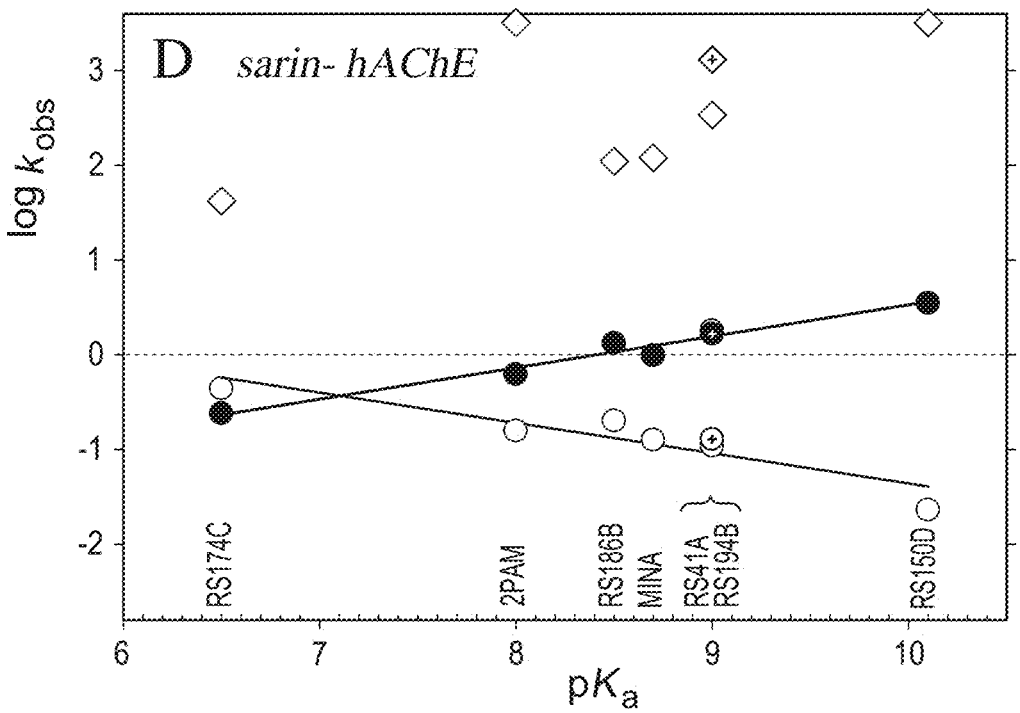
Figure 27A:
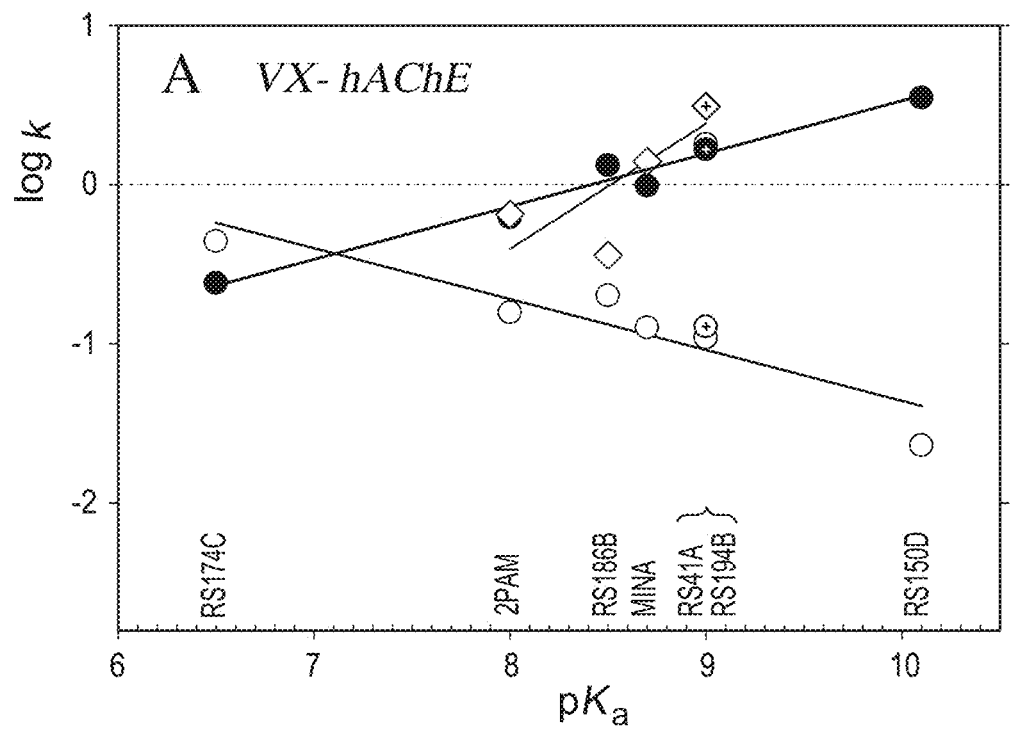
Figure 27B:
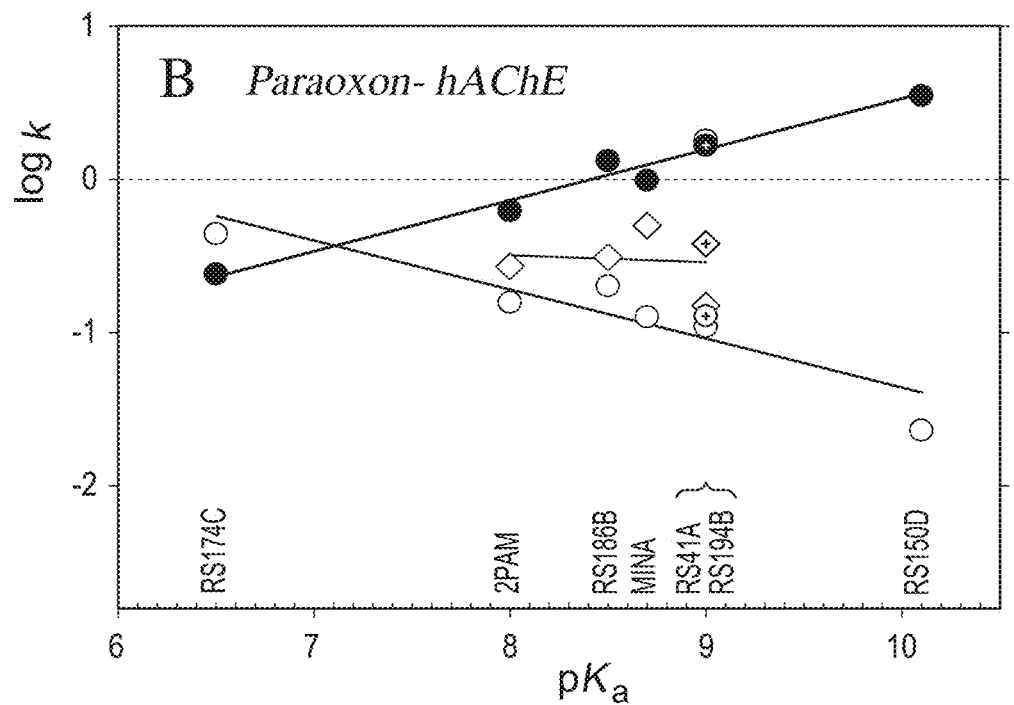
Figure 27E:
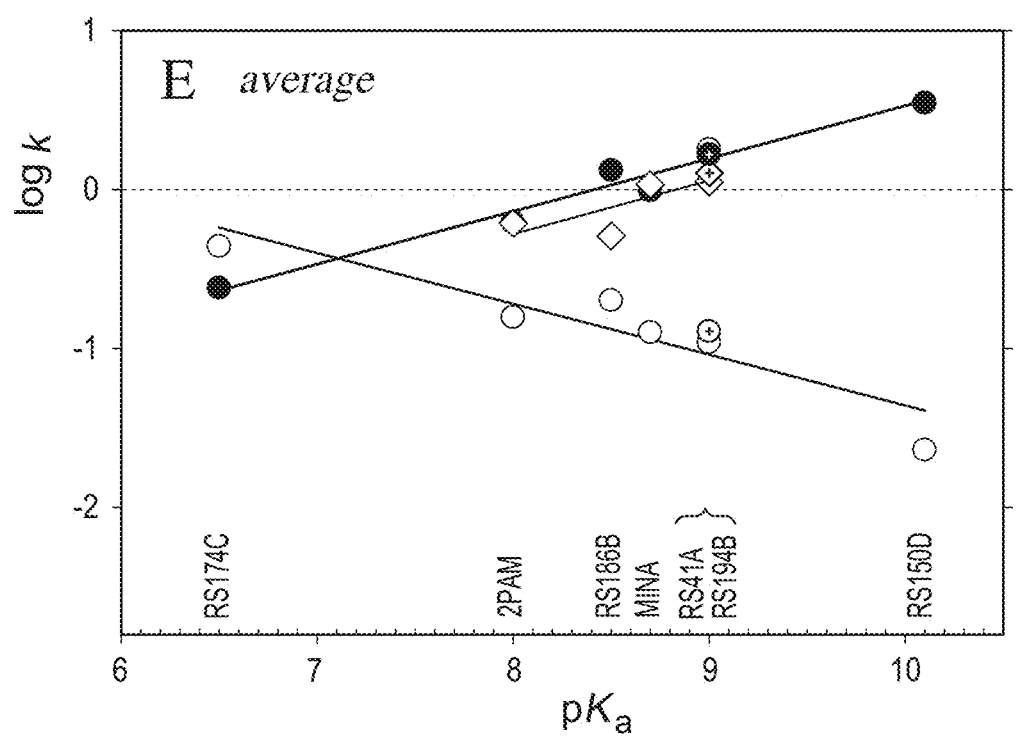

The rates of oxime-induced hydrolysis (oximolysis) of ATCh and Flu-MP analog of VX measured spectrophotometrically and spectrofluorometrically were considered to be a measure of nucleophilic reactivity of an oxime. The pH dependence of ATCh oximolysis by RS41A, RS194B, and 2PAM revealed respective $pK_a$ values of 9.0, 9.0, and 8.0 (supplemental Fig. S3, FIG. 24) and $pK_a$ values of 8.9, 8.7, and 8.1 for VX Flu-MP oximolysis (supplemental Fig. S4, FIG. 25), consistent with UV and $^1H$ NMR-based $pK_a$ determinations (Table 3). In supplementary FIG. 3 (Fig. S3; or FIG. 24), Reaction rates were measured spectrophotometrically at 22° C. in 20 mM phosphate-pyrophosphate buffers (containing 100 mM NaCl); and resulting pKa values calculated by nonlinear fit using equation (1) are given in this figure and in Table 3. In
supplementary FIG. 4 (Fig. S4; or FIG. 25), reaction rates were measured
spectrofluorometrically at 22° C. in 20 mM phosphate-pyrophosphate buffers (containing 100 mM NaCl); resulting $pK_a$ values calculated by nonlinear fit using equation (1) were: 8.9±0.1 (for RS194B); 8.7±0.1 (for RS41A) and 8.1±0.2 (for 2PAM). As expected, maximal oxime nucleophilicity was higher in oximates with higher $pK_a$ values. However, at pH 7.4, the oxime-oximate $pK_a$ comes into play where 2-PAM would have a greater nucleophilic capacity because of the greater fraction of oximate species.

pH Dependence of Reactivation Kinetics for Lead Oximes

Reactivation of VX-hAChE conjugate by RS41A and RS 194B oximes as well as by RS186B and 2PAM measured in 0.1 m phosphate buffers at pH 6.4, 7.4, and 8.4 reveals no systematic changes of the overall reaction rate (reflected in $k_r$ constant) (Table 4), whereas the nucleophilic first order reactivation rate constant $k_2$ did show a small increase with pH for all oximes. Consistent with its lowest $pK_a$ value, the increase in A % was largest for 2PAM. However, although molecular recognition of 2PAM, reflected in $K_{ox}$ constant, increased at lower pH, it did not change appreciably for the other two oximes. Thus, the protonated forms of both RS194B and RS41A oximes that dominate in large ratios at pH 6.4 as well as pH 7.4 with amine $pK_a$ values around 8.9 (Table 3) did not bind to VX-hAChE conjugate as well as cationic 2PAM. The presence of a
zwitterionic species at pH 8.4 (more than 50% of all forms for 2PAM and less than 50% for RS oximes) did not improve binding of RS oximes, whereas it slightly compromised binding of 2PAM (Table 4; FIG. 8).

Table 4 describes the Kinetic constants for reactivation of VX-hAChE conjugate by oximes RS 194B, RS41A, RS186B, and reference oxime 2PAM determined in 0.1 m phosphate buffers pH 6.4, 7.4, and 8.4.

FIG. 8 graphically illustrates concentration dependence of oxime reactivation of VX-inhibited hAChE by the lead oxime RS194B (A), initial lead oxime RS41A (B), and reference oxime 2PAM (C) and oxime RS186B (D) measured at pH 6.4 (o), pH 7.4 (□), and pH 8.4 (Δ) at 37° C. in 0.10 m phosphate buffers.

Acute Oxime Toxicity and Oxime Treatment of OP-Exposed Mice

The acute i.m. toxicity for mice of RS41A and in particular the lead reactivator RS194B was found to be relatively low (Table 5). Both oximes were less toxic than standard reference oxime 2PAM ($LD_{50}$=106 mg/kg), whereas RS194B was similarly toxic as HI-6 ($LD_{50}$=450 mg/kg) (data not shown), known as the least toxic standard oxime antidote.

Table 5 describes the therapy of OP-exposed mice with the exemplary compounds, the lead oximes, RS194B and RS41A and standard reference oxime 2PAM. Protective index is the ratio of OP $LD_{50}$ for OP-exposed animals treated with oxime (+atropine) and for animals given OP alone (cf. supplemental Tables S2-S6).

OP-exposed mice treated with 125 mg/kg of the exemplary compound RS194B (a dose roughly equivalent to 25% of its $LD_{50}$) recovered significantly better from OP exposure than mice treated with an equivalent dose of RS41A and notably better than animals treated with 2PAM, with paraoxon-exposed mice being an exception (Table 5). Treatment of VX-exposed mice with lower RS 194B doses equivalent to 10% of its $LD_{50}$ (50 mg/kg) and 5% of its $LD_{50}$ (25 mg/kg) yielded significant animal protection comparable with or better than 25% $LD_{50}$ dose treatment by 2PAM, emphasizing the unique therapeutic efficacy of the exemplary compound RS194B oxime (Table 6). Table 6 describes the combination of therapy and pretreatment of OP-exposed mice with the exemplary compound oxime RS194B at i.m. administered doses equivalent to 25, 10, or 5% its $LD_{50}$ dose of 500 mg/kg (cf supplemental Tables S2-S6).

Protective index is the ratio of OP $LD_{50}$ for OP-exposed animals treated with oxime and for animals given OP alone. Maximal dose of poison (MDP), a highest multiple of OP $LD_{50}$ fully counteracted by the oxime, is given in parentheses. Oximes in therapy (but not in pretreatment) were administered together with atropine. ND, not determined.

Pretreatment of mice with RS194B i.m., either 5 or 15 min before VX exposure provided notable protection effects only at the highest oxime dose applied (Table 6). However, a combination of 15-min oxime pretreatment and post-VX exposure therapy with 125 mg/kg RS194B produced an exceptionally high protective index of 45 and ensured survival of all mice against VX dose of 31.8 multiples of its $LD_{50}$ that equals 900 µg/kg of VX. Combining pretreatment with therapy enhanced RS 194B protective indices, albeit to a smaller extent, also for paraoxon, soman, and tabun (Table 6).

Oral administration (p.o.) of RS 194B oxime 15 min before OP, followed by an atropine i.m. injection 1 min after OP provided outstanding protection of VX exposed mice reflected in very high protective index (PI=40; FIG. 15A). Administering reference oxime 2PAM orally under equivalent conditions completely failed to protect mice exposed to VX (PI=1.1; Table 15A).

RS41A and RS194B Pharmacokinetics in Mice

Figure 9:
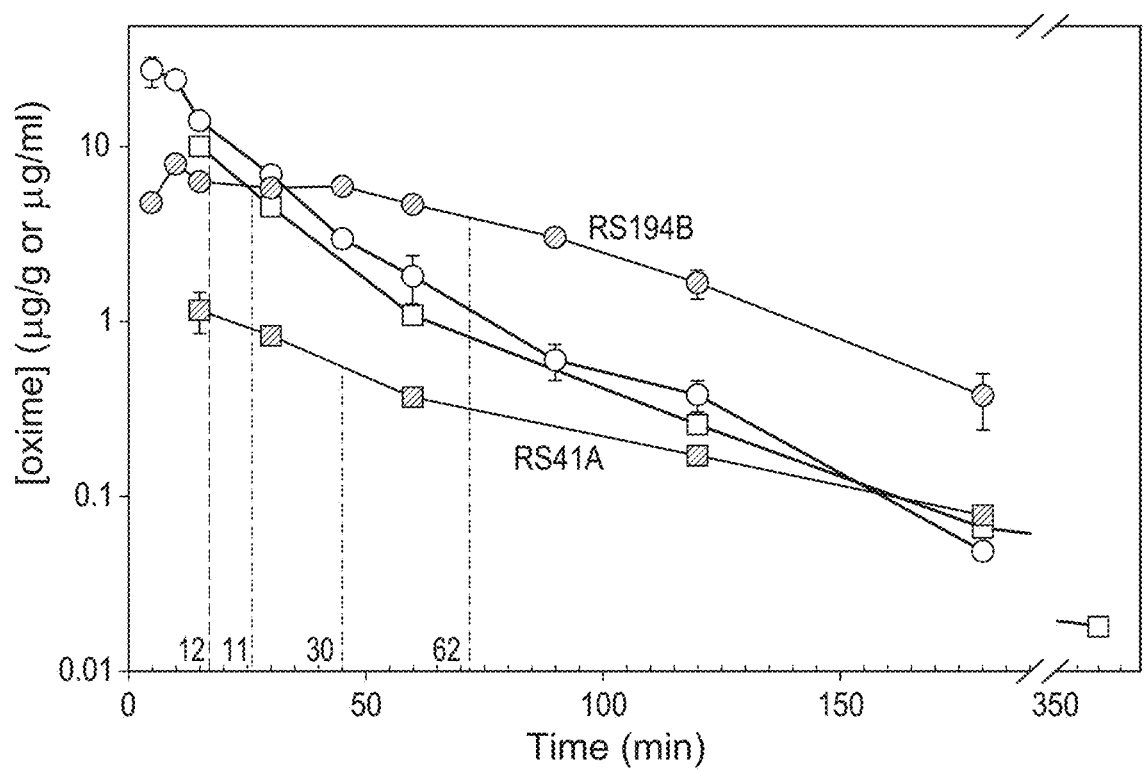
FIG. 9 describes the pharmacokinetics of the exemplary compound RS194B (circles) and the exemplary compound RS41A (squares) in mice; brain (gray lines) and plasma (black lines) compound concentrations were determined at discrete time points upon single, 80 mg/kg (RS194B), or 30 mg/kg (RS41A) dose administered to mice i.m.; each point represents average of determinations from three mice. S.E. of determination are indicated by error bars; times required for halving maximal compound concentrations in plasma and in brain are indicated by dashed lines for each of two oximes, as discussed in detail in Example 1, below.

Upon i.m. administration of a single dose of 80 mg/kg RS194B or 30 mg/kg RS41A, maximal concentrations determined in plasma were 10 and 27 µg/ml, respectively (equivalent to 54 and 125 pin) observed at the initial collection time point (FIG. 9; supplemental Table SI). The time needed for maximal plasma concentrations to decay by half was 11 min and 12 min for RS41A and RS194B, respectively. The decay kinetics over this interval likely reflects the distribution into tissue from the plasma as well as total body elimination. The distinctly non-first order elimination of the RS compounds from plasma is consistent with a multicompartmental analysis. Both compounds rapidly penetrated the blood-brain barrier. Maximal brain concentrations determined as 1.2 and 7.9 µg/ml (approximately 6.5 and approximately 37 µM), respectively, for RS41A and RS194B, reduced in half in 30 and 60 min. RS194B established between 15 and 40 min post-administration an apparent steady state concentration in brain, presumably due to the increased rate of brain accumulation, and plasma declines in concentration (supplemental Table S I).

FIG. 9 describes the pharmacokinetics of RS194B (circles) and RS41A
(squares) in mice. Brain (gray lines) and plasma (black lines) compound concentrations were determined at discrete time points upon single, 80 mg/kg (RS 194B), or 30 mg/kg (RS41A) dose administered to mice i.m. Each point represents average of determinations from three mice. S.E. of determination are indicated by error bars. Times required for halving maximal compound concentrations in plasma and in brain are indicated by dashed lines for each of two oximes.

The resulting brain/plasma ratios at the $t_{max}$ were thus significantly. 2-3-fold higher, for RS194B (0.30) than for RS41A (0.12). Brain levels of both oximes, in particular RS194B, at the final time point (180 min; FIG. 9) were higher than plasma concentrations, suggesting that elimination from this tissue lagged compared with systemic peripheral clearance.

Figure 16:
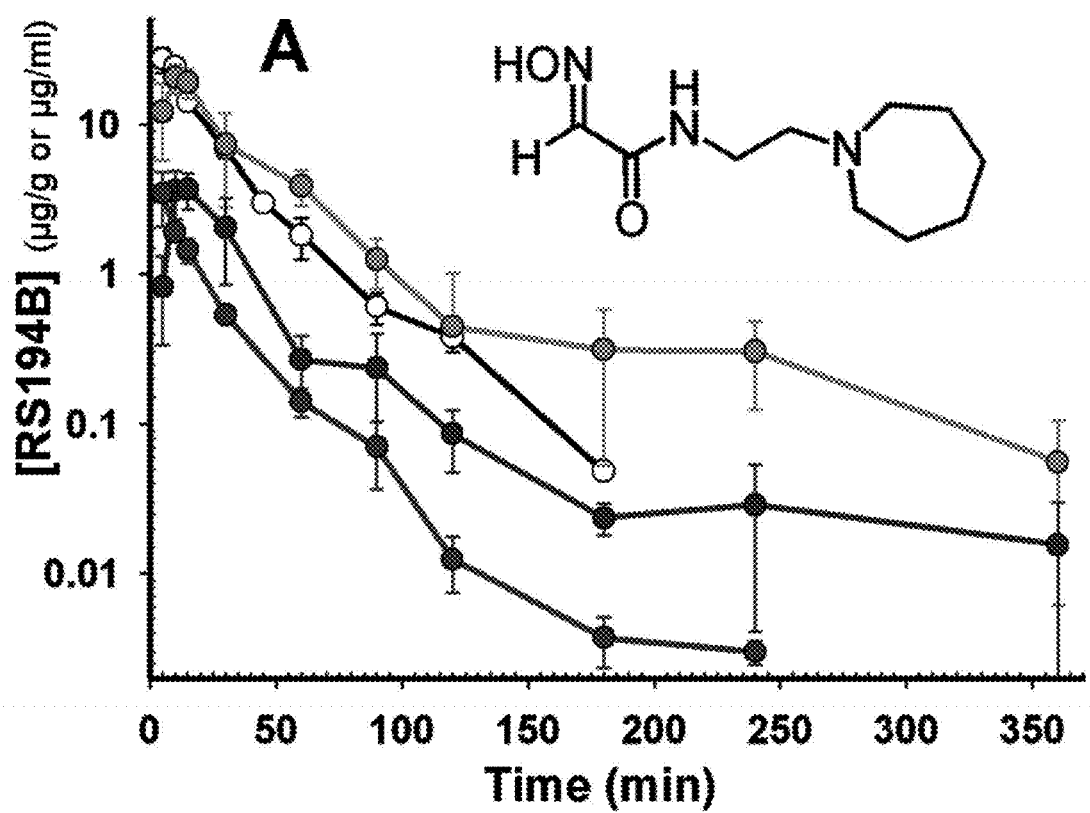
FIG. 16 graphically illustrates data showing the plasma kinetics in mice following intravenous, intramuscular and oral dosing; and, PK profiles of the exemplary RS194B (structure illustrated) concentration in plasma following various routes and doses of administration to the mouse, as discussed in detail in Example 1, below.

FIG. 16 graphically illustrates data showing the plasma kinetics in mice following intravenous, intramuscular and oral dosing. The important point here is the rapid oral absorption reaching peak plasma levels in 20 to 30 minutes. Decay is also rapid. PK profiles of RS 194B (structure illustrated) concentration in plasma following various routes and doses of administration to the mouse.

FIG. 17 illustrates data showing the bio-availability parameters. These are not very accurate; nevertheless they show oral absorption to be approximately 60% or better. Bioavailability of RS 194B (F) estimated from pharmacokinetic (PK) parameters determined upon intravenous and oral administration to the mouse. The Lethal Dose in 50% of the mice. Because of amounts of material and solubility we didn't go to higher ranges. Toxicity of RS194B determined upon intramuscular administration to the mouse: $LD_{50} \geq 500$ mg/kg.

Figure 18:
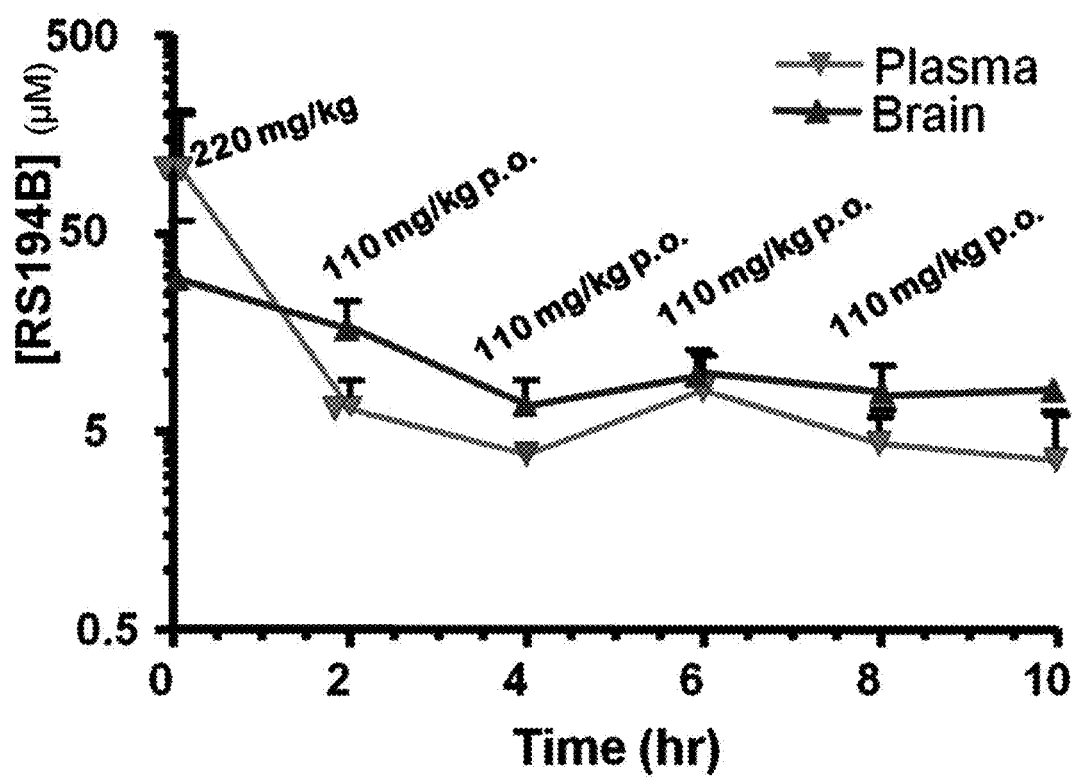
FIG. 18 graphically illustrates data showing an exemplary loading and maintenance dose scheme; the loading dose is given intramuscularly and the maintenance doses are given orally; PK profiles of the exemplary compound RS194B concentration in plasma and brain following loading oral dose of 220 mg/kg and subsequent maintenance oral doses of 110 mg/kg to the mouse, as discussed in detail in Example 1, below.

FIG. 18 graphically illustrates data showing a loading and maintenance dose scheme. The loading dose is given intramuscularly and the maintenance doses are given orally (gastric lavage as is the case in the previous FIG. 17). Plasma levels are measured before administration of the next maintenance dose. What this shows is that we can maintain a steady state concentration and would not see cumulative toxicity of the antidote. PK profiles of RS194B concentration in plasma and brain following loading oral dose of 220 mg/kg and subsequent (2 hr.) maintenance oral doses of 110 mg/kg to the mouse. Steady-state is reached with repetitive dosing. No signs of toxicity over this time period were noted, justifying considerably higher RS194B doses.

FIG. 19 illustrates data showing in vitro reactivation data for an antidote congener of RS 194B, RS 138B. Note that for the various organophosphates, it has comparable reactivation rates for both the phosphorate insecticides and the phosphonate nerve agents. A docking model of the compound within the active center gorge of acetylcholinesterase containing a conjugated organophosphate is shown. Kinetic constants for reactivation of paraoxon-, sarin-, cyclosarin- and VX-hAChE conjugates by RS2 138B, the principal uncharged lead oxime RS194B and reference oximes 2PAM, MINA and DAM. Reactivation rate constants $k_2$, $K_{ox}$ and $k_r$ were determined from the time dependence of OP-hAChE reactivation.

Figure 20:
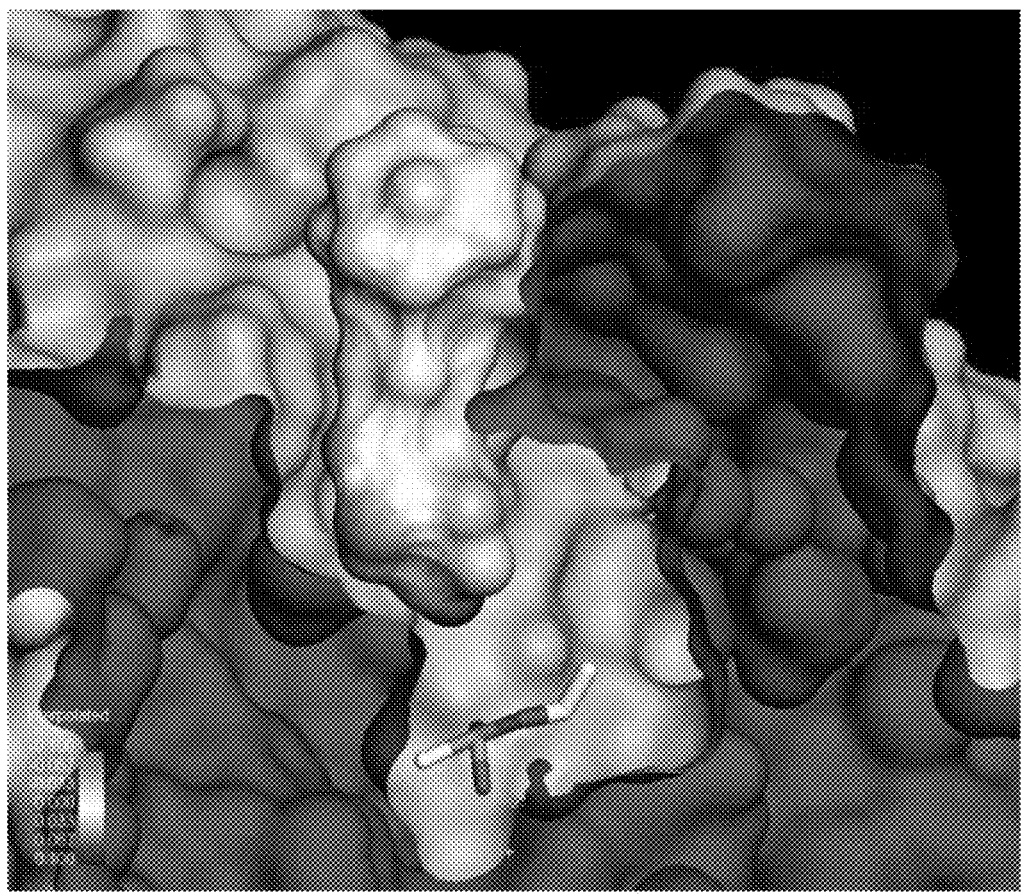
FIG. 20 illustrates an in silico computational molecular model of reversible binding for the exemplary RS138B to the VX-hAChE conjugate, characterized by $K_{ox}$; the ethoxy methylphosphonylated conjugated active serine side chain is rendered as orange (P) red (O) and white (C) sticks; the face of tetrahedral P atom open to nucleophilic oxime attack is facing the viewer, as discussed in detail in Example 1, below.

FIG. 20 illustrates an In silico computational molecular model of reversible binding for RS138B to the VX-hAChE conjugate, characterized by $K_{ox}$. One of preferred oxime conformations obtained by the modeling. The oxime structure represented by Connolly solvent accessible surface is colored by charge distribution (red—negative and blue—positive charge). Connolly surface of AChE is cut in half to reveal interior of the active center gorge (orange). The opposing side of the surface inaccessible to solvent is colored gray. Residues of the AChE peripheral site were allowed flexibility together with oxime, during computations. The ethoxy methylphosphonylated conjugated active serine side chain is rendered as orange (P) red (O) and white (C) sticks. The face of tetrahedral P atom open to nucleophilic oxime attack is facing the viewer.

FIG. 21 illustrates RS2 138B and RS194B. The In vitro reactivation potency of
RS2 138B makes it the most promising structural analog of the lead reactivator RS 194B. The In vivo therapeutic efficacy of RS2 138B in the VX exposed mouse is: the i.m. $LD_{50}$ in mg/kg is 238. The protective index is 10.8 (range is 9.1 to 12.7).

Discussion

The data presented herein are based on our recent revelation that 2-hydroxy imino acetamidoalkyl amines, although devoid of a permanent cationic charge, can efficiently reactivate OP conjugated hAChE in vitro (see reference 1). Formation of protonation equilibria around two ionizable groups in those oxime structures, an oxime group and an additional amine group, results in coexistence of charged, zwitterionic, and uncharged reactivator species around physiological pH values. Although zwitterionic and cationic species have the best chance of productive interaction with OP-hAChE conjugates, the
uncharged species can be expected to cross the blood-brain barrier delivering reactivator into CNS.

Our starting point for optimization was the structure of initially recognized lead hydroxyiminoacetamido alkylamine reactivator, RS41A. Introduction of systematic structural modifications in both its aliphatic linker and heterocyclic handle led to oxime structures with several fold improved potency for in vitro reactivation of four OP-hAChE conjugates culminating with new lead oxime structure RS 194B. Not only were we able to design a more efficient reactivator, but through detailed analysis of reactivation kinetics, we obtained insights into regulatory structural constraints imposed by varying geometries of OP-hAChE conjugates. Reversible binding of a reactivator leading to progressive reactivation is thus facilitated by propyl linker and a bridged azepane heterocycle, whereas optimal geometry of AChE-OP-oxime trigonal bipyramidal intermediate is achieved with ethyl linker. The greater in vitro reactivation rate of RS 194B is, therefore, largely a reflection of its improved molecular recognition, i.e. better binding to OP-hAChE conjugates as indicated by smaller $K_{ox}$ constants while maintaining similar A ¾ constants, in comparison to RS41A. This effectively means that improved oximeOP-hAChE interactions in the reversible complex were also preserved in the subsequent reaction trigonal bipyramidal intermediate. Computational molecular modeling of two reaction steps for RS41A and RS 194B oximes consistently reveals more pronounced similarity in geometries of reversible complex and trigonal bipyramidal intermediate for RS194B oxime and not with RS41A oxime (FIG. 10).

Additionally, modeling suggests that the main anchoring point of both RS41A and RS194B oximes in interaction with VX-hAChE is the aromatic amino acid cluster of the AChE peripheral site.

Figure 10A:
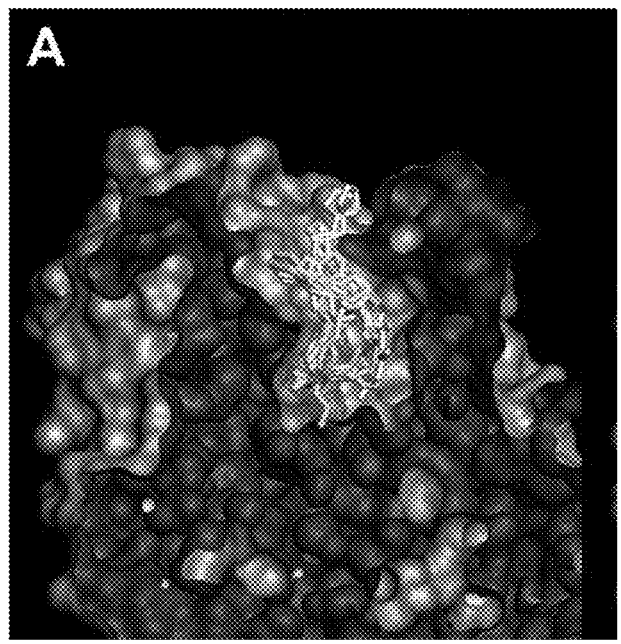
FIGS. 10A-B illustrates an image of a computational molecular modeling of VX-inhibited AChE showing the reversible Michaelis type complex and covalent pentacoordinate trigonal bipyramidal intermediate for interaction of initial lead oxime RS41A (A) and the exemplary compound, the lead oxime, RS194B (B), as discussed in detail in Example 1 below.
Figure 10B:
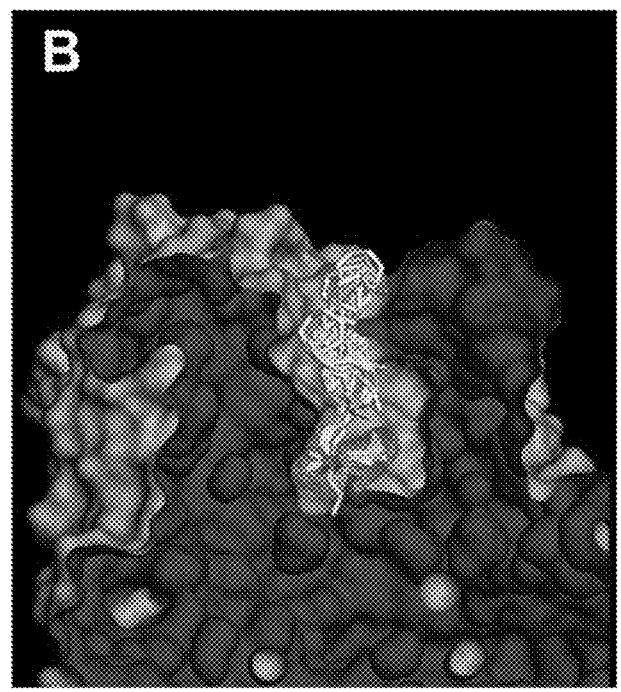

FIG. 10 illustrates an image of a computational molecular modeling of VX-inhibited AChE showing the reversible Michaelis type complex (white sticks) and covalent penta-coordinate trigonal bipyramidal intermediate (yellow sticks) for interaction of initial lead oxime RS41A (A) and the lead oxime RS194B (B). Ten conformers of each oxime are shown in each of two interaction states. The phosphorus atom is colored purple. The solvent-accessible part of the hAChE Connolly surface is represented in orange, and the solvent-inaccessible part of the hAChE molecule is in dark gray.

Pronounced overlapping similarity in global geometries of the reversible complex (white sticks) and trigonal bipyramidal intermediate (yellow stick) was observed for RS194B oxime, but not with RS41A oxime.

Analysis of ionization states of RS 194B by UV spectroscopy. $^1$H NMR spectrometry, and pH dependence of oximolysis reveals that both oxime group and amino group in the reactivator handle have $pK_a$ constants in the range between 8.6 and 9.0. At physiological pH 7.4, therefore, more than 90% of the compound exists in the protonated, cationic form. That seems to be reflected in reasonable in vitro reactivation kinetics where the initial reversible binding is improved for RS 194B versus RS41A (lower $K_{ox}$) while maintaining respectable reactivity (a small decrease in ki). A low fraction of oximate is thus counteracted by high nucleophilicity and preferred for CNS reactivators due to lower ionization of the oximate facilitating blood brain barrier penetration.

Figure 11:
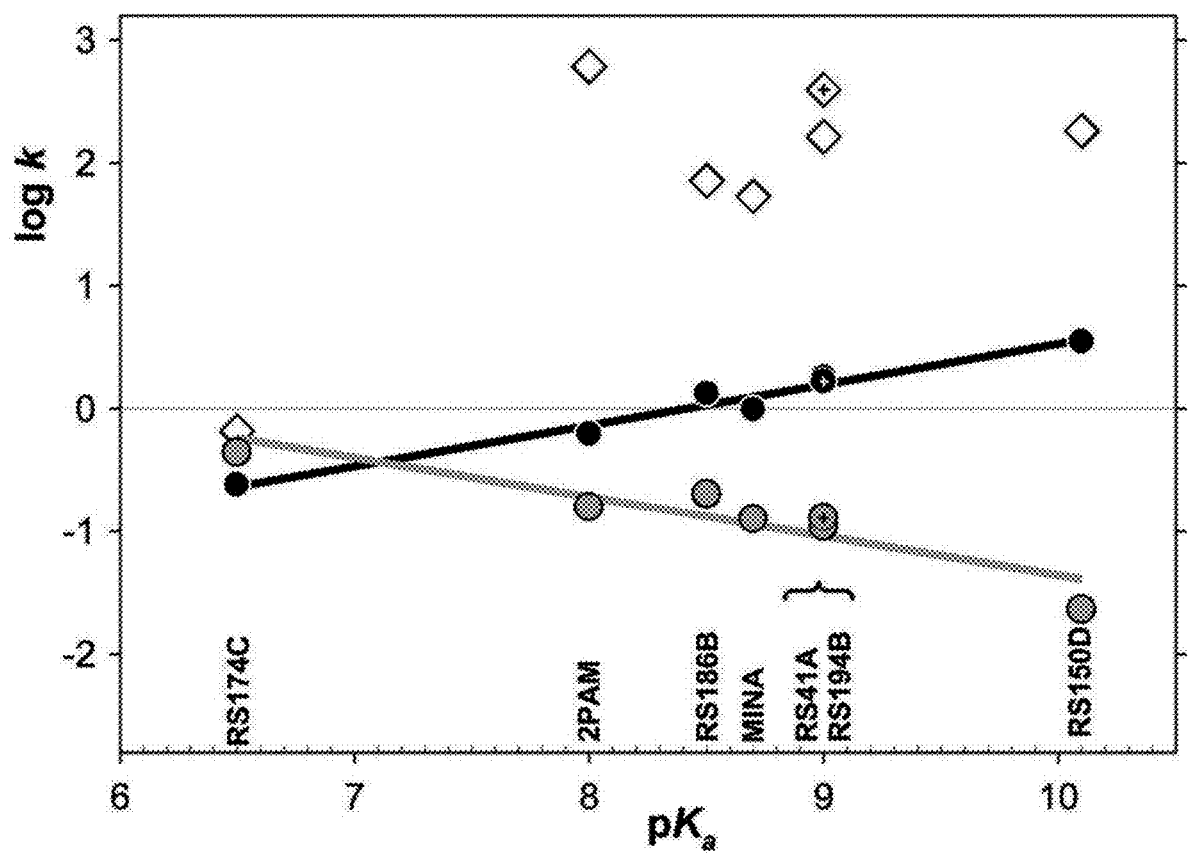
FIG. 11 graphically illustrates the free energy relationships between nucleophilic reactivities and oxime group ionization states of selected oxime reactivators. Rate constants (k) of maximal pH-dependent ATCh oximolysis (black line and circles), oximo lysis at pH 7.4 (gray line and circles), and an average overall rate constant $k_r$ ($M^{-1}$ $min^{-1}$) for oxime reactivation of VX, sarin, cyclosarin, and paraoxon inhibited hAChE (white diamonds) in relation to $pK_a$ values were determined for reactivator oxime groups, as discussed in detail in Example 1, below.

Despite the suggestion that reactivators with lower oxime $pK_a$ may be intrinsically more reactive at physiological pH in the absence of enzyme (FIG. 11 and, see Ref. 26), their overall reactivation potency expressed by constant $k_r$ was not found to correlate closely with the oximate $pK_a$ (in the wide $pK_a$ range 6.5-10.1) for reactivation of any of OP-hAChE conjugates analyzed individually or as an average (FIG. 11). The linear increase of the maximal rate of reactivation log with the increase in $pK_a$, observed for five studied reactivators, however, reveals a greater dependence of reactivator nucleophilic strength for reactivity of AChE-OP-oxime trigonal bipyramidal intermediate when compared with fractional availability of oximate anion at physiological pH determined by the oximate $pK_a$. This observation may indicate an effective proton extraction mechanism for oxime reactions in the hAChE active center gorge. On the other hand domination of the protonated amine at pH 7.4 influences the capacity of RS 194B to enter the CNS. Nevertheless, pharmacokinetic studies in mice indicate that both RS194B and RS41A oximes penetrate CNS quickly and can be found there at up to 37 and 6.5 pin concentrations, which are ~12-30% of corresponding plasma concentrations.

FIG. 11 graphically illustrates the free energy relationships between
nucleophilic reactivities and oxime group ionization states of selected oxime reactivators. Rate constants (k) of maximal pH-dependent ATCh oximolysis (black line and circles), oximolysis at pH 7.4 (gray line and circles), and an average overall rate constant $k_r$ ($m^{-1}$ $min^{-1}$) for oxime reactivation of VX, sarin, cyclosarin, and paraoxon inhibited hAChE (white diamonds) in relation to $pK_a$ values were determined for reactivator oxime groups. The lead reactivator RS194B data is indicated by cross-haired symbols. $k_r$ for RS174C and RS 150D (not extensively studied in this series) were extrapolated from reactivation rates determined at single (0.67 mm) oxime concentration.

Very good antidotal actions of RS194B in treatment of OP exposed mice relative to RS41A or 2PAM treatments undoubtedly result from its improved intrinsic reactivation potency combined with its lower toxicity and superior pharmacokinetic profile including faster CNS penetration and longer retention. However, a favorable antidotal action of RS194B was noticeable even at doses equivalent to 5 and 10% its $LD_{50}$ value. RS194B was most efficient in therapy of VX, sarin, and paraoxon exposed mice, where it was superior to both RS41A and to a standard reactivator 2PAM (except for paraoxon intoxication). Although RS194B, when given solely as a pretreatment modality, produced limited prophylactic protection to subsequent OP exposure, consistent with its relatively low binding affinity for AChE conjugates (large $K_{ox}$ values), the combination of pretreatment and therapy at the highest RS 194B dose resulted in outstanding antidotal efficiency reflected in the protective index of 45.

Oral therapeutic efficacy of RS 194B proved to be outstandingly consistent with excellent bioavailability of this compound determined in PK experiments. This critical observation allowed for the design of entirely new, previously unreported classes of oxime reactivator antidotes of the invention, all suitable to treat very large numbers of OP exposed populations in a pronounced non-invasive and cost-effective manner.

Several classes of novel compounds have been recently suggested as promising centrally active reactivators of OP-exposed hAChE. Two non-quaternary pyridine aldoxime phenyltetrahydroisoquinoline derivatives directed to interact with the AChE peripheral site showed outstanding potency for in vitro reactivation of VX and tabun-conjugated hAChE (see reference 2). Thus, uncharged, extended ligands with high affinities for the peripheral site form an alternative means of directing nucleophiles to the organophosphate conjugated active center (see reference 28). The overall second order rate constant ($k_r$) for reactivation of VX-hAChE conjugate by phenyttetrahydroisoquinoline derivatives was an order of magnitude larger than the corresponding RS 194B constant despite nearly an order of magnitude smaller maximal reactivation rate constant ($k_2$) and largely due to their high apparent affinity for VX-hAChE conjugate ($K_{ox}$=6-47 μm). However, these compounds lack pharmacokinetic, toxicity, and efficacy analyses.

A similar series of a-ketoaldoxime derivatives of poly cyclic peripheral site-directed ligands also exhibited initial promise in reactivation of VX and sarin-conjugated hAChE, whereas tabun-hAChE conjugate reactivation was less efficient (see reference 3). Finally, several amidine-based oximes indicated positive in vitro and in vivo initial properties for reactivation of hAChE inhibited by charged or less volatile nerve agent analogues (see reference 4). Although in vitro reactivation approached 2PAM reactivation levels, in vivo efficacy for treatment of nerve agent-exposed mice is difficult to assess as low toxicity nerve agent surrogates were used as toxicants.

In summary, this study presents uniquely comprehensive characterization of a novel series of N-substituted 2-hydroxyimino acetamido alkylamine reactivators of nerve agent-conjugated hAChE. Through systematic steps of structural modifications, we refined the initial lead RS41A into a superior RS194B reactivator of VX-, sarin-, paraoxon-, cyclosarin-, and tabun-conjugated hAChE both in vitro and in vivo. Cyclosarin has yet to be tested in vivo.

Outstanding intrinsic reactivation potencies of this oxime, resulting in part from its favorable interaction with the peripheral site of AChE, in combination with its low toxicity results provide the lead for a pan-reactive, orally effective antidote for the treatment of OP-exposed mice, either post-exposure or in combination of prophylactic and antidotal oxime treatments of OP-exposed animals.

In one study, VX exposed mice were treated with the exemplary RS194B, or 2PAM, with intramuscular (i.m.) or oral (p.o.) oxime administration. Protective Index is the ratio of $LD_{50}$ values of the organophosphate determined in the presence and in the absence of an oxime. Atropine was always administered i.m. 1 min after VX. These data (summarized in table, below) show true superiority for RS 194B over 2-PAM as an oral antidote or protectant agent. The additional efficacy seen here arises from the superior oral bioavailability of RS194B from the oral route. Oral dosing should also be considered as a maintenance dose to provide longer term antidote action. The volatile organophosphate agents will deposit in lipid reservoirs and slowly leach from those sites. Hence, prolonged protection is warranted after an initial long term exposure.

The following table shows the reactivation data graphically illustrated in FIG. 5, divided by the lethal dose (LD50) of the respective antidote, giving Antidote Indices (reactivation rate/LD50). This shows the superiority of RS 194B over 2-PAM. RS41A and the other potential antidotes:

|  | Protective Index | |
| --- | --- | --- |
| oxime | oxime + atropine 1 min after VX i.m. | oxime: 15 min before VX p.o. atropine: 1 min after VX i.m. |
| RS194B | | |
| 125 mg/kg i.m. | 18 | — |
| 200 mg/kg p.o. | — | 40 |
| 2PAM | | |
| 26 mg/kg i.m. | 9.3 | — |
| 42 mg/kg p.o. | — | 1.1 |

Oxime doses were set as 25% of individual oxime $LD_{50}$ values for i.m. administration and were increased 1.6-fold for oral administration.

The abbreviations used are: OP, organophosphate; AChe, acetylcholinesterase; hAChE, human hAChE; ATCh, acetythiocholine; 2PAM, 2-pyridinealdoxime methiodide; MTNA, monoisonitrosoacetone; DAM, 2,3-butanedione monoxime; PI, protective index; Flu-MP, fluorescent methylphosphonates; VX, O-ethyl S-[2-(diisopropylamino)ethyl] methylphosphonothioate.

Synthetic Procedures

All reactions were performed with commercially available ACS grade reagents and solvents. 1H NMR and $^{13}$C NMR spectra were recorded on a Varian 400 MHz spectrometer. All chemical shifts were reported in ppm relative to solvent resonances, as indicated (DMSO-$d_6$ δ2.49, $^1$H; 539.49, $^{13}$C), (CDCl$_3$ δ7.26, $^1$H; £77.0, $^{13}$C). $^1$H NMR coupling constants (J) are given in Hz. The following compounds were synthesized by known literature methods; 2-(azepan-I-yl)ethanamine, 3-(azepan-I-yl)propan-1-amine and 2-(I,3,3-trimethyl-6-azabicyclo[3.2. I]octan-6-yl) ethanamine (Vooturi et al., 2010), RS41A (Sit et al., 2011) and RS186B (Sato et al., 1988). All other primary amines were obtained commercially.

General method for the preparation of acetamido oximes RS194B, RS194C, RS69N, RS218A, RS69L. and RSI 9 IE The desired amine was added to solution of ethyl glyoxylate oxime 2 in ethanol with stirring. The solution was stirred at 50° C. overnight and cooled to room temperature. The resulting precipitate was filtered, washed with cold ethanol and dried under vacuum.

2-(Hydroxyimino)-N-(2-(azepan-1-yl)ethyl)acetamide (RS194B). Prepared according to the general method. Ethyl glyoxylate oxime 2 (1 g, 8.5 mmol), 2-(azepan-I-1 yl)ethanamine (1.3 g, 9.1 mmol), ethanol (14 mL). White solid, yield (1.1 g, 61%). H NMR (400 MHz, DMSO-$d_6$) δ 11.90 (s, 1H), 7.88 (s, 1H), 7.42 (s, 1H), 3.20 (q, J=6.8 Hz, 2H), 2.61-2.58 (m, 4H), 2.54 (t, J=6.8 Hz, 2H), 1.53 (app s, 8H); $^{13}$C NMR (400 MHz, DMSO-$i/_6$) δ 161.6, 143.7, 56.0, 54.6, 36.7, 27.9, 26.6; LCMS (ESI) (m/z): [M+H]$^+$ calculated for $C_{10}H_{19}N_3O_2$, 214.3; found, 214.5.

2-(Hydroxyimino)-iV-(3-(azepan-1-yl)propyl)acetamide (RS194C). Prepared according to the general method. Ethyl glyoxylate oxime 2 (0.15 g, 1.3 mmol), 3-(azepan-1-yl)propan-1-amine (0.23 g, 1.5 mmol), ethanol (1.3 mL). White solid, yield (0.21 g, 71%). $^1$H NMR (400 MHz, DMSO-$d_6$) δ 11.86 (s, 1H), 8.17 (s, 1H), 7.41 (s, 1H), 3.16 (q, J=8.0 Hz, 2H), 2.52-2.48 (m, 2H), 2.42 (t, J=8.0 Hz, 2H), 1.61-1.48 (m, 12H); $^{13}$C NMR (400 MHz. DMSO-$d_6$) δ 161.6, 143.8, 55.4, 54.9, 37.2, 27.8, 27.0, 26.5; LCMS (ESI) (m/z): [M+H]$^+$ calculated for $O_{11}H_{21}N_3O_2$, 228.3; found, 228.5.

2-(Hydroxyimino)-N-(2-(piperidin-1-yl)ethylacetamide (RS69N). Prepared according to the general method. Ethyl glyoxylate oxime 2 (0.15 g, 1.3 mmol), 2-(piperidin-1-yl)ethanamine (0.19 g, 1.5 mmol), ethanol (1.3 mL). White solid, yield (0.17 g, 66%). H NMR (400 MHz, DMSO-$d_6$) δ 11.91 (s, 1H), 7.91 (s, 1H), 7.42 (s, 1H), 3.24 (q, J=8, 2H), 2.37-2.29 (m, 6H), 1.50-1.41 (m, 4H), 1.36 (app d, J=4, 2H); $^{13}$C NMR (400 MHz, DMSO-$d_6$) δ 161.6, 143.7, 57.3, 54.0, 35.9, 25.6, 24.0; LCMS (ESI) (m/z): [M+Naf calculated for $C_9H_{17}N_3O_2$, 216.2; found, 216.3.

2-(hydroxyimino)-N-(2-(1,3,3-trimethyl-6-azabicyclo [3.2.1]octan-6-yl)ethyl) acetamide (RS218A). Prepared according to the general method. Ethyl glyoxylate oxime 2 (0.20 g, 1.7 mmol), 2-(I,3,3-trimethyl-6-azabicyclo[3.2.1]octan-6-yl)ethanamine (0.40 g, 2 mmol), ethanol (4 mL). White solid, yield (0.27 g, 59%). $^1$H NMR (400 MHz, DMSO-$d_6$) δ 11.86 (s, 1H), 7.80 (s, 1H), 7.39 (s, 1H), 3.14 (app s, 2H), 3.04 (s, 1H), 2.86 (d, J=8, 1H), 2.66 (app s, 1H), 2.57-2.51 (m, 1H), 2.08 (d, J=8, 1H), 1.49 (app s, 2H), 1.32 (d, J=12, 2H), 1.18 (s, 3H), 1.15-1.03 (m, 2H), 0.99 (s, 3H), 0.84 (s, 3H); $^{13}$C NMR (400 MHz, DMSO-$d_6$) δ 161.6, 143.6, 64.7, 61.8, 56.5, 51.5, 44.9, 41.2, 40.9, 40.1, 38.3, 36.5, 31.8, 29.8, 25.7; LCMS (ESI) (m/z): [M+Hf calculated for $C_{14}H_{25}N_3O_2$, 268.4; found, 268.5.

2-(hydroxyimino)-N-(3-(pyrrolidin-1-yl)propyl)acetamide (RS69L). Prepared according to the general method. Ethyl glyoxylate oxime 2 (0.17 g, 1.4 mmol), 3-(pyrrolidin-1-yl)propan-1-amine (0.22 g, 1.7 mmol), ethanol (2.5 mL). White solid, yield (0.15 g, 54%). $^1$H NMR (400 MHz, DMSO-$d_6$) δ 11.88 (s, 1H), 8.20 (s, 1H), 7.41 (s, 1H), 3.17 (q, J=6.8 Hz, 2H), 2.41-2.35 (m, 6H), 1.68-0.61 (m, 4H), 1.58 (t, J=6.8 Hz, 2H); $^{13}$C NMR (400 MHz, DMSO-$d_6$) δ 161.6, 143.8, 54.9, 53.6, 37.3, 28.1, 23.1; LCMS (ESI) (m/z): [M+H]$^+$ calculated for $C_9H_{17}N_3O_2$, 200.2; found, 200.4.

2-(hydroxyimino)-iV-(3-(piperidin-1-yl)propyl)acetamide (RS191E). Prepared according to the general method. Ethyl glyoxylate oxime 2 (0.15 g, 1.3 mmol), 3-(piperidin-1-yl)propan-1-am-ine (0.22 g, 1.5 mmol), ethanol (5 mL). White solid, yield (0.15 g, 54%). $^1$H NMR (400 MHz, DMSO-$d_6$) δ 11.78 (s, 1H), 8.22 (s, 1H), 7.40 (s, 1H), 3.16 (q, J=8 Hz, 2H), 2.27-2.23 (m, 6H), 1.58 (pent, J=8 Hz, 2H), 1.48 (pent, J=8 Hz, 4H), 1.36 (app d, J=4, 2H); $^{13}$C NMR (400 MHz, DMSO-$d_6$) δ161.6, 143.7, 56.6, 54.1, 37.5, 26.0, 25.6, 24.2; LCMS (ESI) (m/z): [M+H]r calculated for $C_{10}H_{19}N_3O_2$, 214.3; found, 214.5.

REFERENCES (1) Vooturi, S. K.: Firestine, S. M J. Comb. Chem. 2010, 12 (1), 151-160; (2) Sit, R. K.; Radic, Z.; Gerardi, V.; Zhang' L.; Garcia, E.; Katalinic, M; Kovarik, Z.; Fokin, V. V.; Sharpless, K. B.; and Taylor, P. J. Biol. Chem. 2011, 286, 19422-19430; (3) Sato, N.; Saito, N. J. Heterocycl. Chem. 1988, 25 (6), 1737-1740.

Further Synthetic Schemes

Figure 35:
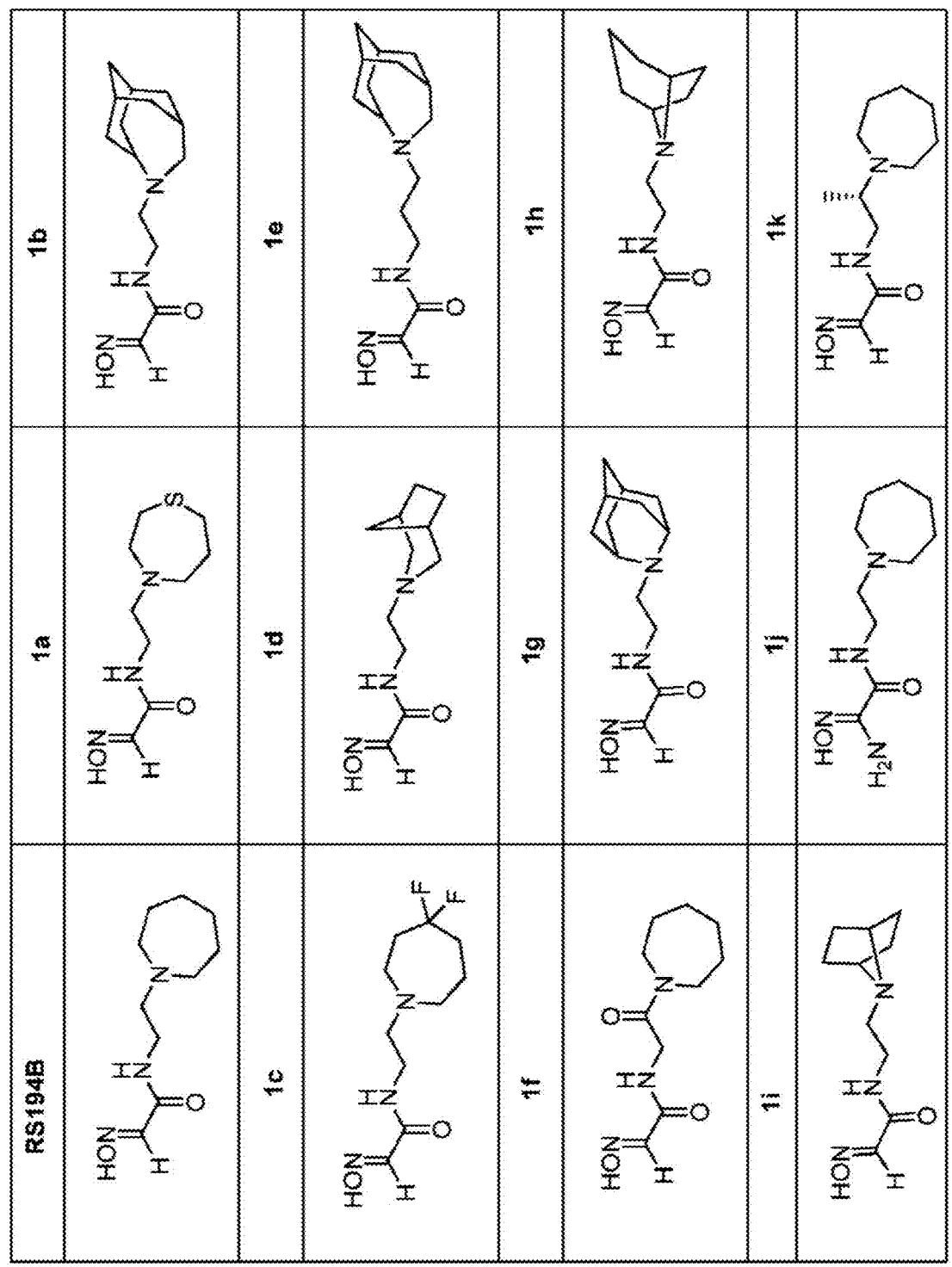
FIG. 35 graphically illustrates alternative exemplary structures of the invention, as discussed in detail in Example 1, below.

Our previous studies have indicated that the tertiary amine containing region of the oxime molecule is a critical modulator of activity. Herein we explored the effect of the tertiary amine size on the rate of reactivation towards organophosphate inhibited acetylcholinesterase. Uncharged reactivators demonstrate the ability to cross the blood brain barrier and are a logical step towards improving existing treatments for organophosphate poisoning. Building on our lead compound, RS1 94B, we demonstrate here 10 additional derivatives (Ia-k), as illustrated in FIG. 35.

By use of previous protocol, N-substituted 2-hydroxyiminoacetamides Ia-e were synthesized, as shown in scheme 1. The synthesis begins by reacting the pthalimide protected amino alkyl bromide with the desired secondary amine (2a-d) to yield the protected intermediates. In the next step, deprotection of the intermediate using hydrazine reveals the desired amine (3a-e) in moderate yield, and followed by subsequent amidation with ethyl glyoxylate oxime 4 delivers oxime derivatives Ia-e.

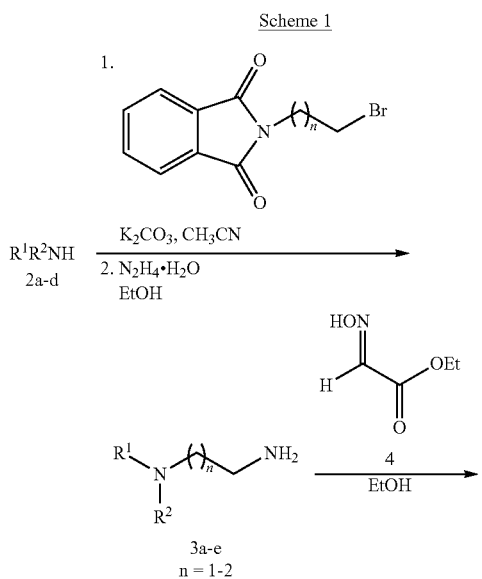

Scheme 1

Furthermore, to obtain oxime derivatives If-i the corresponding primary amines 3f-i were first synthesized following a different route, shown in scheme 2. In the first step the acid chloride reacts with glycine under Schotten-Baumann conditions to form N-protected glycine 5. Next, carboxamidation of 5 with desired secondary amines (2e-h) was done to obtain carboxamide 6. Removal of Cbz group of 6, and followed by reduction with LiAlH$_4$ in THF gave primary amines 3f-i. Amidation of ethyl glyoxylate oxime 4 with corresponding primary amines provided acetamide oxime derivatives If-i.

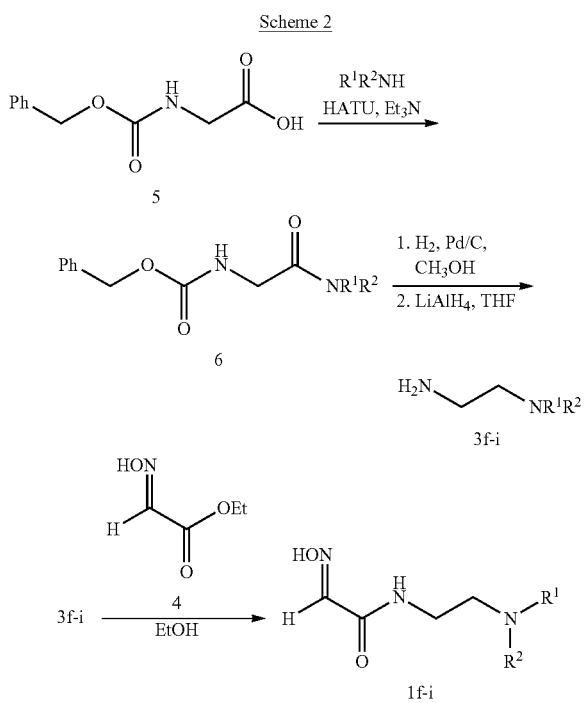

Scheme 2

The synthesis of secondary amine 4-azatricyclo [4.3.1.I.$^{3'8}$]undecan 2b was straightforward and involved an initial condensation of 2-adamantanone 7 with hydroxylamine to afford adamantan-2-oxime, followed by Beckmann rearrangement to form the 4-azatricyclo[4.3.1.I.$^{3'8}$]-undecan-5-one (8) (scheme 3). Reduction of 4-azatricyclo amide derivative 8 furnished 4-azatricyclo[4.3.1.1.$^{'8}$]undecane 2b.

Similarly, the secondary amine 1,4-thiazepane 2a was also prepared following the same synthetic route. Further, the bicyclic amine 2d was made from starting material norcamphor 9 in two steps. 3-Azabicyclo[3.2. I]octan-2-one (10) was obtained by carrying out curtius rearrangement on 9. Finally, reduction with L1AlH$_4$ in Et20 delivered 3-azabicyclo[3.2.1]octane in moderate yield 2d.

Scheme 3

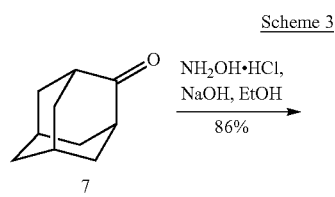

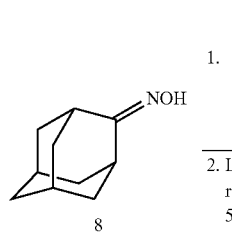

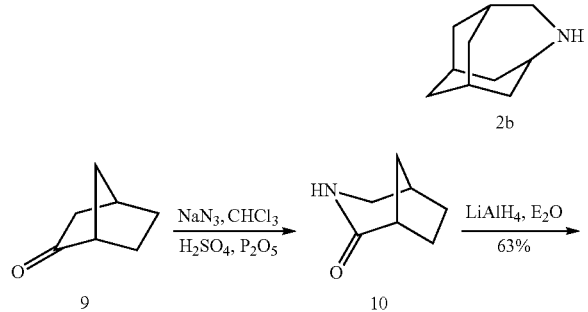

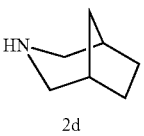

It was decided to incorporate fluorine in the azepane ring at position 4 in RS194B, scheme 4, to achieve a modest pKa reduction of the cyclic amine and thus N-(2-(4,4-difluoro-azepan-1-yl)ethyl)-2-(hydroxyimino)acetamide c was synthesized. Difluoride 2c was obtained from 11 following treatment with aminosulfurane and subsequent Boc deprotection. To synthesize oxime derivative Ih, bicyclic amine 8-azabicyclo[3.2.1]octane hydrochloride 2g was obtained via chloroethyl chloroformate mediated dealkylation of the tertiary amine 13. Further, trans-4-aminocyclohexanol 15 was protected using Boc-anhydride and then mesylation was done to obtain Boc-protected cyclohexyl methanesulfonate 16. In the next step, Boc group was removed under acidic condition and the TFA salt of cyclohexyl methanesulfonate was cyclized under basic condition to deliver 7-azabicyclo[2.2.1] heptanes 2h in moderate yield.

Scheme 4

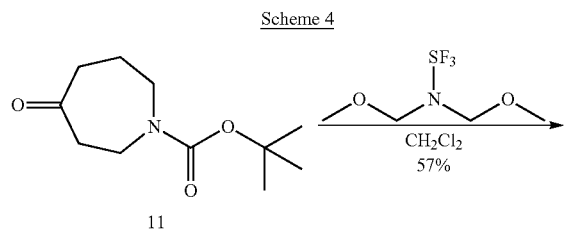

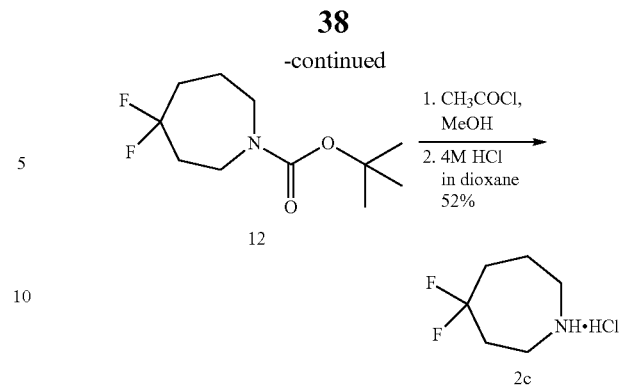

After successful synthesis of oximes 1a-i, modification of vicinity of the nucleophilic oxime was made and the oxime derivative 1j was prepared. Glycine ester hydrochloride 18 was converted into 2-chloro-2 (hydroxyimino)acetate, followed by treatment with NH₃ (g) afforded 2-amino-2-(hydroxyimino)acetate 19. Amidation of 19 with 2-(azepan-1-yl)ethan-1-amine delivered acetamide oxime 1j.

Scheme 5

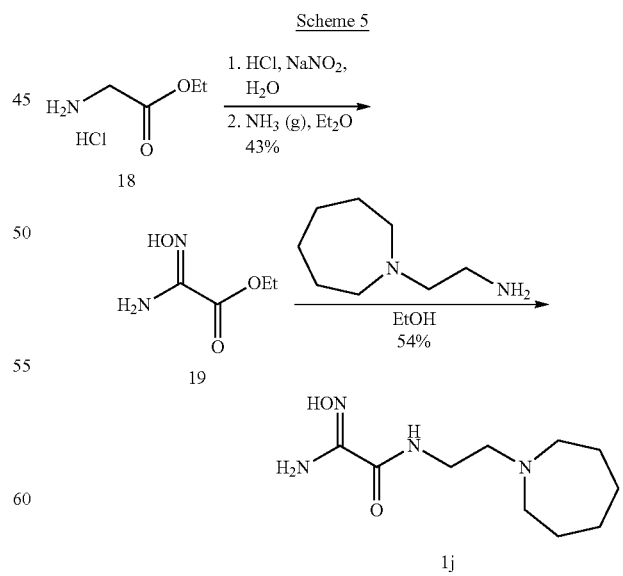

To investigate the effect of introducing methyl group in the linker, the oxime derivative Ik was prepared. The primary amine 3k was first synthesized in two steps. The appropriate tertiary amine carboxamide 21 was prepared from the readily available L-alaninamide by reaction with 1,6-dibromohexane under basic conditions to construct the azepane ring. Reduction of carboxamide 21 with LiAlH$_4$ in THF afforded 3k and subsequent amidation with ethyl glyoxylate oxime 4 delivered acetamide oxime Ik.

Scheme 6

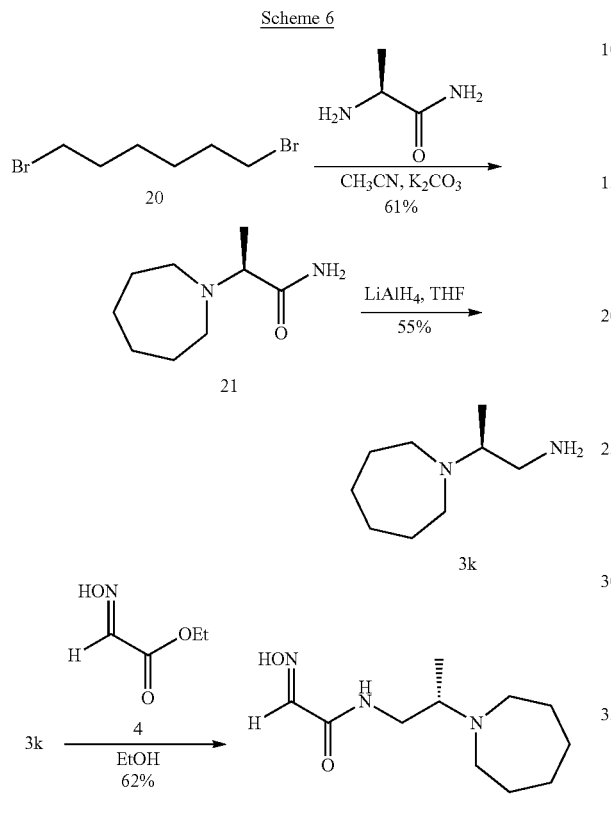

General Synthetic Protocols

All reactions were performed with commercially available ACS grade reagents and solvents. Anhydrous N,N-dimethylformamide (DMF), acetonitrile and chloroform, dichloromethane were used as received without further purification. $^1$H NMR and $^{13}$C NMR spectra were recorded on a Varian 400 MHz spectrometer. All chemical shifts were reported in ppm relative to solvent resonances, as indicated (DMSO-d$_6$ δ2.50, $^1$H; δ39.50, $^{13}$C), (CDCl$_3$ δ7.26, $^1$H; δ77.16, $^{13}$C). $^1$H NMR coupling constants (J) are given in Hz.

A. General method for the preparation of primary amines (3a-e). A 15 mmol solution of secondary amine (2a-e) in 80 mL of acetonitrile was treated with 18.75 mmol of N-bromopthalimide and K$_2$CO$_3$ (45.0 mmol). The resulting mixture was refluxed overnight. After the reaction was completed, 90 mL of saturated NaHCO$_3$ was added followed by extraction with ethyl acetate. The combined organic layers were acidified with 2 N HCl and washed with water. The pH of the aqueous layer was adjusted to pH 12 using 4 N NaOH and then extracted with methylene chloride. The organic solution was dried over Na$_2$SO$_4$ and evaporated to yield the product, which is used in the next reaction without further purification.

The N-alkylated pthalimide obtained above was dissolved in 80 mL of ethanol and hydrazine hydrate (3 equiv) was added. The reaction was refluxed for 3 h and cooled to room temperature, and the resulting precipitate was removed by filtration. The filtrate was concentrated and the residue was diluted with 30 mL of EtOAc. The resulting precipitate was removed by filtration, the filtrate was concentrated to dryness and kugelrohr distillation was done to obtain pure amine.

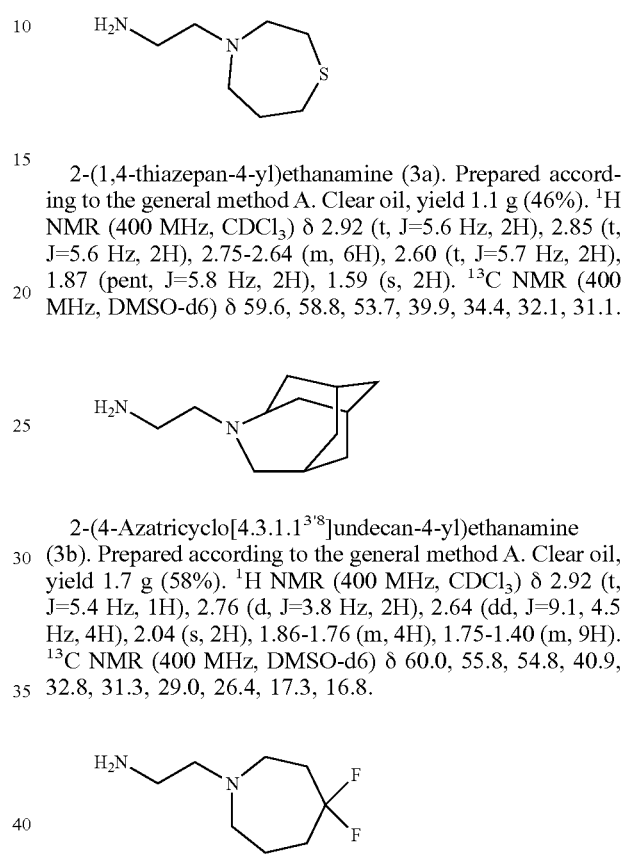

2-(1,4-thiazepan-4-yl)ethanamine (3a). Prepared according to the general method A. Clear oil, yield 1.1 g (46%). $^1$H NMR (400 MHz, CDCl$_3$) δ 2.92 (t, J=5.6 Hz, 2H), 2.85 (t, J=5.6 Hz, 2H), 2.75-2.64 (m, 6H), 2.60 (t, J=5.7 Hz, 2H), 1.87 (pent, J=5.8 Hz, 2H), 1.59 (s, 2H). $^{13}$C NMR (400 MHz, DMSO-d6) δ 59.6, 58.8, 53.7, 39.9, 34.4, 32.1, 31.1.

2-(4-Azatricyclo[4.3.1.1$^{3,8}$]undecan-4-yl)ethanamine (3b). Prepared according to the general method A. Clear oil, yield 1.7 g (58%). $^1$H NMR (400 MHz, CDCl$_3$) δ 2.92 (t, J=5.4 Hz, 1H), 2.76 (d, J=3.8 Hz, 2H), 2.64 (dd, J=9.1, 4.5 Hz, 4H), 2.04 (s, 2H), 1.86-1.76 (m, 4H), 1.75-1.40 (m, 9H). $^{13}$C NMR (400 MHz, DMSO-d6) δ 60.0, 55.8, 54.8, 40.9, 32.8, 31.3, 29.0, 26.4, 17.3, 16.8.

2-(4,4-Difluoroazepan-1-yl)ethanamine (3c). Prepared according to the general method A. Light yellow oil, yield 1.3 g (48%).

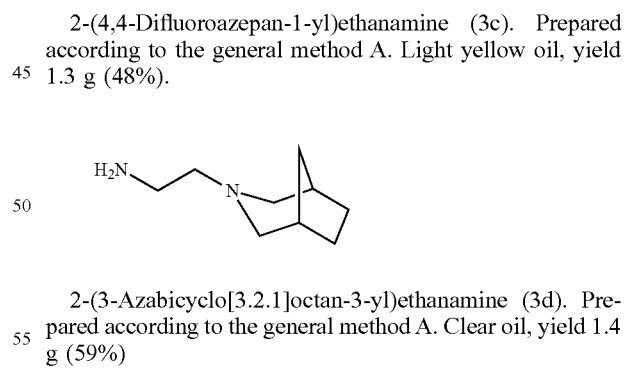

2-(3-Azabicyclo[3.2.1]octan-3-yl)ethanamine (3d). Prepared according to the general method A. Clear oil, yield 1.4 g (59%)

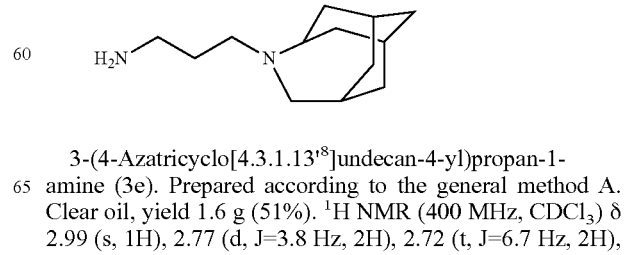

3-(4-Azatricyclo[4.3.1.1$^{3,8}$]undecan-4-yl)propan-1-amine (3e). Prepared according to the general method A. Clear oil, yield 1.6 g (51%). $^1$H NMR (400 MHz, CDCl$_3$) δ 2.99 (s, 1H), 2.77 (d, J=3.8 Hz, 2H), 2.72 (t, J=6.7 Hz, 2H), 2.61 (t, J=7.1 Hz, 2H), 2.05 (s 1H), 1.90-1.75 (m, 6H), 1.69-1.63 (m, 3H), 1.62-1.52 (m, 5H), 1.49-1.45 (m, 2H).

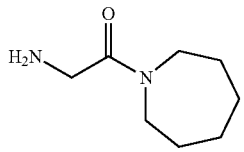 [SMILES: NCC(=O)N1CCCCCC1]

2-Amino-1-(azepan-1-yl)ethanone (3f). To a stirred solution
of ((benzyloxy)carbonyl)glycine (1 g, 4.78 mmol) in 35 mL of dichloromethane at rt, HATU (2 g, 5.3 mmol) and DIPEA (1.8 g, 14.3 mmol) were added. The reaction mixture was stirred for 10 min, and then azepane (1 g, 10.5 mmol) was added, and stirred for another 3 h. The resulting reaction mixture was filtered and the filtrate was concentrated. The obtained residue was purified by flash column chromatography (EtOAc/hexane, 8:2) to obtain 1.1 g (79%) of benzyl (2-(azepan-1-yl)-2-oxoethyl)carbamate as a clear oil.

Benzyl(2-(azepan-1-yl)-2-oxoethyl)carbamate (1 g, 3.4 mmol) was dissolved in 40 mL of MeOH, degassed and placed under argon. 10% Pd/C (0.25 g) was added, and the contents were thoroughly degassed, placed under hydrogen via balloon and stirred overnight. The resulting reaction mixture was filtered through Celite, and the Celite pad was subsequently washed with DCM and MeOH. The resulting filtrate was concentrated in vacuo and kugelrohr distillation was done to afford 0.50 g (94%) of the title compound as clear oil. $^1$H NMR (400 MHz, CDCl$_3$) δ 3.50 (t, J=6.0 Hz 2H), 3.41 (s, 2H), 3.30 (t, J=6.0 Hz, 2H), 1.78 (s, 2H), 1.72-1.63 (m, 4H), 1.51 (dd, J=5.9, 3.0 Hz, 4H). $^{13}$C NMR (400 MHz, DMSO-d6) δ 172.2, 46.4, 46.2, 43.1, 28.9, 27.6, 27.2, 26.9.

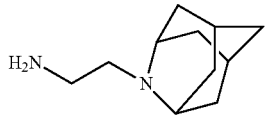

2-(Azaadamantan-2-yl)ethanamine (3g). To a stirred solution
of ((benzyloxy)carbonyl)glycine (0.70, 3.3 mmol) in 25 mL of dichloromethane at rt, HATU (1.40 g, 3.6 mmol) and DIPEA (0.90 g, 6.9 mmol) were added. The reaction mixture was stirred for 10 min, and then 2-azaadamantane (0.54 g, 4 mmol) was added, and stirred for another 3 h. The resulting reaction mixture was filtered and the filtrate was concentrated. The obtained residue was purified by flash column chromatography (EtOAc/hexane, 7:3) to obtain 0.90 g (83%) of benzyl(2-(2-azaadamantane-2-yl)-2-oxoethyl)carbamate as a clear oil.

Benzyl(2-(2-azaadamantane-2-yl)-2-oxoethyl)carbamate (0.85 g, 2.6 mmol)
was dissolved in 25 mL of MeOH, degassed and placed under argon. 10% Pd/C (0.25 g) was added, and the contents were thoroughly degassed, placed under hydrogen via balloon and stirred overnight. The resulting reaction mixture was filtered through Celite, and the Celite pad was subsequently washed with DCM and MeOH. The resulting filtrate was concentrated in vacuo to deliver 1-(2-azaadamantane-2-yl)-2-aminoethan-1-one (0.43 g, 85%).

To a stirred suspension of LAH (0.24 g. 9.7 mmol) in THF (20 mL) at 0° C. was added dropwise to a solution of 1-(2-azaadamantane-2-yl)-2-aminoethan-1-one (0.40 g, 2.1 mmol) in 20 mL of THF. The reaction mixture was stirred overnight at rt. The resulting reaction mixture was quenched with careful addition of H$_2$O (0.30 mL), followed by 15% aqueous NaOH (0.60 mL), and H$_2$O (0.90 mL). This crude mixture was filtered through a small pad of Celite, and the filter cake was washed with ether (10 mL). The filtrate was concentrated and kugelrohr distillation was done to afford 0.29 g (76%) of the title compound as a clear oil. $^1$H NMR (400 MHz, cdcl$_3$) δ 2.75 (s, 2H), 2.71-2.63 (m, 4H), 2.03-1.95 (m. 6H), 1.78 (s, 2H), 1.72 (s, 2H), 1.53 (s, 2H), 1.50 (s, 2H). $^{13}$C NMR (400 MHz. DMSO-d6) δ 55.9, 51.8, 40.2, 37.3, 33.5, 27.5.

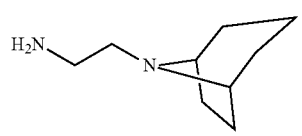 [SMILES: NCCN1C2CCCC1CC2]

2-(8-Azabicyclo[3.2.1]octan-8-yl)ethanamine (3h). To a stirred solution of ((benzyloxy)carbonyl)glycine (0.80, 3.8 mmol) in 25 mL of dichloromethane at rt, HATU (1.60 g, 4.2 mmol) and DIPEA (1.5 g, 11.6 mmol) were added. The reaction mixture was stirred for 10 min, and then 8-azabicyclo[3.2.1]octane hydrochloride (1.1 g, 7.4 mmol) was added, and stirred for another 3 h. The resulting reaction mixture was filtered and the filtrate was concentrated. The obtained residue was purified by flash column chromatography (EtOAc/hexane, 8:2) to obtain 1.1 g (95%) of benzyl (2-(8-azabicyclo[3.2.1]heptan-7-yl)-2-oxoethyl)carbamate as a clear oil.

Benzyl(2-(8-azabicyclo[3.2.1]heptan-7-yl)-2-oxoethyl)carbamate (1.1 g, 3.6 mmol) was dissolved in 40 mL of MeOH, degassed and placed under argon. 10% Pd/C (0.28 g) was added, and the contents were thoroughly degassed, placed under hydrogen via balloon and stirred overnight. The resulting reaction mixture was filtered through Celite, and the Celite pad was subsequently washed with DCM and MeOH. The resulting filtrate was concentrated in vacuo to deliver 2-amino-1-(8-azabicyclo[3.2.1]octan-8-yl)ethan-1-one (0.59 g, 97%).

To a stirred suspension of LAH (0.40 g, 10.5 mmol) in THF (20 mL) at 0° C. was added dropwise to a solution of 2-amino-1-(8-azabicyclo[3.2.1]octan-8-yl)ethan-1-one (0.59 g, 3.5 mmol) in 20 mL of THF. The reaction mixture was stirred overnight at rt. The resulting reaction mixture was quenched with careful addition of $^1$H 0 (0.40 mL), followed by 15% aqueous NaOH (0.80 mL), and H$_2$O (1.3 mL). This crude mixture was filtered through a small pad of Celite, and the filter cake was washed with ether (10 mL).

The filtrate was concentrated and kugelrohr distillation was done to afford 0.35 g (65%) of the title compound as a clear oil. $^1$H NMR (400 MHz, cdcl$_3$) δ 3.09 (s, 2H), 2.69 (t, J=6.3 Hz, 2H), 2.34 (t, J=6.3 Hz, 2H), 1.91-1.82 (m. 2H), 1.78 (s. 2H), 1.72-1.57 (m, 2H), 1.54-1.47 (m, 2H), 1.45-1.35 (m, 2H), 1.29 (d, J=12.9 Hz, 2H). $^{13}$C NMR (400 MHz, DMSO-d6) δ 60.0, 55.8, 54.8, 40.9, 32.8, 31.3, 29.0, 26.4, 17.3, 16.8.

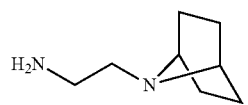

2-(7-Azabicyclo[2.2.1]heptan-7-yl)ethanamine (3i). To a stirred solution of ((benzyloxy)carbonyl)glycine (0.80, 3.8 mmol) in 25 mL of dichloromethane at rt, HATU (1.60 g, 4.2 mmol) and DIPEA (1.5 g, 11.6 mmol) were added. The reaction mixture was stirred for 10 min, and then 7-azabicyclo[2.2.1]heptane hydrochloride (0.76 g, 5.7 mmol) was added, and stirred for another 3 h. The resulting reaction mixture was filtered and the filtrate was concentrated. The obtained residue was purified by flash column chromatography (EtOAc/hexane, 8:2) to obtain 1 g (91%) of benzyl (2-(7-azabicyclo[2.2.1]heptan-7-yl)-2-oxoethyl)carbamate as a clear oil.

Benzyl(2-(7-azabicyclo[2.2.1]heptan-7-yl)-2-oxoethyl) carbamate (1 g, 3.5 mmol) was dissolved in 40 mL of MeOH, degassed and placed under argon. 10% Pd/C (0.26 g) was added, and the contents were thoroughly degassed, placed under hydrogen via balloon and stirred overnight. The resulting reaction mixture was filtered through Celite, and the Celite pad was subsequently washed with DCM and MeOH. The resulting
filtrate was concentrated in vacuo to deliver 2-amino-1-(7-azabicyclo[2.2.1]heptan-7-yl)ethan-1-one (0.50 g, 93%).

To a stirred suspension of LAH (0.37 g, 9.7 mmol) in THF (20 mL) at 0° C. was added dropwise to a solution of 2-amino-1-(7-azabicyclo[2.2.1]heptan-7-yl)ethan-1-one (0.50 g, 3.2 mmol) in 20 mL of THF. The reaction mixture was stirred overnight at rt. The resulting reaction mixture was quenched with careful addition of $^1$H 0 (0.40 mL), followed by 15% aqueous NaOH (0.80 mL), and H$_2$O (1.3 mL). This crude mixture was filtered through a small pad of Celite, and the filter cake was washed with ether (10 mL). The filtrate was concentrated and kugelrohr distillation was done to afford 0.31 g (69%) of the title compound as clear oil. $^{13}$C NMR (400 MHz, DMSO-d6) δ 61.6, 56.4, 56.1, 40.9, 37.6, 36.1, 35.7, 32.2, 31.7, 26.7.

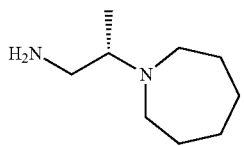

(S)-2-(Azepan-1-yl)propan-1-amine (3k). 1,5-Dibromopentane (3.0 g, 12.3 mmol mmol) was added to a suspension of L-alaninamide (1.5 g, 12 mmol), potassium carbonate (5 g, 36 mmol), and potassium iodide (6 mg) in CH$_3$CN (36 mL). The mixture was refluxed overnight and then cooled to rt. The mixture was treated with 75 mL of 1N HCl and extracted with dichloromethane. The organic layer was discarded. The aqueous layer was basified with 4N NaOH and extracted with dichloromethane (3×30 mL). The solvent was evaporated to dryness to obtain 1.50 g (73%) of (S)-2-(azepan-1-yl)propanamide.

To a stirred suspension of LAH (1.5 g, 41.1 mmol) in THF (80 mL) at 0° C. was added dropwise a solution of (S)-2-(azepan-1-yl)propanamide (1.4 g, 8.2 mmol) in 40 mL of THF. The reaction mixture was stirred overnight at 50° C. and cooled to rt. The resulting reaction mixture was quenched with careful addition of H$_2$O (1.5 mL), followed by 15% aqueous NaOH (3 mL), and H$_2$O (5 mL). A thick gel-like precipitate was formed. The reaction mixture was filtered through a small pad of Celite, and the filter cake was washed with ether (50 mL). The filtrate was concentrated and kugelrohr distillation was done to afford 0.90 g (66%) of the title compound as a clear oil.

$^1$H NMR (400 MHz, cdcl$_3$) δ 2.68-2.56 (m, 3H), 2.56-2.47 (m, 1H), 2.44-2.35 (m, 3H), 1.66-1.43 (m, 10H), 0.81 (d, J=6.3 Hz, 3H). $^{13}$C NMR (400 MHz, DMSO-d6) δ 62.8, 50.7, 45.5, 29.9, 26.9, 11.4.

B. General method for the preparation of acetamide oximes Ia-k. The desired primary amine (3a-j) was added to a solution of ethyl glyoxylate oxime 4 in ethanol with stirring. The solution was stirred overnight at room temperature. The resulting precipitate was filtered, washed with cold ethanol and dried under vacuum.

N-(2-(4-Azatricyclo[4.3.1.1$^{3,8}$]undecan-4-yl)ethyl)-2-(hydroxyimino)acetamide (RS2-138B) Prepared according to the general method B. Ethyl glyoxylate oxime 3 (0.75 g, 6.41 mmol), 2-(4-azatricyclo[4.3.1.13$^{'8}$]undecan-4-yl) ethanamine (1.4 g, 7.0 mmol), ethanol (10 mL). White solid, yield (1 g, 60%). $^1$H NMR (400 MHz, dmso) δ 11.91 (s, 1H), 7.87 (s, 1H), 7.42 (s, 1H), 3.19 (dd, J=12.8, 6.4 Hz, 2H), 2.95 (d, J=5.1 Hz, 1H), 2.77 (d, J=3.8 Hz, 2H), 2.66 (t, J=6.8 Hz, 2H), 2.04 (s, 1H), 1.82 (d, J=10.7 Hz, 4H), 1.69 (d, J=13.6 Hz, 2H), 1.59-1.40 (m, 6H). $^{13}$C NMR (400 MHz, DMSO-d6) δ 161.6, 143.7, 60.5, 56.8, 55.9, 37.3, 37.0, 35.7, 35.4.

N-(2-(2-Azaadamantan-2-yl)ethyl)-2-(hydroxyimino)acetamide (RS3-36D) Prepared according to the general method B. Ethyl glyoxylate oxime 3 (0.15 g, 1.3 mmol), 2-(2-azaadamantan-2-yl)ethanamine (0.25 g, 1.4 mmol), ethanol (4 mL). White solid, yield (0.26 g, 79%). $^1$H NMR (400 MHz, dmso) δ 11.92 (s, 1H), 7.86 (s, 1H), 7.42 (s, 1H), 3.15 (dd, J=12.8, 6.5 Hz, 2H), 2.75 (s, 2H), 2.68 (t, J=6.9 Hz, 2H), 1.93 (d, J=6.9 Hz, 6H), 1.75 (s, 2H), 1.50 (d, J=10.8 Hz, 4H). $^{13}$C NMR (400 MHz, DMSO-d6) δ 161.6, 143.7, 51.7, 50.9, 37.3, 36.6, 32.9, 26.8.

(5)-N-(2-(Azepan-1-yl)propyl)-2-(hydroxyimino)acetamide (RS2-245C) Prepared according to the general method B. Ethyl glyoxylate oxime 3 (0.50 g, 4.27 mmol), (5)-2-(azepan-1-yl)propan-1-amine (0.77 g, 4.91 mmol), ethanol (7 mL). White solid, yield (0.60 g, 62%). $^1$H NMR (400 MHz, dmso) δ 11.95 (s, 1H), 7.77 (s, 1H), 7.42 (s, 1H), 3.20-3.00 (m, 2H), 2.83 (sext. J=7.1 Hz. 1H), 2.67-2.61 (m, 2H), 2.52 (s, 2H), 1.52 (s, 8H), 0.88 (s, 3H). $^{13}$C NMR (400 MHz, DMSO-d6) δ 161.5, 143.7, 58.7, 50.2, 41.5, 39.5, 29.2, 26.4, 12.3.

N-(2-(Azepan-1-yl)-2-oxoethyl)-2-(hydroxyimino)acetamide (RS2-90C)
Prepared according to the general method B. Ethyl glyoxylate oxime 3 (0.30 g, 2.56 mmol), 2-amino-1-(azepan-1-yl)ethanone (0.46 g, 2.94 mmol), ethanol (6 mL). White solid, yield (0.34 g, 58%). $^1$H NMR (400 MHz, DMSO-d6) $^1$H NMR (400 MHz, dmso) δ
12.04 (s, 1H), 8.02 (s, 1H), 7.50 (s, 1H), 4.02 (d, J=5.2 Hz, 1H), 3.41 (dd, J=11.7, 5.7 Hz, 2H), 1.74-1.63 (m, 1H), 1.63-1.54 (m, 1H), 1.54-1.35 (m, 2H). $^{13}$C NMR (400 MHz, DMSO-d6) δ 167.2, 161.7, 143.3, 46.1, 45.4, 28.2, 27.1, 26.7, 26.2.

N-(2-(8-Azabicyclo[3.2.1]octan-8-yl)ethyl)-2-(hydroxyimino)acetamide (RS2-237D) Prepared according to the general method B. Ethyl glyoxylate oxime 3 (0.17 g, 1.5 mmol), 2-(8-azabicyclo[3.2.1]octan-8-yl)ethanamine (0.25 g, 1.6 mmol), ethanol (5 mL). White solid, yield (0.24 g, 71%). $^1$H NMR (400 MHz, DMSO) δ 11.92 (s, 1H), 7.92 (s, 1H), 7.42 (s, 1H), 3.19 (q, J=6.5 Hz, 2H), 3.11 (s. 2H), 2.36 (t, J=6.9 Hz, 2H), 1.93-1.73 (m, 2H), 1.65-1.50 (m, 3H), 1.49 (d. J=7.5 Hz. 2H), 1.39-1.19 (m, 3H). $^{13}$C NMR (400 MHz, DMSO-d6) δ 161.6, 143.7, 59.2, 51.2, 37.8, 30.6, 26.0, 16.3.

N-(2-(7-Azabicyclo[2.2.1]heptan-7-yl)ethyl)-2-(hydroxyimino)acetamide (RS2-234D) Prepared according to the general method B. Ethyl glyoxylate oxime 3 (0.23 g, 1.94 mmol), 2-(7-azabicyclo[2.2.1]heptan-7-yl)ethanamine (0.30 g, 2.14 mmol), ethanol (5 mL). White solid, yield (0.28 g, 68%).

N-(2-(3-Azabicyclo[3.2.1]octan-3-yl)ethyl)-2-(hydroxyimino)acetamide (RS3-43D) Prepared according to the general method B. Ethyl glyoxylate oxime 3 (0.35 g, 3.0 mmol), 2-(3-azabicyclo[3.2.1]octan-3-yl)ethanamine (0.53 g, 3.44 mmol), ethanol (7 mL). White solid, yield (0.41 g, 60%). %). $^1$H NMR (400 MHz, DMSO) δ 11.92 (s, 1H), 7.82 (s, 1H), 7.41 (s, 1H), 3.21 (d, J=5.6 Hz, 2H), 2.61 (d, J=8.5 Hz, 2H), 2.36 (d, J=6.1 Hz. 2H), 2.07 (s, 2H), 2.00 (d, J=9.9 Hz, 2H), 1.65-1.35 (m, 5H), 1.29 (d, J=10.6 Hz, 1H). $^{13}$C NMR (400 MHz, DMSO-d6) δ161.6, 143.7, 60.8, 59.5, 56.1, 37.2, 35.9, 34.6, 28.3.

7V-(3-(4-Azatricyclo[4.3.1.1$^{3'8}$]undecan-4-yl)propyl)-2-(hydroxyimino)acetamide (RS2-150C) Prepared according to the general method B. Ethyl glyoxylate oxime 3 (0.50 g, 4.27 mmol), 3-(4-azatricyclo[4.3.1.1$^{3'8}$]undecan-4-yl)propan-1-amine (1.0 g, 4.91 mmol), ethanol (9 mL). White solid, yield (0.70 g, 59%). $^1$H NMR (400 MHz, dmso)^ 1.84 (s, 1H), 8.18 (s, 1H), 7.41 (s, 1H), 3.17 (q, J=6.6 Hz, 2H), 2.95 (s, 1H), 2.72 (d, J=3.8 Hz, 2H), 2.55 (t, J=6.8 Hz, 2H), 2.04 (s, 1H), 1.81 (s, 4H), 1.73-1.62 (m, 2H), 1.60-1.42 (m, 8H). $^{13}$C NMR (400 MHz, DMSO-d6) δ 161.6, 143.9, 60.8, 55.8, 55.6, 37.2, 37.1, 35.5, 30.9, 27.8, 26.1.

N-(2-(Azepan-1-yl)ethyl)-2-(hydroxyamino)-2-iminoacetamide (RS292A) Prepared according to the general method B. Ethyl glyoxylate oxime 3 (0.30 g, 2.56 mmol), 2-(azepan-1-yl)ethanamine (0.42 g, 2.94 mmol), ethanol (6 mL). White solid, yield (0.32 g, 54%). $^1$H NMR (400 MHz, dmso) δ 9.85 (s, 1H), 7.65 (s, 1H), 5.62 (s, 2H), 3.19 (q, J=6.3 Hz, 2H), 2.61-2.57 (m, 2H), 2.53 (t, J=6.6 Hz, 2H), 1.53 (s, 8H). $^{13}$C NMR (400 MHz, DMSO-d6) δ 161.6, 143.7, 56.0, 54.6, 36.7, 28.0, 26.6.

N-(2-(4,4-Difluoroazepan-1-yl)ethyl)-2-(hydroxyimino)acetamide (RS2-140B) Prepared according to the general method B. Ethyl glyoxylate oxime 3 (0.30 g, 2.56 mmol), 2-(4,4-difluoroazepan-1-yl)ethanamine (0.52 g, 2.94 mmol), ethanol (6 mL). White solid, yield (0.37 g, 58%).

7V-(2-(1,4-Thiazepan-4-yl)ethyl)-2-(hydroxyimino)acetamide (RS2-148B) Prepared according to the general method B. Ethyl glyoxylate oxime 3 (0.35 g, 3 mmol). 2-(1,4-thiazepan-4-yl)ethanamine (0.55 g, 3.45 mmol), ethanol (7 mL). White solid, yield (0.44 g, 61%). $^1$H NMR (400 MHz, dmso) δ 11.88 (s, 1H). 7.93 (s, 1H), 7.42 (s, 1H), 3.20 (q, J=6.3 Hz, 2H), 2.90 (t, J=5.1 Hz, 2H), 2.85 (t, J=5.9 Hz, 2H), 2.70-2.59 (m, 6H), 1.80 (pent, J=5.9 Hz, 2H). $^{13}$C NMR (400 MHz, DMSO-d6) δ 161.7, 143.7, 58.1, 54.6, 52.9, 36.8, 33.5, 31.0, 30.6.

REFERENCES

1. Sit, R. K., Radic', Z., Gerardi, V., Zhang, L., Garcia, E., Katalinic', M., Amitai, G., Kovarik, Z., Fokin, V. V., Sharpless, K. B., and Taylor, P. (2011) New structural scaffolds for centrally acting oxime reactivators of phosphylated cholinesterases. J. Biol. Chem. 286, 19422-19430.
2. Mercey, G., Verdelet, T., Saint-Andre', G., Gillon, E., Wagner, A., Baati, R., Jean, L., Nachon, F., and Renard, P. Y. (2011) First efficient uncharged reactivators for the dephosphylation of poisoned human acetylcholinesterase. Chem. Commun. 475, 5295-5297
3. de Koning, M. C, van Grol, M., and Noort, D. (2011) Peripheral site ligand conjugation to a non-quaternary oxime enhances reactivation of nerve agent-inhibited human acetylcholinesterase. Toxicol. Lett. 206, 54-59
4. Kalisiak, J., Ralph, E. C, Zhang, J., and Cashman, J. R. (2011) Amidineoximes. Reactivators for organophosphate exposure. J. Med Chem. 54, 3319-3330.
5. Demar, J. C, Clarkson, E. D., Ratcliffe, R. H., Campbell, A. J., Thangavelu, S. G., Herdman, C. A., Leader, H., Schulz, S. M., Marek, E., Medynets, M. A., Ku, T. C, Evans, S. A., Khan, F. A., Owens, R. R., Nambiar, M. P., and Gordon, R. K. (2010) Pro-2-PAM therapy for central and peripheral cholinesterases. Chem. Biol. Interact. 187, 191-198
6. Garcia, G. E., Campbell, A. J., Olson, J., Moorad-Doctor, D., and Morthole, V. I. (2010) Novel oximes as blood-brain barrier penetrating cholinesterase reactivators. Chem. Biol. Interact. 187, 199-206
7. Little, P. J., Scimeca, J. A., and Martin. B. R. (1988) Distribution of [3H]diisopropyfluorophosphate, [3H]soman, [3H]sarin and their metabolites in mouse brain. Drug Metab. Dispos. 16, 515-520
8. Wilson, I. B., and Bergmann, F. (1950) Studies on cholinesterase. VII. The active surface of acetylcholine esterase derived from effects of pH on inhibitors. J. Biol. Chem. 185, 479-489
9. Aldridge, W. N., and Reiner, E. (1972) Enzyme Inhibitors as Substrates, North Holland, Amsterdam
10. Sussman, J. L., Harel, M., Frolow. F., Oefner, C. Goldman. A., Toker. L., and Silman, I. (1991) Atomic structure of acetylcholinesterase from Torpedo californica. A prototypic acetylcholine-binding protein. Science 253, 872-879
11. Harel, M., Schalk, I., Ehret-Sabatier, L., Bouet, F., Goeldner, M., Hirth. C, Axelsen, P. H., Silman, I., and Sussman, J. L. (1993) Quaternary ligand binding to aromatic residues in the active site gorge of acetylcholinesterase. Proc. Natl. Acad. Sci. U.S.A. 90, 9031-9035
12. Lewis, W. G., Green, L. G., Grynszpan, F., Radic', Z., Carlier, P. R., Taylor, P., Finn, M. G., and Sharpless, K. B. (2002) Click chemistry in situ. Acetylcholinesterase as a reaction vessel for the selective assembly of a femtomolar inhibitor from an array of building blocks. Angew. Chem. Int. Ed. Engl. 41, 1053-1057
13. Radic', Z., and Taylor, P. (2006) in Toxicology of Organophosphate and Carbamate Compounds (Gupta, R., ed) pp. 161-186, Elsevier, Amsterdam
14. Silman. I., and Sussman, J. L. (2008) Acetylcholinesterase. How is structure related to function?Chem. Biol. Interact. 175, 3-10
15. Shih, T. M., Skovira, J. W., O'Donnell, J. C, and McDonough, J. H. (2010) In vivo reactivation by oximes of inhibited blood, brain, and peripheral tissue cholinesterase activity after exposure to nerve agents in guinea pigs. Chem. Biol. Interact. 187, 207-214
16. Cochran, R., Kalisiak, J., Ku' cXkkilinc., T., Radic', Z., Garcia, E., Zhang. L., Ho, K. Y., Amitai, G., Kovarik, Z., Fokin, V. V., Sharpless, K. B., and Taylor, P. (2011) Oxime-assisted acetylcholinesterase catalytic scavengers of organophosphates that resist aging. J. Biol. Chem. 286, 29718-29724.
17. Amitai. G., Adani, R., Yacov. G., Yishay, S., Teitlboim, S., Tveria, L., Limanovich, O., Kushnir, M., and Meshulam, H. (2007) Asymmetric fluorogenic organophosphates for the development of active organophosphate hydrolases with reversed stereoselectivity. Toxicology 233, 187-198

18. Ellman, G. L., Courtney, K. D., Andres V., Jr., and Feather-Stone, R. M. (1961) A new and rapid colorimetric determination of acetylcholinesterase activity. Biochem. Pharmacol. 7, 88-95
19. Kovarik, Z., Radic', Z., Berman, H A., Simeon-Rudolf, V., Reiner, E., and Taylor. P. (2004) Mutant cholinesterases possessing enhanced capacity for reactivation of their phosphonylated conjugates. Biochemistry 43, 3222-3229
20. Malany, S., Sawai, M., Sikorski, R. S., Seravalli, J., Quinn, D. M., Radic', Z., Taylor, P., Kronman, C, Velan, B., and Shafferman, A. (2000) Transition state structure and rate determination for the acylation stage of acetylcholinesterase-catalyzed hydrolysis of (acetylthio)choline. J. Am. Chem. Soc. 122, 2981-2987
21. Ashani, Y., Radic', Z., Tsigelny, I., Vellom, D. C, Pickering, N. A., Quinn, D. M., Doctor, B. P., and Taylor, P. (1995) Amino acid residues controlling reactivation of organophosphonyl conjugates of acetylcholinesterase by mono- and bisquaternary oximes. J. Biol. Chem. 270, 6370-6380
22. Thompson, W. R. (1947) Use of moving averages and interpolation to estimate median-effective dose. Bacteriol. Rev. 11, 115-145
23. Weil, C. S. (1952) Tables for convenient calculation of median-effective dose (LD50 or ED50) and instruction in their use. Biometrics 8, 249-263
24. C' alic', M., Vrdoljak, A. L., Radic', B., Jelic', D., Jun, D., Kuca, K., and Kovarik, Z. (2006) In vitro and in vivo evaluation of pyridinium oximes. Mode of interaction with acetylcholinesterase, effect on tabun- and soman-poisoned mice and their cytotoxicity. Toxicology 219, 85-96
25. Berend, S., Katalinic', M., Vrdoljak, A. L., Kovarik, Z., Kuca, K., and Radic', B. (2010) In vive experimental approach to treatment against tabun poisoning. J. Enzyme Inhib. Med. Chem. 25, 531-536
26. Wilson, I. B., and Froede, H. C. (1971) in Drug Design (Ariens, E. J., ed) Vol. II, pp. 213-229, Academic Press, New York
27. Cook, P. F., and Cleland, W. W. (2007) Enzyme Kinetics and Mechanism, pp. 225-368, Garland Science, London
28. Krasinski, A., Radic', Z., Manetsch, R., Raushel, J., Taylor, P., Sharpless, K. B., and Kolb, H. C. (2005) In situ selection of lead compounds by click chemistry: target-guided optimization of acetylcholinesterase inhibitors. J. Am. Chem. Soc. 127, 6686-6692.

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating, ameliorating or protecting or preventing an organophosphate toxicity or poisoning or toxic exposure, or for treating, ameliorating or protecting or preventing organophosphate inhibition of an acetylcholinesterase (AChE), comprising:
administering or having administered to a patient or an individual in need thereof, a pharmaceutical composition or a formulation comprising:
(a) a compound having the formula:

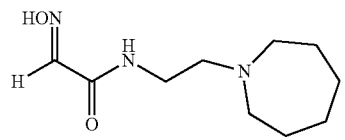

or
(b) a stereoisomer or a pharmaceutically acceptable salt of (a).

2. The method of claim 1, wherein the organophosphate toxicity, poisoning or toxic exposure is caused by exposure of the patient or individual to an alkyl methylphosphonate or related nerve agent, or an alkylphosphorate insecticide.

3. The method of claim 1, wherein the acetylcholinesterase (AChE) is in the central nerve system (CNS).

4. The method of claim 1, wherein the pharmaceutical compound or formulation is administered enterally or parenterally.

5. The method of claim 4, wherein the excessive acetylcholine stimulation in the brain, the CNS or the PNS is caused by a drug, a drug overdose, or a poisoning or a toxic exposure to a drug, and optionally the drug overdose causing the excessive acetylcholine stimulation is caused at least in part by physostigmine, neostigmine, pyridostigmine, diisopropylfluorophosphate and/or echothiophate.

6. The method of claim 2, wherein the organophosphate (OP) is or is a component of a toxin, an herbicide, an insecticide, or a nerve gas or nerve agent.

7. The method of claim 6, wherein the organophosphate (OP) is or comprises a parathion, a malathion, a methyl parathion, a chlorpyrifos, a diazinon, a dichlorvos, a phosmet, a fenitrothion, a tetrachlorvinphos, an azamethiphos or an azinphos methyl.

8. The method of claim 6, wherein the nerve agent is a soman (O-Pinacolyl methylphosphonofluoridate), a tabun (Ethyl N,NDimethyl-phosphoramido-cyanidate) or a sarin ((RS)-propan-2-yl methylphosphonofluoridate).

9. The method of claim 1, wherein the acetylcholinesterase (AChE) is a human acetylcholinesterase (hAChE).

10. The method of claim 1, wherein the pharmaceutical compound or formulation is administered orally, parenterally, by inhalation spray, nasally, topically, intrathecally, intrathecally, intracerebrally, epidurally, intracranially or rectally.

11. The method of claim 1, wherein the pharmaceutical compound or formulation is administered using a pump, a device, a subcutaneous infusion device, a continuous subcutaneous infusion device, an infusion pen, a needles, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector.

12. The method of claim 1, wherein the pharmaceutical composition or formulation further comprises a pharmaceutically acceptable carrier, an isotonic sodium chloride, or a sterile solvent or an excipient.

13. The method of claim 12, wherein the pharmaceutically acceptable carrier or excipient is or comprises: a carbohydrate or protein filler; a sugar, optionally lactose, sucrose, mannitol or sorbitol; a starch, optionally a starch from corn, wheat, rice, potato; a cellulose, optionally methyl cellulose, hydroxypropylmethyl-cellulose, or sodium carboxy-methylcellulose; a gum, optionally comprising arabic and tragacanth; a protein, optionally comprising a gelatin or a collagen; or, a combination thereof.

14. The method of claim 1, wherein the pharmaceutical composition or formulation is formulated as a pharmaceutically acceptable solid, liquid, aerosol, powder or emulsion.

15. The method of claim 1, wherein the pharmaceutical composition or formulation is formulated as a tablet, a pill, a powder, a dragee, a capsule, a lozenge, a gel, a syrup, a slurry or a suspension.

16. The method of claim 1, wherein the pharmaceutical composition or formulation is formulated for enteral or parenteral administration.

17. The method of claim 1, wherein the pharmaceutical composition or formulation is formulated for administration intramuscularly, orally, parenterally, by inhalation spray, nasally, topically, intrathecally, intrathecally, intracerebrally, epidurally, intracranially or rectally.

18. The method of claim 1, further comprising a solubilizer, an emulsifier, a buffer, a preservative, a sweetener, a flavoring agent, a suspending agent, a thickening agent, a color, a viscosity regulator, a stabilizer, an osmo-regulator, or a combination thereof.

19. The method of claim 1, wherein the concentration of the compound of (a) in a formulation is from between about 0.1% to about 100% by weight.

20. The method of claim 1, wherein the pharmaceutical composition or formulation is formulated with or in nanoparticle, a nanolipoparticle, a vesicle, a liposome, a multilayered liposome, or a liposomal membrane.

21. The method of claim 20, wherein the nanoparticle, nanolipoparticle, vesicle, liposome, multilayered liposome, or liposomal membrane comprises squalane, a sterol, a ceramides, a neutral lipids or oil, a fatty acid, a lecithin or a combination thereof.

22. The method of claim 1, wherein the pharmaceutical composition or formulation is formulated with: a cationic polymer; a cationic peptide, a polyethyleneimine derivative, or a combination thereof.

* * * * *